US011534440B2

(12) United States Patent
Lorens et al.

(10) Patent No.: US 11,534,440 B2
(45) Date of Patent: Dec. 27, 2022

(54) COMBINATION THERAPY WITH AXL INHIBITOR AND IMMUNE CHECKPOINT MODULATOR OR ONCOLYTIC VIRUS

(71) Applicant: BerGenBio ASA, Bergen (NO)

(72) Inventors: James Bradley Lorens, Bones (NO); Gro Gausdal, Loddefjord (NO)

(73) Assignee: BERGENBIO ASA, Bergn (NO)

( * ) Notice: Subject to any disclaimer, the term of this patent is extended or adjusted under 35 U.S.C. 154(b) by 0 days.

(21) Appl. No.: 16/738,103

(22) Filed: Jan. 9, 2020

(65) Prior Publication Data

US 2020/0215064 A1 Jul. 9, 2020

Related U.S. Application Data

(63) Continuation of application No. 15/577,804, filed as application No. PCT/GB2016/051542 on May 27, 2016, now abandoned.

(30) Foreign Application Priority Data

May 29, 2015 (GB) ..................................... 1509338
Sep. 16, 2015 (GB) ..................................... 1516442

(51) Int. Cl.
| | | |
|---|---|---|
| *A61K 31/502* | (2006.01) | |
| *A61K 39/395* | (2006.01) | |
| *A61K 45/06* | (2006.01) | |
| *A61P 35/00* | (2006.01) | |
| *C07K 16/28* | (2006.01) | |
| *A61K 39/00* | (2006.01) | |

(52) U.S. Cl.
CPC ........ *A61K 31/502* (2013.01); *A61K 39/3955* (2013.01); *A61K 45/06* (2013.01); *A61P 35/00* (2018.01); *C07K 16/2818* (2013.01); *C07K 16/2827* (2013.01); *C07K 16/2863* (2013.01); *A61K 2039/505* (2013.01); *A61K 2039/507* (2013.01); *A61K 2300/00* (2013.01); *C07K 2317/73* (2013.01); *Y02A 50/30* (2018.01)

(58) Field of Classification Search
CPC .... A61K 31/502; A61K 39/395; A61K 45/06; A61P 35/00
See application file for complete search history.

(56) References Cited

U.S. PATENT DOCUMENTS

| | | | |
|---|---|---|---|
| 9,175,091 B2 | 11/2015 | Kitazawa et al. | |
| 9,573,935 B2 | 2/2017 | Inukai et al. | |
| 2005/0118604 A1 | 6/2005 | Lorens et al. | |
| 2007/0213375 A1 | 9/2007 | Singh et al. | |
| 2008/0117789 A1 | 5/2008 | Yokota et al. | |
| 2008/0153815 A1 | 6/2008 | Singh et al. | |
| 2008/0176847 A1 | 7/2008 | Goff et al. | |
| 2008/0182862 A1 | 7/2008 | Ding et al. | |
| 2008/0188454 A1 | 8/2008 | Goff et al. | |
| 2008/0188455 A1 | 8/2008 | Goff et al. | |
| 2008/0188474 A1 | 8/2008 | Goff et al. | |
| 2009/0111816 A1 | 4/2009 | Singh et al. | |
| 2011/0009281 A1 | 1/2011 | Micklem et al. | |
| 2012/0121587 A1 | 5/2012 | Maeda et al. | |
| 2017/0326234 A1 | 11/2017 | Renschler et al. | |

FOREIGN PATENT DOCUMENTS

| | | |
|---|---|---|
| EP | 2228392 | 9/2010 |
| EP | 2267454 | 12/2010 |
| EP | 3026045 | 6/2016 |
| WO | 0054795 | 9/2000 |
| WO | 2007030680 | 3/2007 |
| WO | 2007113648 | 10/2007 |
| WO | 2008045976 | 4/2008 |
| WO | 2008/086342 A2 | 7/2008 |
| WO | 2008080134 | 7/2008 |
| WO | 2008083353 | 7/2008 |
| WO | 2008083354 | 7/2008 |
| WO | 2008083356 | 7/2008 |
| WO | 2008083357 | 7/2008 |
| WO | 2008083367 | 7/2008 |
| WO | 2008/127707 A1 | 10/2008 |
| WO | 2008128072 | 10/2008 |
| WO | 2000054864 | 4/2009 |
| WO | 2009062690 | 5/2009 |
| WO | 2009063965 | 5/2009 |
| WO | 2009/079335 A1 | 6/2009 |
| WO | 2010083465 | 7/2010 |
| WO | 2010130751 | 11/2010 |
| WO | 2011/041613 A2 | 4/2011 |

(Continued)

OTHER PUBLICATIONS

Golub et al. Science, vol. 286, Oct. 15, 1999, pp. 531-537.*
Kanwal et al. Oncology Letters, 2017, vol. 13, pp. 535-542.*
Gupta et al. Fundamentals of Toxicology, 2016, pp. 19-49.*
International Search Report for PCT/GB201 6/051 542, Completed by the European Patent Office dated Jul. 27, 2016, 5 Pages.
Chen et al. Molecular Therapy Dec. 2007, vol. 15, No. 12, pp. 2194-2202, "Rejection of metastatic 4T1 breat cancer by attenuation of Treg cells in Combination with immune Stimulation".
Chen et al. Nat. Commun. Oct. 28, 2014, 5:5241, 24 Pages, "Metastasis is Regulated via microRNA-200/ZEB1 asis control of tumour cell PD-L1 Expression and Intratumoral Immunosuppression".
Gjerdrum et al. PNAS Jan. 19, 2010, vol. 107, No. 3, pp. 1124-1129, "Axl is an Essential Epithelial-to-mesenchymal Transition-Induced regulator of breat cancer metastasis and Patient Survival".

(Continued)

*Primary Examiner* — Samira J Jean-Louis
(74) *Attorney, Agent, or Firm* — Arnold & Porter Kaye Scholer LLP

(57) ABSTRACT

An Axl inhibitor and one or more immune checkpoint (activity) modulators and/or one or more oncolytic viruses, for use in the prevention, treatment or management of cancer, wherein the Axl inhibitor and the one or more immune checkpoint (activity) modulators and/or the one or more oncolytic viruses are administered concurrently, separately or sequentially; compositions containing such components in combination; and methods of treating cancer in a patient by administering such components in combination.

18 Claims, 11 Drawing Sheets

(56) References Cited

FOREIGN PATENT DOCUMENTS

| WO | 2011146382 | 11/2011 |
| WO | 2011159980 | 12/2011 |
| WO | 2012/032433 A1 | 3/2012 |
| WO | 2012175691 | 12/2012 |
| WO | 2012175692 | 12/2012 |
| WO | 2013180949 | 12/2013 |
| WO | 2014158811 | 10/2014 |
| WO | 2015012298 | 1/2015 |
| WO | 2015193428 | 12/2015 |
| WO | 2015193430 | 12/2015 |
| WO | 2016097370 | 6/2016 |

OTHER PUBLICATIONS

Grosso et al. Cancer Immunity Jan. 22, 2013, vol. 13, p. 5, 14 Pages, "CTLA-4 blockade in tumor models: an overview of preclinical and translational research".
Kyi et al., FEBS Letters Jan. 21, 2014, vol. 588, No. 2, pp. 368-376, "Checkpoint blocking antibodies in cancer immunotherapy".
Rothlin et al. Cell Dec. 14, 2007, vol. 131, No. 6, pp. 1124-1136, "TAM Receptors are Pleiotropic Inhibitors of the Innate Immune Response".
Loges et al. Blood Mar. 18, 2010, vol. 115, No. 11, pp. 2264-2273, "Malignant cells fuel tumor growth by educating infiltrating leukocytes to produce the mitogen Gas6".
Straume et al. 9th World Congress of Melanoma Oct. 18-21, 2017, 1 Page, "A Phase Ib/II randomised study of BGB324, a first-in-class selective AXL inhibitor, in combination with pembrolizumab or dabrafenib/trametinib in patients with advanced melanoma".
Gausdal et al. Jan. 1, 2016, XP55290621, http://cancerimmunolres.aacrjournals.org/contect/4/1_Supplement/B014 "Abstract B014; BGB324, a selective small molecule inhibitor of the receptor tyrosine kinase AXL, enhances immune checkpoint inhibitor efficacy".
Ai et al. Cancer Immunol Immunother, Accepted Dec. 19, 2014, 8 Pages, "Immune checkpoint combinations from mouse to man".
Shin et al. Current Opinion in Immunology 2015, vol. 33, pp. 23-35, "The evolution of checkpoint blockage as a cancer therapy: what's here, what's next?".
Everts et al. Cancer Gene Therapy 2005, vol. 12, pp. 141-161, "Replication-seiective oncolytic viruses in the treatment of cancer".
Kudo-Saito et al. Cancer Cell Mar. 3, 2009, vol. 15, pp. 195-206, "Cancer Metastasis Is Accelerated through Immunosuppression during Snail-Induced EMT of Cancer Cells".
Akalay et al. Cancer Research Apr. 15, 2013, vol. 73, No. 8, pp. 2418-2428, Published Online First Feb. 22, 2013, "Epithelial-to-Mesenchymal Transition and Autophagy Induction in Breast Carcinoma Promote Escape from T-cell-Mediated Lysis".
Chiu et al. Oral Oncology 2015, 7 Pages, "Polarization of tumor-associated macrophages and Gas6/Axl signaling in oral squamous cell carcinoma".
Lu et al. J Oncol Pharm Pract. 2015, vol. 21, No. 6, pp. 451-467, "Clinical Evaluation of Compounds Targeting PD-1/PD-L1 Pathway for Cancer Immunotherapy".
Paolino et al. Nature Mar. 27, 2014, vol. 507, No. 7493, 19 Pages, "The E3 Ligase Cbl-b and TAM Receptors Regulate Cancer Metastasis Via Natural Killer Cells".
Ye et al. Oncogene 2010, vol. 29, pp. 5254-5264, "An ant-Axl monoclonal antibody attenuates xenograft tumor growth and enhances the effect of multiple anticancer therapies".
Das, R. et al., "Combination Therapy with Anti-CTLA-4 and Anti-PD-1 Leads to Distinct Immunologic Changes In Vivo," The Journal of Immunology, v. 194, Issue 3, 2015, pp. 950-959.
Lines, J.L. et al., "VISTA is a Novel Broad-Spectrum Negative Checkpoint Regulator for Cancer Immunotherapy," Cancer Immunol. Res 2014, 2(6), pp. 510-517.
International Preliminary Report on Patentability, dated Dec. 5, 2017, in International Appln. PCT/GB2016/051542.
International Search Report and Written Opinion of the International Searching Authority, dated Aug. 8, 2016, in International Appln. PCT/GB2016/051542.
Lichty et al., "Going Viral with Cancer Immunotherapy," Nature Reviews Cancer, 14:559-567 (2014).
Lou et al., "Association of Epithelial-Mesenchymal Transition Status with PD1/PDL1 Expression and a Distinct Immunophenotype in Non-Small Cell Lung Cancer: Implications for Immunotherapy Biomarkers," J. Clin Oncol., 32(15 Suppl.):Abstr. 3018, 2 pp. (2014).
Pulsaki et al., "Mouse 4T1 Breast Tumor Model," Curr. Protocols in Immunol., Supplement 39, p. 20.2.1-20.2.16 (2000).

\* cited by examiner

MEDIAN SURVIVAL
17 ······ PBS + Vehicle
17 ···*··· IgG + BGB324
18 —■— Anti-PD-1 + Anti-PD-L1 + Vehicle
20 —■— Anti-PD-1 + anti-PD-L1 + BGB324

**, P=0.006

COMBINATION THERAPY WITH AXL INHIBITOR AND IMMUNE CHECKPOINT MODULATOR OR ONCOLYTIC VIRUS

CROSS-REFERENCE TO RELATED APPLICATION

This application is a continuation of U.S. Ser. No. 15/577,804 filed Nov. 29, 2017, which is the U.S. national phase of PCT Application No. PCT/GB2016/051542 filed on May 27, 2016, which claims priority to GB Patent Application No. 1509338.8 filed on May 29, 2015 and GB Patent Application No, 1516442.9 filed on Sep. 16, 2015, the disclosures of which are incorporated in their entirety by reference herein.

The present invention relates to a combination therapy. In particular, although not exclusively, it concerns combination therapies comprising an Axl inhibitor and one or more immune checkpoint (activity) modulators and/or one or more oncolytic viruses for the prevention, treatment, or management of cancer.

All of the protein kinases that have been identified to date in the human genome share a highly conserved catalytic domain of around 300 aa. This domain folds into a bi-lobed structure in which resides ATP-binding and catalytic sites. The complexity of protein kinase regulation allows many potential mechanisms of inhibition including competition with activating ligands, modulation of positive and negative regulators, interference with protein dimerization, and allosteric or competitive inhibition at the substrate or ATP binding sites.

Axl (also known as UFO, ARK, and Tyro7; nucleotide accession numbers NM_021913 and NM_001699; protein accession numbers NP_068713 and NP_001690) is a receptor protein tyrosine kinase (RTK) that comprises a C-terminal extracellular ligand-binding domain and N-terminal cytoplasmic region containing the catalytic domain. The extracellular domain of Axl has a unique structure that juxtaposes immunoglobulin and fibronectin Type III repeats and is reminiscent of the structure of neural cell adhesion molecules. Axl and its two close relatives, Mer/Nyk and Sky (Tyro3/Rse/Dtk), collectively known as the Tyro3 family of RTK's, all bind and are stimulated to varying degrees by the same ligand, Gas6 (growth arrest specific-6), a ~76 kDa secreted protein with significant homology to the coagulation cascade regulator, Protein S. In addition to binding to ligands, the Axl extracellular domain has been shown to undergo homophilic interactions that mediate cell aggregation, suggesting that one important function of Axl may be to mediate cell-cell adhesion.

Axl is predominantly expressed in the vasculature in both endothelial cells (EC's) and vascular smooth muscle cells (VSMC's) and in cells of the myeloid lineage and is also detected in breast epithelial cells, chondrocytes, Sertoli cells and neurons. Several functions including protection from apoptosis induced by serum starvation, TNF-α or the viral protein E1A, as well as migration and cell differentiation have been ascribed to Axl signaling in cell culture. However, Axl−/− mice exhibit no overt developmental phenotype and the physiological function of Axl in vivo is not clearly established in the literature.

The overexpression of Axl and/or its ligand has also been reported in a wide variety of solid tumor types including, but not limited to, breast, renal, endometrial, ovarian, thyroid, non-small cell lung carcinoma, and uveal melanoma as well as in myeloid leukemia's. Furthermore, it possesses transforming activity in NIH3T3 and 32D cells. It has been demonstrated that loss of Axl expression in tumor cells blocks the growth of solid human neoplasms in an in vivo MDA-MB-231 breast carcinoma xenograft model. Taken together, these data suggest Axl signaling can independently regulate EC angiogenesis and tumor growth and thus represents a novel target class for tumor therapeutic development.

The expression of Axl and Gas6 proteins is upregulated in a variety of other disease states including endometriosis, vascular injury and kidney disease and Axl signaling is functionally implicated in the latter two indications. Axl-Gas6 signaling amplifies platelet responses and is implicated in thrombus formation. Axl may thus potentially represent a therapeutic target for a number of diverse pathological conditions including solid tumors, including, but not limited to, breast, renal, endometrial, ovarian, thyroid, non-small cell lung carcinoma and uveal melanoma; liquid tumors, including but not limited to, leukemias (particularly myeloid leukemias) and lymphomas; endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoporosis, osteoarthritis and cataracts.

U.S. Published Patent Application No. 20070213375, U.S. Published Patent Application No. 20080153815, U.S. Published Patent Application No. 20080188454, U.S. Published Patent Application No. 20080176847, U.S. Published Patent Application No. 20080188455, U.S. Published Patent Application No. 20080182862, U.S. Published Patent Application No. 20080188474, U.S. Published Patent Application No. 20080117789, U.S. Published Patent Application No. 20090111816, PCT Published Patent Application No. WO 2007/0030680, PCT Published Patent Application No. WO 2008/045978, PCT Published Patent Application No. WO 2008/083353, PCT Published Patent Application No. WO 2008/0083357, PCT Published Patent Application No. WO 2008/083367, PCT Published Patent Application No. WO 2008/083354, PCT Published Patent Application No. WO 2008/083356, PCT Published Patent Application No. WO 2008/080134, PCT Published Patent Application No. WO 2009/054864, and PCT Published Patent Application No. WO 2010/083465 disclose compounds which are useful as Axl inhibitors.

Immune responses to cancer can lead to control and even elimination of tumors. Therapeutic targeting of tumor immune regulators has resulted in the development of successful immunotherapeutic approaches for cancer treatment. Immune modulatory antibodies that directly enhance the activity of tumor-specific effector T cells ($T_{eff}$) and eliminate immune suppressive regulatory T cells ($T_{reg}$) have earned significant recent attention. These agents, commonly called "immune checkpoint (activity) modulators", modify the activity of regulators of T cell immunity, for example block the activity of negative regulators of T cell immunity, such as a cytotoxic T-lymphocyte antigen 4 (CTLA-4) and programmed death receptor-1 (PD-1) (Kyi et al., 2014; Lu et al., 2014; Grosso et al., 2013). The term "immune checkpoint (activity) modulators" as used herein is intended to include immune checkpoint inhibitors, T cell co-stimulatory agonists, and dendritic cell co-stimulatory agonists (Ai and Curran, *Cancer Immmmol. Immunother.*, 3 Jan. 2015, Epublication).

FDA approval of anti-CTLA-4 antibody Yervoy™ ipilimumab (2012) and of two anti-PD-1 antibodies Keytruda™ pembrolizumab (2014) and Opdivo™ nivolumab (2014)

demonstrated that 'releasing the brakes' in tumor-specific T cells is very efficient in treatment of highly immunogenic cancer types, such as melanoma. In March 2015, FDA expanded use of nivolumab by approving it for treatment on non-small cell lung cancer (NSCLC). The checkpoint inhibitors are currently in clinical trials in several cancer types including bladder cancer, kidney cancer and head-and-neck cancer (Lu et al., 2014). Despite this success, immunotherapy against poorly immunogenic cancers remains a challenge. Co-administration with a second drug to enhance or prime the effect of immune checkpoint (activity) modulators by inhibiting resistance mechanisms is therefore an important goal for the pharmaceutical industry.

Whilst various combination therapies may have been previously suggested to target the prevention or treatment of cancer, it is not possible to hypothesise with confidence whether a given combination will actually elicit a beneficial response. Moreover, it is almost impossible to predict whether a synergistic effect could or would be obtained from a certain combination of therapeutic agents.

Accordingly, in a first aspect, the present invention is based on the surprising observation that the combination of an Axl inhibitor and one or more immune checkpoint (activity) modulators provides a significantly better therapeutic profile than current single agent therapies or other combination therapies utilising Axl inhibitors. Encompassed by the invention, therefore, are combination therapies of an Axl inhibitor with one or more immune checkpoint (activity) modulators that have a synergistic potency and/or therapeutic effect, e.g. a synergy exists between the Axl inhibitor and the one or more immune checkpoint (activity) modulators when co-administered. Preferably, such combination therapies also reduce or avoid unwanted or adverse effects. In certain embodiments, doses of existing immune checkpoint (activity) modulators can be reduced or administered less frequently in using the combination therapies of the invention, thereby increasing patient compliance, improving therapy and reducing unwanted or adverse effects.

Accordingly, in a first aspect, this invention is directed to an Axl inhibitor and one or more immune checkpoint (activity) modulators for use in the prevention, treatment or management of cancer, wherein the Axl inhibitor and the one or more immune checkpoint (activity) modulators are administered concurrently, separately or sequentially.

In one preferred embodiment, the Axl inhibitor is an anti-Axl antibody.

In an alternative preferred embodiment, the Axl inhibitor is a compound of formula (I):

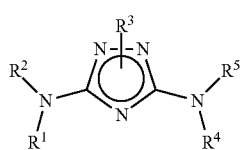

(I)

wherein:
$R^1$, $R^4$ and $R^5$ are each independently selected from the group consisting of hydrogen, alkyl, alkenyl, aryl, aralkyl, —C(O)$R^8$, —C(O)N($R^6$)$R^7$, and —C(=N$R^6$)N($R^6$)$R^7$;
$R^2$ and $R^3$ are each independently a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—O$R^8$, —$R^9$—O—$R^{10}$—O$R^8$, —$R^9$—O—$R^{10}$—O—$R^{10}$—O$R^8$, —$R^9$—O—$R^{10}$—C(O)O$R^8$, —$R^9$—O—$R^{10}$—C(O)N($R^6$)$R^7$, —$R^9$—O—$R^{10}$—S(O)$_p$$R^8$ (where p is 0, 1 or 2), —$R^9$—O—$R^{10}$—N($R^6$)$R^7$, —$R^9$—O—$R^{10}$—C(N$R^{11}$)N($R^{11}$)H, —$R^9$—OC(O)—$R^8$, —$R^9$—N($R^6$)$R^7$, —$R^9$—C(O)$R^8$, —$R^9$—C(O)O$R^8$, —$R^9$—C(O)N($R^6$)$R^7$, —$R^9$—N($R^6$)C(O)O$R^8$, —$R^9$—N($R^6$)C(O)$R^8$, —$R^9$—N($R^6$)S(O)$_t$$R^8$ (where t is 1 or 2), —$R^9$—S(O)$_t$O$R^8$ (where t is 1 or 2), —$R^9$—S(O)$_p$$R^8$ (where p is 0, 1 or 2), and —$R^9$—S(O)$_t$N($R^6$)$R^7$ (where t is 1 or 2);

or $R^2$ is a polycyclic heteroaryl containing more than 14 ring atoms as described above and $R^3$ is selected from the group consisting of aryl and heteroaryl, where the aryl and the heteroaryl are each independently optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—O$R^{12}$, —$R^{13}$—OC(O)—$R^{12}$, —$R^{13}$—O—$R^{14}$—N($R^{12}$)$_2$, —$R^{13}$—N($R^{12}$)—$R^{14}$—N($R^{12}$)$_2$, —$R^{13}$—N($R^{12}$)—$R^{14}$—N($R^{12}$)$_2$, —$R^{13}$—N($R^{12}$)$_2$, —$R^{13}$—C(O)$R^{12}$, —$R^{13}$—C(O)O$R^{12}$, —$R^{13}$—C(O)N($R^{12}$)$_2$, —$R^{13}$—C(O)N($R^{12}$)—$R^{14}$—N($R^{12}$)$R^{13}$, —$R^{13}$—C(O)N($R^{12}$)—$R^{14}$—O$R^{12}$, —$R^{13}$—N($R^{12}$)C(O)O$R^{12}$, —$R^{13}$—N($R^{12}$)C(O)$R^{12}$, —$R^{13}$—N($R^{12}$)S(O)$_t$—$^{12}$ (where t is 1 or 2), —$R^{13}$—S(O)$_t$O$R^{12}$ (where t is 1 or 2), —$R^{13}$—S(O)$_p$$R^{12}$ (where p is 0, 1 or 2), and —$R^{13}$—S(O)$_t$N($R^{12}$)$_2$ (where t is 1 or 2);

or $R^3$ is a polycyclic heteroaryl containing more than 14 ring atoms as described above, and $R^2$ is selected from the group consisting of aryl and heteroaryl, where the aryl and the heteroaryl are each independently optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—O$R^{12}$, —$R^{13}$—OC(O)—$R^{12}$, —$R^{13}$—O—$R^{14}$—N($R^{12}$)$_2$, —$R^{13}$—N($R^{12}$)—$R^{14}$—N($R^{12}$)$_2$, —$R^{13}$—N($R^{12}$)—$R^{14}$—N($R^{12}$)$_2$, —$R^{13}$—N($R^{12}$)$_2$, —$R^{13}$—C(O)$R^{12}$, —$R^{13}$—C(O)O$R^{12}$, —$R^{13}$—C(O)N($R^{12}$)$_2$, —$R^{13}$—C(O)N($R^{12}$)—$R^{14}$—N($R^{12}$)$R^{13}$, —$R^{13}$—C(O)N($R^{12}$)—$R^{14}$—O$R^{12}$, —$R^{13}$—N($R^{12}$)C(O)O$R^{12}$, —$R^{13}$—N($R^{12}$)C(O)$R^{12}$, —$R^{13}$—N($R^{12}$)S(O)$_t$$R^{12}$ (where t is 1 or 2), —$R^{13}$—

$S(O)_tOR^{12}$ (where t is 1 or 2), $-R^{13}-S(O)_pR^{12}$ (where p is 0, 1 or 2), and $-R^{13}-S(O)N(R^{12})_2$ (where t is 1 or 2);

each $R^6$ and $R^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl $-R^{10}-OR^8$, $-R^{10}-CN$, $-R^{10}-NO_2$, $-R^{10}-N(R^8)_2$, $-R^{10}-C(O)OR^8$ and $-R^{10}-C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

each $R^9$ is independently selected from the group consisting of a direct bond, an optionally substituted straight or branched alkylene chain, an optionally substituted straight or branched alkenylene chain and an optionally substituted straight or branched alkynylene chain;

each $R^{10}$ is independently selected from the group consisting of an optionally substituted straight or branched alkylene chain, an optionally substituted straight or branched alkenylene chain and an optionally substituted straight or branched alkynylene chain;

each $R^{11}$ is independently selected from the group consisting of hydrogen, alkyl, cyano, nitro and $-OR^8$;

each $R^{12}$ is independently selected from the group consisting of hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl, optionally substituted heteroarylalkyl, $-R^{10}-OR^8$, $-R^{10}-CN$, $-R^{10}-NO_2$, $-R^{10}-N(R^8)_2$, $-R^{10}-C(O)OR^8$ and $-R^{10}-C(O)N(R^8)_2$, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond, an optionally substituted straight or branched alkylene chain and an optionally substituted straight or branched alkenylene chain; and each $R^{14}$ is independently selected from the group consisting of an optionally substituted straight or branched alkylene chain and an optionally substituted straight or branched alkenylene chain;

as an isolated stereoisomer or mixture thereof or as a tautomer or mixture thereof, or a pharmaceutically acceptable salt or N-oxide thereof.

In addition, in a second aspect, this invention provides methods of preventing, treating or managing cancer in a patient comprising administering to the patient in need thereof a therapeutically or prophylactically effective amount of an Axl inhibitor, in concurrent, separate or sequentially combination with a therapeutically or prophylactically effective amount of one or more immune checkpoint (activity) modulators.

In a third aspect of the invention, there is provided an Axl inhibitor, for use in the prevention, treatment or management of cancer, wherein the prevention, treatment or management of cancer is in a patient to whom an immune checkpoint (activity) modulator has been or will be administered.

In a fourth aspect, the invention provides a method of preventing, treating or managing cancer in a patient to whom an immune checkpoint (activity) modulator has been or will be administered, the method comprising administering to a patient in need thereof a therapeutically or prophylactically effective amount of an Axl inhibitor.

In a fifth aspect of the invention, there is provided a pharmaceutical composition comprising an Axl inhibitor, one or more immune checkpoint (activity) modulators, and a pharmaceutically acceptable excipient.

These aspects are based on the surprising observation that there is a synergistic interaction between an Axl inhibitor and one or more immune checkpoint (activity) modulators, which provides a significantly better therapeutic profile than when each agent is used in isolation, i.e. there is an effect which surpasses expecations based on additive effects.

In a sixth aspect of the invention, there is provided an Axl inhibitor and one or more oncolytic viruses, for use in the prevention, treatment or management of cancer, wherein the Axl inhibitor and the one or more oncolytic viruses are administered concurrently, separately or sequentially.

This aspect is based on the surprising observation that the combination of an Axl inhibitor and one or more oncolytic viruses provides a significantly better therapeutic profile than current single agent therapies or other combination therapies utilising Axl inhibitors. Encompassed by the invention, therefore, are combination therapies of an Axl inhibitor with one or more oncolytic viruses that have a synergistic potency and/or therapeutic effect, e.g. a synergy exists between the Axl inhibitor and the one or more oncolytic viruses when co-administered. Preferably, such combination therapies also reduce or avoid unwanted or adverse effects. In certain embodiments, doses of existing oncolytic viruses can be reduced or administered less frequently in using the combination therapies of the invention, thereby increasing patient compliance, improving therapy and reducing unwanted or adverse effects.

In particular, it is believed that the oncolytic virus functions to stimulate an immune response in tumours, thereby potentiating the immune response in combination with the Axl inhibitor. The virus generates long stranded RNA molecules that drive an innate response via toll-like receptors (TRL) and type I interferon (IFNa) activation, which appears to potentiate the effect of the Axl inhibitor since Axl signalling has a suppressive effect on TRL/IFNa. Although the prior art (e.g. Lichty, B. D. et al. Nature Reviews 2014, 14, 559-567; WO 2014/158811) describes combination therapies comprising oncolytic viruses and immune checkpoint inhibitors, there is no indication that combination therapies comprising oncolytic viruses and Axl inhibitors, which act at different biochemical targets compared to immune checkpoint inhibitors, would provide the synergistic effects observed.

These effects are even more surprising and pronounced when the Axl inhibitor and one or more oncolytic viruses are used in further combination with one or more immune checkpoint (activity) modulators, wherein the Axl inhibitor, the one or more oncolytic viruses and the one or more immune checkpoint (activity) modulators are administered concurrently, separately or sequentially. Particularly in relation to "cold" tumours, which have low immunogenicity and a poor response to immune checkpoint inhibitors, Axl inhibition in combination with oncolytic virus treatment has surprisingly been found to provide a potentiated immune response, and significantly reinforce the effect of immune checkpoint modulation (especially checkpoint inhibition).

Preferred examples of oncolytic viruses include reovirus, Newcastle disease virus, adenovirus, herpes virus (e.g. herpes simplex 1), polio virus, mumps virus, measles virus, influenza virus, vaccinia virus, rhabdovirus, parvovirus, vesicular stomatitis virus, and derivatives and variants thereof.

In a seventh aspect of the invention, there is provided a method of preventing, treating or managing cancer in a patient comprising administering to the patient in need thereof a therapeutically or prophylactically effective amount of an Axl inhibitor in concurrent, separate or sequential combination with a therapeutically or prophylactically effective amount of one or more oncolytic viruses.

This method may further comprise administering to the patient in need thereof a therapeutically or prophylactically effective amount of one or more immune checkpoint (activity) modulators in concurrent, separate or sequential combination.

In an eighth aspect of the invention, there is provided an Axl inhibitor, for use in the prevention, treatment or management of cancer, wherein the prevention, treatment or management of cancer is in a patient to whom an oncolytic virus has been or will be administered.

The prevention, treatment or management of cancer is in a patient may be to whom an immune checkpoint (activity) modulator has also been or will also be administered.

In a ninth aspect of the invention, there is provided a method of preventing, treating or managing cancer in a patient to whom an oncolytic virus has been or will be administered, the method comprising administering to a patient in need thereof a therapeutically or prophylactically effective amount of an Axl inhibitor.

In this method of preventing, treating or managing cancer in a patient, an immune checkpoint (activity) modulator may also have been or will also be administered.

In a tenth aspect of the invention, there is provided a pharmaceutical composition comprising an Axl inhibitor, one or more oncolytic viruses, and a pharmaceutically acceptable excipient. The pharmaceutical composition may further comprise one or more immune checkpoint (activity) modulators.

These aspects are based on the surprising observation that there is a synergistic interaction between an Axl inhibitor and one or more oncolytic viruses (preferably in further combination with one or more immune checkpoint (activity) modulators, since the combination unexpectedly reinforces checkpoint modulation), which provides a significantly better therapeutic profile than when each agent is used in isolation, i.e. there is an effect which surpasses expecations based on additive effects.

As will be appreciated by one skilled in the art, any of the preferred embodiments of the first aspect of the invention apply equally to any of the second to tenth aspects of the invention.

As used in the specification and appended claims, unless specified to the contrary, the following terms have the meaning indicated:

"Amino" refers to the —$NH_2$ radical.
"Carboxy" refers to the —C(O)OH radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms and which is attached to the rest of the molecule by a single bond, for example, methyl, ethyl, n-propyl, 1-methylethyl (iso-propyl), n-butyl, n-pentyl, 1,1-dimethylethyl (t-butyl), 3-methylhexyl, 2-methylhexyl, and the like. For purposes of this invention, the term "lower alkyl" refers to an alkyl radical having one to six carbon atoms.

"Optionally substituted alkyl" refers to an alkyl radical, as defined above, which is optionally substituted by one or more substituents selected from the group consisting of halo, cyano, nitro, oxo, thioxo, trimethylsilanyl, —$OR^{20}$, —OC(O)—$R^{20}$, —$N(R^{20})_2$, —$C(O)R^{20}$, —$C(O)OR^{20}$, —$C(O)N(R^{20})_2$, —$N(R^{20})C(O)OR^{20}$, —$N(R^{20})C(O)R^{20}$, —$N(R^{20})S(O)_2R^{20}$, —$S(O)_tOR^{20}$ (where t is 1 or 2), —$S(O)_pR^{20}$ (where p is 0, 1 or 2), and —$S(O)_2N(R^{20})_2$ where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl.

"Alkenyl" refers to a straight or branched hydrocarbon chain radical consisting solely of carbon and hydrogen atoms, containing at least one double bond, having from two to twelve carbon atoms, preferably one to eight carbon atoms and which is attached to the rest of the molecule by a single bond, for example, ethenyl, prop-1-enyl, but-1-enyl, pent-1-enyl, and penta-1,4-dienyl.

"Optionally substituted alkenyl" refers to an alkenyl radical, as defined above, which is optionally substituted by one or more substituents selected from the group consisting of halo, cyano, nitro, oxo, thioxo, trimethylsilanyl, —$OR^{20}$, —OC(O)—$R^{20}$, —$N(R^{20})_2$, —$C(O)R^{20}$, —$C(O)OR^{20}$, —$C(O)N(R^{20})_2$, —$N(R^{20})C(O)OR^{20}$, —$N(R^{20})C(O)R^{20}$, —$N(R^{20})S(O)_2R^{20}$, —$S(O)_tOR^{20}$ (where t is 1 or 2), —$S(O)_p R^{20}$ (where p is 0, 1 or 2), and —$S(O)_2N(R^{20})_2$ where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl.

"Alkynyl" refers to a straight or branched hydrocarbon chain radical consisting solely of carbon and hydrogen atoms, containing at least one triple bond, optionally containing at least one double bond, having from two to twelve carbon atoms, preferably one to eight carbon atoms and which is attached to the rest of the molecule by a single bond, for example, ethynyl, propynyl, butynyl, pentynyl, and hexynyl.

"Optionally substituted alkynyl" refers to an alkynyl radical, as defined above, which is optionally substituted by one or more substituents selected from the group consisting of halo, cyano, nitro, oxo, thioxo, trimethylsilanyl, —$OR^{20}$, —$OC(O)$—$R^{20}$, —$N(R^{20})_2$, —$C(O)R^{20}$, —$C(O)OR^{20}$, —$C(O)N(R^{20})_2$, —$N(R^{20})C(O)OR^{20}$, —$N(R^{20})C(O)R^{20}$, —$N(R^{20})S(O)_2R^{20}$, —$S(O)_tOR^{20}$ (where t is 1 or 2), —$S(O)_p R^{20}$ (where p is 0, 1 or 2), and —$S(O)_2N(R^{20})_2$ where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl.

"Straight or branched alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, and n-butylene. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain.

"Optionally substituted straight or branched alkylene chain" refers to an alkylene chain, as defined above, which is optionally substituted by one or more substituents selected from the group consisting of halo, cyano, nitro, aryl, cycloalkyl, heterocyclyl, heteroaryl, oxo, thioxo, trimethylsilanyl, —$OR^{20}$, —$OC(O)$—$R^{20}$, —$N(R^{20})_2$, —$C(O)R^{20}$, —$C(O)OR^{20}$, —$C(O)N(R^{20})_2$, —$N(R^{20})C(O)OR^{20}$, —$N(R^{20})C(O)R^{20}$, —$N(R^{20})S(O)_2R^{20}$, —$S(O)_tOR^{20}$ (where t is 1 or 2), —$S(O)_pR^{20}$ (where p is 0, 1 or 2), and —$S(O)_2N(R^{20})_2$ where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl.

"Straight or branched alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, and n-butenylene. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain.

"Optionally substituted straight or branched alkenylene chain" refers to an alkenylene chain, as defined above, which is optionally substituted by one or more substituents selected from the group consisting of halo, cyano, nitro, aryl, cycloalkyl, heterocyclyl, heteroaryl, oxo, thioxo, trimethylsilanyl, —$OR^{20}$, —$OC(O)$—$R^{20}$, —$N(R^{20})_2$, —$C(O)R^{20}$, —$C(O)OR^{20}$, —$C(O)N(R^{20})_2$, —$N(R^{20})C(O)OR^{20}$, —$N(R^{20})C(O)R^{20}$, —$N(R^{20})S(O)_2R^{20}$, —$S(O)_tOR^{20}$ (where t is 1 or 2), —$S(O)_pR^{20}$ (where p is 0, 1 or 2), and —$S(O)_2N(R^{20})_2$ where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl.

"Straight or branched alkynylene chain" refers to a straight or branched divalent hydrocarbon chain linking the rest of the molecule to a radical group, consisting solely of carbon and hydrogen, containing at least one triple bond and having from two to twelve carbon atoms, for example, propynylene, and n-butynylene. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain.

"Optionally substituted straight or branched alkynylene chain" refers to an alkynylene chain, as defined above, which is optionally substituted by one or more substituents selected from the group consisting of alkyl, alkenyl, halo, haloalkenyl, cyano, nitro, aryl, cycloalkyl, heterocyclyl, heteroaryl, oxo, thioxo, trimethylsilanyl, —$OR^{20}$, —$OC(O)$—$R^{20}$, —$N(R^{20})_2$, —$C(O)R^{20}$, —$C(O)OR^{20}$, —$C(O)N(R^{20})_2$, —$N(R^{20})C(O)OR^{20}$, —$N(R^{20})C(O)R^{20}$, —$N(R^{20})S(O)_2R^{20}$, —$S(O)_tOR^{20}$ (where t is 1 or 2), —$S(O)_pR^{20}$ (where p is 0, 1 or 2), and —$S(O)_2N(R^{20})_2$ where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl.

"Aryl" refers to a hydrocarbon ring system radical comprising hydrogen, 6 to 14 carbon atoms and at least one aromatic ring. For purposes of this invention, the aryl radical may be a monocyclic, bicyclic, or tricyclic system and which may include spiro ring systems. An aryl radical is commonly, but not necessarily, attached to the parent molecule via an aromatic ring of the aryl radical. For purposes of this invention, an "aryl" radical as defined herein can not contain rings having more than 7 members and cannot contain rings wherein two non-adjacent ring atoms thereof are connected through an atom or a group of atoms (i.e., a bridged ring system). Aryl radicals include, but are not limited to, aryl radicals derived from acenaphthylene, anthracene, azulene, benzene, 6,7,8,9-tetrahydro-5H-benzo[7]annulene, fluorene, as-indacene, s-indacene, indane, indene, naphthalene, phenalene, and phenanthrene.

"Optionally substituted aryl" refers to an aryl radical, as defined above, which is optionally substituted by one or more substituents selected from the group consisting of alkyl, alkenyl, alkynyl, halo, haloalkyl, haloalkenyl, haloalkynyl, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{21}$—$OR^{20}$, —$R^{21}$—OC(O)—$R^{20}$, —$R^{21}$—N($R^{20}$)$_2$, —$R^{21}$—C(O)$R^{20}$, —$R^{21}$—C(O)$OR^{20}$, —$R^{21}$—C(O)N($R^{20}$)$_2$, —$R^{21}$—O—$R^{22}$—C(O)N($R^{20}$)$_2$, —$R^{21}$—N($R^{20}$)C(O)$OR^{20}$, —$R^{21}$—N($R^{20}$)C(O)$R^{20}$, —$R^{21}$—N($R^{20}$)S(O)$_2R^{20}$, —$R^{21}$—C(=N$R^{20}$)N($R^{20}$)$_2$, —$R^{21}$—S(O)$_t$$R^{20}$ (where t is 1 or 2), —$R^{21}$—S(O)$_p$$R^{20}$ (where p is 0, 1 or 2), and —$R^{21}$—S(O)$_2$N($R^{20}$)$_2$, where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl, each $R^{21}$ is independently a direct bond or a straight or branched alkylene or alkenylene chain, and $R^{22}$ is a straight or branched alkylene or alkenylene chain.

"Aralkyl" refers to a radical of the formula —$R_b$—$R_c$ where $R_b$ is an alkylene chain as defined above and $R_c$ is one or more aryl radicals as defined above, for example, benzyl and diphenylmethyl.

"Optionally substituted aralkyl" refers to an aralkyl radical, as defined above, wherein the alkylene chain of the aralkyl radical is an optionally substituted alkylene chain, as defined above, and each aryl radical of the aralkyl radical is an optionally substituted aryl radical, as defined above.

"Aralkenyl" refers to a radical of the formula —$R_d$—$R_e$ where $R_d$ is an alkenylene chain as defined above and $R_e$ is one or more aryl radicals as defined above.

"Optionally substituted aralkenyl" refers to an aralkenyl radical, as defined above, wherein the alkenylene chain of the aralkenyl radical is an optionally substituted alkenylene chain, as defined above, and each aryl radical of the aralkenyl radical is an optionally substituted aryl radical, as defined above.

"Aralkynyl" refers to a radical of the formula —$R_e$$R_c$ where $R_e$ is an alkynylene chain as defined above and $R_c$ is one or more aryl radicals as defined above.

"Optionally substituted aralkynyl" refers to an aralkynyl radical, as defined above, wherein the alkynylene chain of the aralkynyl radical is an optionally substituted alkynylene chain, as defined above, and each aryl radical of the aralkynyl radical is an optionally substituted aryl radical, as defined above.

"Cycloalkyl" refers to a stable non-aromatic monocyclic or polycyclic hydrocarbon radical consisting solely of carbon and hydrogen atoms, which includes fused, spiro or bridged ring systems, having from three to fifteen carbon atoms, preferably having from three to ten carbon atoms, more preferably from five to seven carbons and which is saturated or unsaturated and attached to the rest of the molecule by a single bond. For purposes of this invention, a bridged ring system is a system wherein two non-adjacent ring atoms thereof are connected through an atom or a group of atoms, wherein the atom or the group of atoms are the bridging element. An example of a bridged cycloalkyl (monovalent) radical is norbornanyl (also called bicyclo[2.2.1]heptanyl). For purposes of this invention, a non-bridged ring system is a system which does not contain a bridging element, as described above. For purposes of this invention, a fused ring system is a system wherein two adjacent ring atoms thereof are connected through an atom or a group of atoms. An example of a fused cycloalkyl (monovalent) radical is decahydronaphthalenyl (also called decalinyl). For purposes of this invention, a spiro ring system is a system wherein two rings are joined via a single carbon (quaternary) atom. An example of a Spiro cycloalkyl (monovalent) radical is spiro[5.5]undecanyl. Monocyclic cycloalkyl radicals do not include spiro, fused or bridged cycloalkyl radicals, but do include for example, cyclopropyl, cyclobutyl, cyclopentyl, cyclohexyl, cycloheptyl, and cyclooctyl. Polycyclic radicals include fused, spiro or bridged cycloalkyl radicals, for example, $C_{10}$ radicals such as adamantanyl (bridged) and decalinyl (fused), and $C_7$ radicals such as bicyclo[3.2.0]heptanyl (fused), norbornanyl and norbornenyl (bridged), as well as substituted polycyclic radicals, for example, substituted $C_7$ radicals such as 7,7-dimethylbicyclo[2.2.1]heptanyl (bridged).

"Optionally substituted cycloalkyl" refers to a cycloalkyl radical, as defined above, which is optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{21}$—$OR^{20}$, —$R^{21}$—OC(O)—$R^2$, —$R^{21}$—N($R^{20}$)$_2$, —$R^{21}$—C(O)$R^2$, —$R^{21}$—C(O)$OR^{20}$, —$R^{21}$—C(O)N($R^{20}$)$_2$, —$R^{21}$—N($R^{20}$)C(O)$OR^{20}$, —$R^{21}$—N($R^{20}$)C(O)$R^{20}$, —$R^{21}$—N($R^{20}$)S(O)$_2R^{20}$, —$R^{21}$—C(=N$R^{20}$)N($R^{20}$)$_2$, —$R^{21}$—S(O)$_t$$OR^{20}$ (where t is 1 or 2), —$R^{21}$—S(O)$_p$$R^{20}$ (where p is 0, 1 or 2), and —$R^{21}$—S(O)$_2$N($R^2$)$_2$, where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl, and each $R^{21}$ is independently a direct bond or a straight or branched alkylene or alkenylene chain.

"Cycloalkylalkyl" refers to a radical of the formula —$R_b$$R_g$, where $R_b$ is an alkylene chain as defined above and $R_g$ is a cycloalkyl radical as defined above.

"Optionally substituted cycloalkylalkyl" refers to a cycloalkylalkyl radical, as defined above, wherein the alkylene chain of the cycloalkylalkyl radical is an optionally substituted alkylene chain, as defined above, and the cycloalkyl radical of the cycloalkylalkyl radical is an optionally substituted cycloalkyl radical, as defined above.

"Cycloalkylalkenyl" refers to a radical of the formula —$R_d R_g$ where $R_d$ is an alkenylene chain as defined above and $R_g$ is a cycloalkyl radical as defined above.

"Optionally substituted cycloalkylalkenyl" refers to a cycloalkylalkenyl radical, as defined above, wherein the alkenylene chain of the cycloalkylalkenyl radical is an optionally substituted alkenylene chain, as defined above, and the cycloalkyl radical of the cycloalkylalkenyl radical is an optionally substituted cycloalkyl radical as defined above.

"Cycloalkylalkynyl" refers to a radical of the formula —$R_e R_g$ where $R_e$ is an alkynylene radical as defined above and $R_g$ is a cycloalkyl radical as defined above.

"Optionally substituted cycloalkylalkynyl" refers to a cycloalkylalkynyl radical, as defined above, wherein the alkynylene chain of the cycloalkylalkynyl radical is an optionally substituted alkynylene chain, as defined above, and the cycloalkyl radical of the cycloalkylalkynyl radical is an optionally substituted cycloalkyl radical as defined above.

"Halo" refers to bromo, chloro, fluoro or iodo.

"Haloalkyl" refers to an alkyl radical, as defined above, that is substituted by one or more halo radicals, as defined above, for example, trifluoromethyl, difluoromethyl, trichloromethyl, 2,2,2-trifluoroethyl, 1-fluoromethyl-2-fluoroethyl, 3-bromo-2-fluoropropyl, and 1-bromomethyl-2-bromoethyl.

"Haloalkenyl" refers to an alkenyl radical, as defined above, that is substituted by one or more halo radicals, as defined above.

"Haloalkynyl" refers to an alkynyl radical, as defined above, that is substituted by one or more halo radicals, as defined above.

"Heterocyclyl" refers to a stable 3- to 18-membered non-aromatic ring system radical which comprises one to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include spiro or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of a bridged heterocyclyl include, but are not limited to, azabicyclo[2.2.1]heptanyl, diazabicyclo[2.2.1]heptanyl, diazabicyclo[2.2.2]octanyl, diazabicyclo[3.2.1]octanyl, diazabicyclo[3.3.1]nonanyl, diazabicyclo[3.2.2]nonanyl and oxazabicyclo[2.2.1]heptanyl. A "bridged N-heterocyclyl" is a bridged heterocyclyl containing at least one nitrogen, but which optionally contains up to four additional heteroatoms selected from O, N and S. For purposes of this invention, a non-bridged ring system is a system wherein no two non-adjacent ring atoms thereof are connected through an atom or a group of atoms. Examples of heterocyclyl radicals include, but are not limited to, dioxolanyl, 1,4-diazepanyl, decahydroisoquinolyl, imidazolinyl, imidazolidinyl, isothiazolidinyl, isoxazolidinyl, morpholinyl, octahydroindolyl, octahydroisoindolyl, octahydro-1H-pyrrolo[3,2-c]pyridinyl, octahydro-1H-pyrrolo[2,3-c]pyridinyl, octahydro-1H-pyrrolo[2,3-b]pyridinyl, octahydro-1H-pyrrolo[3,4-b]pyridinyl, octahydropyrrolo[3,4-c] pyrrolyl, octahydro-1H-pyrido[1,2-a]pyrazinyl, 2-oxopiperazinyl, 2-oxopiperidinyl, 2-oxopyrrolidinyl, oxazolidinyl, 3,7-diazabicyclo[3.3.1]nonan-3-yl, piperidinyl, piperazinyl, 4-piperidonyl, pyrrolidinyl, pyrazolidinyl, quinuclidinyl, thiazolidinyl, tetrahydrofuranyl, thienyl[1,3]dithianyl, trithianyl, tetrahydropyranyl, thiomorpholinyl, thiamorpholinyl, 1-oxo-thiomorpholinyl, 1,1-dioxo-thiomorpholinyl, azetidinyl, octahydropyrrolo[3,4-c]pyrrolyl, octahydropyrrolo[3,4-b]pyrrolyl, decahydroprazino[1,2-a]azepinyl, azepanyl, azabicyclo[3.2.1]octyl, and 2,7-diazaspiro[4.4]nonanyl.

"Optionally substituted heterocyclyl" refers to a heterocyclyl radical, as defined above, which is optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{21}$—$OR^{20}$, —$R^{21}$—$OC(O)$—$R^{20}$, —$R^{21}$—$N(R^{20})_2$, —$R^2$—$C(O)R^{20}$, —$R^{21}$—$C(O)OR^{20}$, —$R^{21}$—$C(O)N(R^{20})_2$, —$R^{21}$—$N(R^{20})C(O)OR$, —$R^{21}$—$N(R^{20})C(O)R^{20}$, —$R^{21}$—$N(R^2)S(O)_2 R^{20}$, —$R^{21}$—$C(=NR^{20})N(R^{20})_2$, —$R^{21}$—$S(O)_t OR^{20}$ (where t is 1 or 2), —$R^{21}$—$S(O)_p R^{20}$ (where p is 0, 1 or 2), and —$R^{21}$—$S(O)_2 N(R^{20})_2$, where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl, and each $R^{21}$ is independently a direct bond or a straight or branched alkylene or alkenylene chain.

"N-heterocyclyl" refers to a heterocyclyl radical as defined above containing at least one nitrogen and where the point of attachment of the N-heterocyclyl radical to the rest of the molecule may be through a nitrogen atom in the N-heterocyclyl radical or through a carbon in the N-heterocyclyl radical.

"Optionally substituted N-heterocyclyl" refers to an N-heterocyclyl, as defined above, which is optionally substituted by one or more substituents as defined above for optionally substituted heterocyclyl.

"Heterocyclylalkyl" refers to a radical of the formula —$R_b R_h$ where $R_b$ is an alkylene chain as defined above and $R_h$ is a heterocyclyl radical as defined above, and when the heterocyclyl is a nitrogen-containing heterocyclyl, the heterocyclyl may be attached to the alkylene chain at the nitrogen atom.

"Optionally substituted heterocyclylalkyl" refers to a heterocyclylalkyl radical, as defined above, wherein the alkylene chain of the heterocyclylalkyl radical is an optionally substituted alkylene chain, as defined above, and the heterocyclyl radical of the heterocyclylalkyl radical is an optionally substituted heterocyclyl radical, as defined above.

"Heterocyclylalkenyl" refers to a radical of the formula —$R_dR_h$ where $R_d$ is an alkenylene chain as defined above and $R_h$ is a heterocyclyl radical as defined above, and when the heterocyclyl is a nitrogen-containing heterocyclyl, the heterocyclyl may be attached to the alkenylene chain at the nitrogen atom.

"Optionally substituted heterocyclylalkenyl" refers to a heterocyclylalkenyl radical, as defined above, wherein the alkenylene chain of the heterocyclylalkenyl radical is an optionally substituted alkenylene chain, as defined above, and the heterocyclyl radical of the heterocyclylalkenyl radical is an optionally substituted heterocyclyl radical, as defined above.

"Heterocyclylalkynyl" refers to a radical of the formula —$R_eR_h$ where $R_e$ is an alkynylene chain as defined above and $R_h$ is a heterocyclyl radical as defined above, and when the heterocyclyl is a nitrogen-containing heterocyclyl, the heterocyclyl may be attached to the alkynylene chain at the nitrogen atom.

"Optionally substituted heterocyclylalkynyl" refers to a heterocyclylalkynyl radical, as defined above, wherein the alkynylene chain of the heterocyclylalkynyl radical is an optionally substituted alkynylene chain, as defined above, and the heterocyclyl radical of the heterocyclylalkynyl radical is an optionally substituted heterocyclyl radical, as defined above.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. A heteroaryl radical is commonly, but not necessarily, attached to the parent molecule via an aromatic ring of the heteroaryl radical. For purposes of this invention, the heteroaryl radical may be a monocyclic, bicyclic or tricyclic ring system, which may include spiro or bridged ring systems; and the nitrogen, carbon or sulfur atoms in the heteroaryl radical may be optionally oxidized and the nitrogen atom may be optionally quaternized. For purposes of this invention, the aromatic ring of the heteroaryl radical need not contain a heteroatom, as long as one ring of the heteroaryl radical contains a heteroatom. For example benzo-fused heterocyclyls such as 1,2,3,4-tetrahydroisoquinolin-7-yl are considered a "heteroaryl" for the purposes of this invention. Except for the polycyclic heteroaryls containing more than 14 ring atoms, as defined below, a "heteroaryl" radical as defined herein can not contain rings having more than 7 members and cannot contain rings wherein two non-adjacent members thereof are connected through an atom or a group of atoms (i.e., a bridged ring system). Examples of heteroaryl radicals include, but are not limited to, azepinyl, acridinyl, benzimidazolyl, benzindolyl, 1,3-benzodioxolyl, benzofuranyl, benzoxazolyl, benzothiazolyl, benzothiadiazolyl, benzo[b][1,4]dioxepinyl, benzo[b][1,4]oxazinyl, benzo[b]azepinyl, 1,4-benzodioxanyl, benzonaphthofuranyl, benzoxazolyl, benzodioxolyl, benzodioxinyl, benzopyranyl, benzopyranoniyl, benzopuranyl, benzofurmnonyl, benzothienyl (benzothiophenyl), benzothieno[3,2-d]pyrimiidinyl, benzotriazolyl, benzo[4,6]imidazo[1,2-a]pyridinyl, carbazolyl, cinnolinyl, cyclopenta[d]pyrimidinyl, 3,4-dihydro-2H-benzo[b][1,4]dioxepinyl, cyclopenta[4,5]thieno[2,3-d]pyrimidinyl such as 6,7-dihydro-5H-cyclopenta[4,5]thieno[2,3-d]pyrimidinyl, 5,6-dihydrobenzo[h]quinazolinyl, 3,4-dihydro-2H-benzo[b][1,4]thiazinyl, 5,6-dihydrobenzo[h]cinnolinyl, 7',8'-dihydro-5'H-spiro[[1,3]dioxolane-2,6'-quinoline]-3'-yl, 6,7-dihydro-5H-benzo[6,7]cyclohepta[1,2-c]pyridazinyl, 2,3-dihydro-1H-pyrido[2,3-b][1,4]oxazinyl, 3',4'-dihydrospiro[cyclobutane-1,2'-pyrido[3,2-b][1,4]oxazinyl, dihydropyridooxazinyl such as 3,4-dihydro-2H-pyrido[3,2-b][1,4]oxazinyl, dihydropyridothiazinyl such as 3,4-diihydro-2H-pyrido[3,2-b][1,4]thiazinyl, dibenzofuranyl, dibenzothiophenyl, furanyl, furanonyl, furo[3,2-c]pyridinyl, furopyrimidinyl, furopyridazinyl, furopyrazinyl, isothiazolyl, imidazolyl, imidazopyrimidinyl, imidazopyridazinyl, imidazopyrazinyl, imidazo[1,2-a]pyridinyl, indazolyl, indolyl, indazolyl, isoindolyl, indolinyl, isoindolinyl, isoquinolinyl (isoqjuinolyl), indolizinyl, isoxazolyl, naphthyridinyl, 1,6-naphthyridinonyl, oxadiazolyl, 2-oxoazepinyl, oxazolyl, oxiranyl, 5,6,6a,7,8,9,10,19a-octahydrobenzo[h]quinazolinyl, 3'-oxo-3',4'-dihydrospiro[cyclobutane-1,2'-pyrido[3,2-b][1,4]oxazine]yl, 7-oxo-5,6,7,8-tetrahydro-1,8-naphthyridinyl, 1-phenyl-1H-pyrrolyl, phenazinyl, phenothiazinyl, phenoxazinyl, phthalazinyl, phenanthridinyl, pteridinyl, purinyl, pyrrolyl, pyrazolyl, pyrazolo[3,4-d]pyrimidinyl, pyridinyl (pyridyl), pyrido[3,2-d]pyrimidinyl, pyrido[3,4-d]pyrimidinyl, pyrazinyl, pyrimidinyl, pyridazinyl (pyridazyl), pyrrolyl, pyrrolopyrimidinyl, pyrrolopyridazinyl, pyrrolopyrazinyl, 2H-pyrido[3,2-b][1,4]oxazinonyl, 1H-pyrido[2,3-b][1,4]oxazinonyl, pyrrolopyridinyl such as 1H-pyrrolo[2,3-b]pyridinyl, quinazolinyl, quinoxalinyl, quinolinyl, quinuclidinyl, tetrahydroquinolinyl, 5,6,7,8-tetrahydroquinazolinyl, 2,3,4,5-tetrahydrobenzo[b]oxepinyl, 6,7,8,9-tetrahydro-5H-cyclohepta[b]pyridinyl, 6,7,8,9-tetrahydro-5H-pyrido[3,2-c]azepinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimiidinyl, 5,6,7,8-tetrahydropyrido[4,5-c]pyridazinyl, thiazolyl, thiadiazolyl, triazolyl, tetrazolyl, 1,2,3,4-tetrahydroisoquinolin-7-yl, triazinyl, thieno[2,3-d]pyrimidinyl, thienopyrimidinyl (e.g., thieno[3,2-d]pyrimidinyl), thieno[2,3-c]pyridinyl, thienopyridazinyl, thienopyrazinyl, and thiophenyl (thienyl).

"Optionally substituted heteroaryl" refers to a heteroaryl radical, as defined above, which is optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{21}$—$OR^{20}$, —$R^{21}$—$OC(O)$—$R^{20}$, —$R^{21}$—$N(R^{20})_2$, —$R^{21}$—$C(O)R^{20}$, —$R^{21}$—$C(O)OR^{20}$, —$R^{21}$—$C(O)N(R^{20})_2$, —$R^{21}$—$N(R^{20})C(O)OR^{20}$, —$R^{21}$—$N(R^{20})C(O)R^{20}$, —$R^{21}$—$N(R)S(O)_2R^{20}$, —$R^{21}$—$C(=NR^{20})N(R^{20})_2$, —$R^{21}$—$S(O)_tOR^{20}$ (where t is 1 or 2), —$R^{21}$—$S(O)_pR^2$ (where p is 0, 1 or 2), and —$R^{21}$—$S(O)_2N(R^{20})_2$, where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, form an optionally substituted N-heterocyclyl or an optionally substituted N-heteroaryl, and each $R^{21}$ is independently a direct bond or a straight or branched alkylene or alkenylene chain.

"N-heteroaryl" refers to a heteroaryl radical as defined above containing at least one nitrogen and where the point of attachment of the N-heteroaryl radical to the rest of the molecule may be through a nitrogen atom in the N-heteroaryl radical or through a carbon atom in the N-heteroaryl radical.

"Optionally substituted N-heteroaryl" refers to an N-heteroaryl, as defined above, which is optionally substituted by one or more substituents as defined above for optionally substituted heteroaryl.

"Polycyclic heteroaryl containing more than 14 ring atoms" refers to a 15- to 20-membered ring system radical comprising hydrogen atoms, one to fourteen carbon atoms, one to eight heteroatoms selected from the group consisting of nitrogen, oxygen and sulfur, and at least one aromatic ring. A "polycyclic heteroaryl containing more than 14 ring atoms" radical is commonly, but not necessarily, attached to the parent molecule via an aromatic ring of the "polycyclic heteroaryl containing more than 14 ring atoms" radical. For purposes of this invention, the "polycyclic heteroaryl containing more than 14 ring atoms" radical may be a bicyclic, tricyclic or tetracyclic ring system, which may include fused or spiro ring systems; and the nitrogen, carbon or sulfur atoms in the "polycyclic heteroaryl containing more than 14 ring atoms" radical may be optionally oxidized and the nitrogen atom may also be optionally quaternized. For purposes of this invention, the aromatic ring of the "polycyclic heteroaryl containing more than 14 ring atoms" radical need not contain a heteroatom, as long as one ring of the "polycyclic heteroaryl containing more than 14 ring atoms" radical contains a heteroatom. Examples of "polycyclic heteroaryl containing more than 14 ring atoms" radicals include, but are not limited to, 6,7-dihydro-5H-benzo[6,7]cyclohepta[1,2-c]pyridazin-3-yl, 6,7-dihydro-5H-pyrido[2',3':6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl.

"Optionally substituted polycyclic heteroaryl containing more than 14 ring atoms" is meant to include "polycyclic heteroaryl containing more than 14 ring atoms" radicals, as defined above, which are optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^{21}-OR^{20}$, $-R^{21}-OC(O)-R^{20}$, $-R^{21}-N(R^{20})_2$, $-R^{21}-C(O)R^{20}$, $-R^{21}-C(O)OR^{20}$, $-R^2-C(O)N(R^{20})_2$, $-R^{21}-N(R^{20})C(O)OR^{20}$, $-R^{21}-N(R^{20})C(O)R^{20}$, $-R^{21}-N(R^{20})S(O)_tR^{20}$ (where t is 1 or 2), $-R^{21}-S(O)_tOR^{20}$ (where t is 1 or 2), $-R^{21}-S(O)_pR^{20}$ (where p is 0, 1 or 2), and $-R^{21}-S(O)_tN(R^{20})_2$ (where t is 1 or 2), where each $R^{20}$ is independently selected from the group consisting of hydrogen, alkyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{20}$'s, together with the common nitrogen to which they are both attached, may optionally form an optionally substituted N-heterocyclyl or an optionally substituted N-heteroaryl, and each $R^{21}$ is independently a direct bond or a straight or branched alkylene or alkenylene chain.

"Heteroarylalkyl" refers to a radical of the formula $-R_bR_i$ where $R_b$ is an alkylene chain as defined above and $R_i$ is a heteroaryl radical as defined above, and when the heteroaryl is a nitrogen-containing heteroaryl, the heteroaryl may be attached to the alkylene chain at the nitrogen atom.

"Optionally substituted heteroarylalkyl" refers to a heteroarylalkyl radical, as defined above, wherein the alkylene chain of the heteroarylalkyl radical is an optionally substituted alkylene chain, as defined above, and the heteroaryl radical of the heteroarylalkyl radical is an optionally substituted heteroaryl radical, as defined above.

"Heteroarylalkenyl" refers to a radical of the formula $-R_dR_i$ where $R_d$ is an alkenylene chain as defined above and $R_i$ is a heteroaryl radical as defined above, and when the heteroaryl is a nitrogen-containing heteroaryl, the heteroaryl may be attached to the alkenylene chain at the nitrogen atom.

"Optionally substituted heteroarylalkenyl" refers to a heteroarylalkenyl radical, as defined above, wherein the alkenylene chain of the heteroarylalkenyl radical is an optionally substituted alkenylene chain, as defined above, and the heteroaryl radical of the heteroarylalkenyl radical is an optionally substituted heteroaryl radical, as defined above.

"Heteroarylalkynyl" refers to a radical of the formula $-R_eR_i$ where $R_e$ is an alkynylene chain as defined above and $R_i$ is a heteroaryl radical as defined above, and when the heteroaryl is a nitrogen-containing heteroaryl, the heteroaryl may be attached to the alkynylene chain at the nitrogen atom.

"Optionally substituted heteroarylalkynyl" refers to a heteroarylalkynyl radical, as defined above, wherein the alkynylene chain of the heteroarylalkynyl radical is an optionally substituted alkynylene chain, as defined above, and the heteroaryl radical of the heteroarylalkynyl radical is an optionally substituted heteroaryl radical, as defined above.

"Hydroxyalkyl" refers to an alkyl radical as defined above which is substituted by one or more hydroxy radicals (—OH).

Certain chemical groups named herein may be preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

"Stable compound" and "stable structure" are meant to indicate a compound that is sufficiently robust to survive isolation to a useful degree of purity from a reaction mixture, and formulation into an efficacious therapeutic agent.

"Patient" means a mammal who has been diagnosed as having cancer and/or metastatic cancer, or who is predisposed to having metastatic cancer due to having cancer.

"Mammal" means any vertebrate of the class Mammalia. Humans and domestic animals, such as cats, dogs, swine, cattle, sheep, goats, horses, rabbits, and the like are a particular focus. Preferably, for purposes of this invention, the mammal is a primate (e.g., monkey, baboon, chimpanzee and human), and more preferably, the mammal is a human.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. However, when a first functional group is described as "optionally substituted," and in turn, substituents on the first functional group are also "optionally substituted" and so forth, for the purposes of this invention, such iterations for a radical to be optionally substituted are limited to three. Thus, groups described as substituents on the third iteration are not themselves optionally substituted. For example, if an R group herein is defined as being "optionally substituted aryl" (the first iteration) and the optional substituents for the "optionally substituted aryl" include "optionally substituted heteroaryl" (the second iteration) and the optional substituents for the "optionally substituted heteroaryl" include "optionally substituted cycloalkyl" (the third iteration), the optional substituents on the cycloalkyl can not be optionally substituted.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by a regulatory body (e.g. the United States Food and Drug Administration) as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfonic acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, and undecylenic acid.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, and aluminum salts. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

An "anti-Axl antibody" refers to an antibody which provides inhibition of Axl activity.

Preferably, the anti-Axl antibody is an antibody as described in any of the following references: UK patent application 1422605.4, international patent application PCT/EP2015/063700, international patent application PCT/EP2015/063704, European patent publication EP2267454, international patent publication WO 2009063965, international patent publication WO 2011159980, European patent publication EP2228392, international patent publication WO 2012175691, international patent publication WO 2012175692, international patent publication WO 2009062690, and international patent publication WO 2010130751 (the contents of each of which is hereby incorporated by reference).

For example, in one embodiment, the anti-Axl antibody is an antibody as described in UK patent application 1422605.4, the contents of which is hereby incorporated by reference, particularly as shown at pages 93-96.

In another embodiment, the anti-Axl antibody is an antibody as described in international patent application PCT/EP2015/063700, the contents of which is hereby incorporated by reference, particularly as shown at pages 82-83.

In another embodiment, the anti-Axl antibody is an antibody as described in international patent application PCT/EP2015/063704, the contents of which is hereby incorporated by reference, particularly as shown at pages 72-73.

In another embodiment, the anti-Axl antibody is an antibody as described in European patent publication EP2267454, the contents of which is hereby incorporated by reference.

In another embodiment, the anti-Axl antibody is an antibody as described in European patent publication EP 2228392A1, the contents of which is hereby incorporated by reference, particularly as shown at pages 31-33.

In another embodiment, the anti-Axl antibody is an antibody as described in US patent publication US 2012/0121587 A1, the contents of which is hereby incorporated by reference, particularly as shown at pages 26-61.

In another embodiment, the anti-Axl antibody is an antibody as described in international patent publication WO 2011159980, the contents of which is hereby incorporated by reference, particularly as shown in FIG. 2, Figure page 6 (of 24).

In another embodiment, the anti-Axl antibody is an antibody as described in international patent publication WO 2012175691, the contents of which is hereby incorporated by reference, particularly as shown at page 5.

In another embodiment, the anti-Axl antibody is an antibody as described in international patent publication WO 2012175692, the contents of which is hereby incorporated by reference, particularly as shown at pages 4-5.

In another embodiment, the anti-Axl antibody is an antibody as described in international patent publication WO 2009062690, the contents of which is hereby incorporated by reference.

In another embodiment, the anti-Axl antibody is an antibody as described in international patent publication WO 2010130751, the contents of which is hereby incorporated by reference, particularly as shown at Figure pages 1-17 (of 78).

Preferably, the anti-Axl antibody is an antibody as described in UK patent application 1422605.4, international patent application PCT/EP2015/063700, international patent application PCT/EP2015/063704, or international patent publication WO 2011159980.

An "oncolytic virus" refers to a virus that preferentially infects and lyses cancer or tumour cells as compared to normal cells. Cytotoxic/oncolytic activity of the virus may be present, observed or demonstrated in vitro, in vivo, or both. Preferably, the virus exhibits cytotoxic/oncolytic activity in vivo.

The oncolytic virus includes virsues with natural tumour selection such as reovirus, Newcastle disease virus (NDV), adenovirus, herpes virus (e.g. herpes simplex 1), polio virus, mumps virus, measles virus, influenza virus, vaccinia virus, rhabdovirus, parvovirus, vesicular stomatitis virus, and derivatives and variants thereof which preferentially infect and lyse cancer or tumour cells as compared to normal cells, preferably Newcastle disease virus, reovirus, autonomous parvovirus, vesicular stomatitis virus, and herpes simplex 1 virus, and derivatives and variants thereof. Particularly, Newcastle disease virus, reovirus, autonomous parvovirus and vesicular stomatitis virus, as described in Everts et al. Cancer Gene Therapy, 2005, 12, 141-161, and shown in Table A (preferably Newcastle disease virus).

TABLE A

| Virus | Class, Subclass | Genetic/phenotypic target within tumors |
|---|---|---|
| NDV | ssRNA−, rhabdovirus | Activated ras-pathway; defective IFN-pathway |
| Reovirus | dsRNA, reovirus | Activated ras-pathway |
| Autonomous parvovirus | ssDNA, parvovirus | IFN-resistance of tumors |
| VSV | ssRNA−, rhabdovirus | Loss of cell cycle control? |

NDV, Newcastle disease virus; VSV, vesicular stomatitis virus; IFN, interferon; ds, double stranded; ss, single-stranded; ssRNA, RNA as a template for mRNA.

The oncolytic virus also includes virsues with gene deletions to achieve tumour-selective replication, as shown in Table B, and viruses produced using tissue- and tumour-specific promoters for tumour-selective replication, as shown in Table C (as described in Everts et al. Cancer Gene Therapy, 2005, 12, 141-161).

TABLE B

| Parental strain | Agent | Genetic alteration | Genetic/phenotypic target within tumours |
|---|---|---|---|
| Adenovirus | ONYX-015 | E1B-55kd deletion | p53 null/mutant or/and inactivated p53-pathway |
| | Ad-A24 | E1A CR2 deletion | pRb null/mutant or/and loss of cell cycle control |
| | CB-1 | E1A CR2 deletion; E1B-55kd deletion | pRb and p53 defective pathways errand loss of cell cycle control |
| | d22-947 | E1A CR2 deletion | pRb null/mutant or/and loss of cell cycle control |
| | dl331 | VA-I gene deletion | Ras-activated pathway |
| Herpes simplex virus-1 | dlsptk | Thymidine kinase gene deletion | Replication |
| | R3616 | Delation of both γ34.5 genes | Loss of neurovirulence |
| | HrR3 | ICP6 gene deletion | Replication |
| | G207 | Deletion of both γ34.5 genes; ribonucleotide reductase disruption | Replication; loss of neurovirulence |
| | NV1020 | Deletion of one γ34.5 gene; delation in tk gene; insertion of exogenous copy of tk gene | Replication, loss of neurovirulence |
| Vaccinia virus | VV-TK | Thymidine kinase gene deletion | Replication |
| | VV-SPI-1/2 | Deletion of SPI-1 and SPI-2 genes | Replication |
| | WDD | Thymidine kinase gene deletion; deletion of VGF gene | Replication |
| Polio virus | PV1(RIPO) | IRES element replaced by IRES from HRV2 | Loss of neurovirulence; replication |
| Influenza virus | IVA-NS1 | NS1 gene deletion | IFN-pathway deficiency | tk, thymidine kinase: IRES, internal ribosomal entry site; HRV2, human rhinovirus type 2: IFN, interferon.

TABLE C

| Promoter | Tissue-tumour type | Applied virus |
|---|---|---|
| Osteocalcin promoter | Osteosarcoma | Adenovirus |
| PSA promoter | Prostate | Adenovirus |
| AFP promoter | Hepatocellular carcinoma | Adenovirus |
| Tyrosinase promoter | Melanocytes | Adenovirus |
| MUC-1 promoter | Breast carcinomas | Adenovirus HSV-1 |
| Midkine differentation factor promoter | Neuroblastoma | Adenovirus |
| Rat probasin promoter | Prostate | Adenovirus |
| Leukoprotease inhibitor promoter | Ovarian carcinoma | Adenovirus |
| Tcf responsive promoter | Colon cancer | Adenovirus Autonomous parvovirus |

TABLE C-continued

| Promoter | Tissue-tumour type | Applied virus |
|---|---|---|
| Calponin promoter | Smooth muscle cells | HSV-1 |
| Albumin enhancer-promoter | Liver | HSV-1 |
| Flt-1 promoter | Teratocarcinoma | Adenovirus |
| E2F-1 promoter | Cancer cells in general | Adenovirus |
| Telomerase reverse transcriptase promoter | Cancer cells in general | Adenovirus |
| Hypoxia responsive elements | Cancer cells in general | Adenovirus |

PSA, prostate-specific antigen; AFP, α-fetoprotein; Flt-1, vascular endothelial growth factor receptor type 1; HSV-1, herpes simplex virus-1.

A "derivative" or "variant" of a virus refers to a virus (i) obtained by selecting the virus under different growth conditions, (ii) one that has been subjected to a range of selection pressures, (iii) one that has been genetically modified using recombinant techniques known in the art, or any combination thereof.

Possible strategies to improve the intrinsic anti-tumour potency of oncolytic viruses are as described in Everts et al. Cancer Gene Therapy, 2005, 12, 141-161, and shown in Table D.

TABLE D

| Strategy | Example | Way of action | Applied virus (inserted gene) |
|---|---|---|---|
| 1. Insertion of genes encoding cytotoxic proteins | Expression of adenoviral E3 gene coding for adenoviral death protein | Increase of viral-induced cell lysis | Adenovirus (E3) |
| | Expression of syncytium-inducing genes | Increase of cell killing of both infected and uninfected cells through syncytium induction | Adenovirus (FMG) HSV-1 (FMG) |
| | Deletion of apoptosis inhibitor EfB-19kd protein | More efficient cell killing by viral-induced apoptosis | Adenovirus (—) |
| 2. Elicitation of an antitumor immune response | Expression of cytokine genes | Activation and stimulation of tumor-specific cytotoxic T cells | HSV-1 (IL-4) |
| | Use of oncolysates. treatment with virus-augmented tumor cells | Elicitation of an immune response directed against tumor-specific antigens | HSV-1 (IL-12) Vaccinia virus (GM-CSF) Vaccinia virus (IL-2) Parvovirus (MCP-1) Adenovirus (IFN) Vaccinia virus (—) VSV (—) NDV (-) |
| | Expression of tumor-specific antigens | Elicitation of an immune response directed against tumor-specific antigens | Vaccinia virus (CEA) Vaccinia virus (PSA) |

GM-CSF, granulocyte-macrophage colony-stimulating factor; MCP-1, monocyte chemotactic protein 1, FMG, fusogenic membrane glycoprotein; IL, interleukin, CEA, carcinoembryonic antigen.

Specific examples of NDV variants are as described in WO2014/158811, particularly pages 3-10, i.e., Newcastle disease viruses engineered to express an agonist of a co-stimulatory signal of an immune cell. A further specific variant includes a herpes simplex 1 variant known as oncolytic immunotherapy talimogene laherparepvec (T-VEC), which is engineered through the genetic alteration of the herpes simplex 1 virus to secrete the cytokine GM-CSF within the tumour, causing cell lysis.

A "pharmaceutical composition" refers to a formulation of an Axl inhibitor (preferably a compound of formula (I)) and/or a formulation of an immune checkpoint (activity) modulator and a medium generally accepted in the art for the delivery of the biologically active compound to mammals, for example, humans. Such a medium includes all pharmaceutically acceptable carriers, diluents or excipients therefor.

"Therapeutically effective amount" refers to that amount of the therapeutic agent sufficient to destroy, modify, control or remove cancer tissue. A therapeutically effective amount may refer to the amount of therapeutic agents sufficient to delay or minimise the spread of cancer. A therapeutically effective amount may also refer to the amount of the therapeutic agent that provides a therapeutic benefit in the treatment or management of cancer. Further, a therapeutically effective amount with respect to an Axl inhibitor of the combination therapies of the invention means that amount of an Axl inhibitor in combination with one or more immune checkpoint (activity) modulators that provides a therapeutic benefit in the treatment or management of cancer, including the amelioration of symptoms associated with cancer. Used in connection with an amount of an Axl inhibitor, the term can encompass an amount that improves overall therapy, reduces or avoids unwanted effects, or enhances the therapeutic efficacy of and synergises with the one or more immune checkpoint (activity) modulators utilised in the combination therapies of the invention.

"Prophylactically effective amount" refers to that amount of the prophylactic agent sufficient to result in the prevention of cancer. A prophylactically effective amount may refer to the amount of prophylactic agent sufficient to prevent cancer in a patient, including, but not limited to, those patients who are predisposed to cancer or previously exposed to carcinogens. A prophylactically effective amount may also refer to the amount of the prophylactic agent that provides a prophylactic benefit in the prevention of cancer. Further, a prophylactically effective amount with respect to an Axl inhibitor of the combination therapies of the invention means that amount of an Axl inhibitor in combination with one or more immune checkpoint (activity) modulators that provides a prophylactic benefit in the prevention of cancer. Used in connection with an amount of an Axl inhibitor, the term can encompass an amount that improves overall prophylaxis or enhances the prophylactic efficacy of and synergises with the one or more immune checkpoint (activity) modulators.

As used herein, the terms "manage", "managing" and "management" refer to the beneficial effects that a patient derives from a combination therapy of the invention, which does not result in a cure of the cancer. In certain embodiments, a combination therapy of the invention "manages" metastatic cancer so as to prevent the progression or worsening of the cancer.

As used herein, the terms "prevent", "preventing" and "prevention" refer to the prevention of the spread or onset of cancer in a patient.

As used herein, the terms "treat", "treating" and "treatment" refer to the eradication, removal, modification or control of cancer that results from the combination therapy of the invention. In certain embodiments, such terms refer to the minimizing or delay of the spread of cancer.

The compounds of formula (I), or their pharmaceutically acceptable salts, may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

"Atropisomers" are stereoisomers resulting from hindered rotation about single bonds where the barrier to rotation is high enough to allow for the isolation of the conformers (Eliel, E. L.; Wilen, S. H. *Stereochemistry of Organic Compounds*; Wiley & Sons: New York, 1994; Chapter 14). Atropisomerism is significant because it introduces an element of chirality in the absence of stereogenic atoms. The invention is meant to encompass atropisomers, for example in cases of limited rotation around the single bonds emanating from the core triazole structure, atropisomers are also possible and are also specifically included in the compounds of the invention.

The chemical naming protocol and structure diagrams used herein are a modified form of the I.U.P.A.C. nomenclature system wherein the compounds of formula (I) are named herein as derivatives of the central core structure, i.e., the triazole structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

For purposes of this invention, the depiction of the bond attaching the $R^3$ substituent to the parent triazole moiety in formula (I), as shown below:

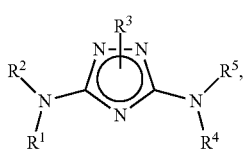

(I)

is intended to include only the two regioisomers shown below, i.e., compounds of formula (Ia) and (Ib):

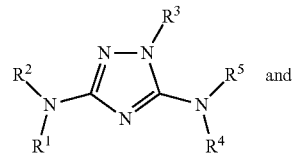

(Ia)

and

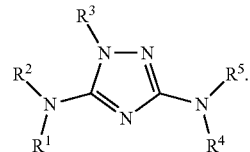

(Ib)

The numbering system of the ring atoms in compounds of formula (Ia) is shown below:

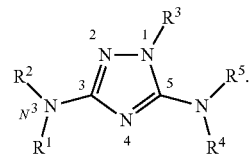

(Ia)

For example, a compound of formula (Ia) wherein $R^1$, $R^4$ and $R^5$ are each hydrogen, $R^2$ is 4-(2-(pyrrolidin-1-yl)ethoxy)phenyl and $R^3$ is 6,7-dihydro-5H-benzo[6,7]cyclohepta[1,2-c]pyridazin-3-yl; i.e., a compound of the following formula:

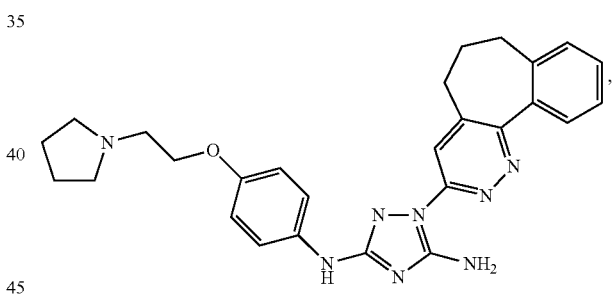

is named herein as 1-(6,7-dihydro-5H-benzo[6,7]cyclohepta[1,2-c]pyridazin-3-yl)-$N^3$-(4-(2-(pyrrolidin-1-yl)ethoxy)phenyl)-1H-1,2,4-triazole-3,5-diamine.

The numbering system of the ring atoms in compounds of formula (Ib) is shown below:

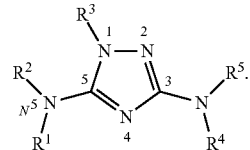

(Ib)

Compounds of formula (Ib) are similarly named herein.

Of the various aspects of the invention, as set forth herein, certain embodiments are preferred.

In one preferred embodiment of the use of the present invention, the compound of formula (I) is a compound of formula (Ia):

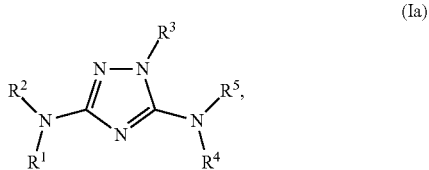

(Ia)

wherein $R^1$, $R^2$, $R^3$, $R^4$ and $R^5$ are as described above for compounds of formula (I), as an isolated stereoisomer or mixture thereof or as a tautomer or mixture thereof, or a pharmaceutically acceptable salt or N-oxide thereof.

Another embodiment is the use where, in the compound of formula (Ia) as set forth above, $R^2$ and $R^3$ are each independently a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—O—$R^{10}$—$OR^8$, —$R^9$—O—$R^{10}$—O—$R^{10}$—$OR^8$, —$R^9$—O—$R^{10}$—CN, —$R^9$—O—$R^{10}$—C(O)$OR^8$, —$R^9$—O—$R^{10}$—C(O)N($R^6$)$R^7$, —$R^9$—O—$R^{10}$—S(O)$_p$$R^8$ (where p is 0, 1 or 2), —$R^9$—O—$R^{10}$—N($R^6$)$R^7$, —$R^9$—O—$R^{10}$—C(N$R^{11}$)N($R^{11}$)H, —$R^9$—OC(O)—$R^8$, —$R^9$—N($R^6$)$R^7$, —$R^9$—C(O)$R^8$, —$R^9$—C(O)$OR^8$, —$R^9$—C(O)N($R^6$)$R^7$, —$R^9$—N($R^6$)C(O)$OR^{12}$, —$R^9$—N($R^6$)C(O)$R^8$, —$R^9$—N($R^6$)S(O)$_t$$R^8$ (where t is 1 or 2), —$R^9$—S(O)$_t$$OR^8$ (where t is 1 or 2), —$R^9$—S(O)$_p$$R^8$ (where p is 0, 1 or 2), and —$R^9$—S(O)$_t$N($R^6$)$R^7$ (where t is 1 or 2); and $R^1$, $R^4$, $R^5$, each $R^6$, each $R^7$, each $R^8$, each $R^9$, each $R^{10}$, each $R^{11}$ and $R^{12}$ are as described above for compounds of formula (Ia).

Another embodiment is the use where, in the compound of formula (Ia) as set forth above:
$R^1$, $R^4$ and $R^5$ are each hydrogen;
each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—CN, —$R^{10}$—$NO_2$, —$R^{10}$—N($R^8$)$_2$, —$R^{10}$—C(O)$OR^8$ and —$R^{10}$—C(O)N($R^8$)$_2$, or any $R^6$ and $R^7$, together with the common nitrogen to which they are both attached, form an optionally substituted N-heteroaryl or an optionally substituted N-heterocyclyl;
each $R^8$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;
each $R^9$ is independently selected from the group consisting of a direct bond and an optionally substituted straight or branched alkylene chain;
each $R^{10}$ is an optionally substituted straight or branched alkylene chain; and each $R^{11}$ is independently selected from the group consisting of hydrogen, alkyl, cyano, nitro and —$OR^8$.

Another embodiment is the method where, in the compound of formula (Ia) as set forth above:
$R^2$ and $R^3$ are each independently a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-pyrido[2',3':6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl,
each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—OC(O)—$R^8$, —$R^9$—N($R^6$)$R^7$, —$R^9$—C(O)$R^8$, —$R^9$—C(O)$OR^8$, —$R^9$—C(O)N($R^6$)$R^7$, —$R^9$—N($R^6$)C(O)$OR^{12}$, —$R^9$—N($R^6$)C(O)$R^8$, —$R^9$—N($R^6$)S(O)$_t$$R^8$ (where t is 1 or 2), —$R^9$—S(O)$_t$$OR^8$ (where t is 1 or 2), —$R^9$—S(O)$_p$$R^8$ (where p is 0, 1 or 2), and —$R^9$—S(O)$_t$N($R^6$)$R^7$ (where t is 1 or 2).

Another embodiment is the use wherein the compound of formula (Ia) is 1-(6,7-dihydro-5H-benzo[6,7]cyclohepta[1,2-c]pyridazin-3-yl)-$N^3$-(5',5'-dimethyl-6,8,9,10-tetrahydro-5H-spiro[cycloocta[b]pyridine-7,2'-[1,3]dioxane]-3-yl)-1H-1,2,4-triazole-3,5-diamine.

Another embodiment is the use where, in the compound of formula (Ia) as set forth above, $R^2$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—O—$R^{10}$—$OR^8$, —$R^9$—O—$R^{10}$—O—$R^{10}$—$OR^8$, —$R^9$—O—$R^{10}$—CN, —$R^9$—O—$R^{10}$—C(O)$OR^8$, —$R^9$—O—$R^{10}$—C(O)N($R^6$)$R^7$, —$R^9$—O—$R^{10}$—S(O)$_p$$R^8$ (where p is 0, 1 or 2), —$R^9$—O—$R^{10}$—N($R^6$)$R^7$, —$R^9$—O—$R^{10}$—C(N$R^{11}$)N($R^{11}$)H, —$R^9$—OC(O)—$R^8$, —$R^9$—N($R^6$)$R^7$, —$R^9$—C(O)$R^8$, —$R^9$—C(O)$OR^8$, —$R^9$—C(O)N($R^6$)$R^7$, —$R^9$—N($R^6$)C(O)$OR^{12}$, —$R^9$—N($R^6$)C(O)$R^8$, —$R^9$—N($R^6$)S(O)$_t$$R^8$ (where t is 1 or 2), —$R^9$—S(O)$_t$$OR^8$ (where t is 1 or 2), —$R^9$—S(O)$_p$$R^8$ (where p is 0, 1 or 2), and —$R^9$—S(O)$_t$N($R^6$)$R^7$ (where t is 1 or 2); $R^3$ is selected from the group consisting of aryl and heteroaryl, where the aryl and the heteroaryl are each independently optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—$OR^{12}$, —$R^{13}$—OC(O)—$R^{12}$, —$R^{13}$—O—$R^{14}$—$N(R^{12})_2$, —$R^{13}$—$N(R^2)$—$R^{14}$—$N(R^{12})_2$, —$R^{13}$—$N(R^{12})_2$, —$R^{13}$—$C(O)R^{12}$, —$R^{13}$—$C(O)OR^{12}$, —$R^{13}$—$C(O)N(R^2)_2$, —$R^{13}$—$C(O)N(R^{12})$—$R^{14}$—$N(R^{12})R^{13}$, —$R^{13}$—$C(O)N(R^{12})$—$R^{14}$—$OR^{12}$, —$R^{13}$—$N(R^{12})C(O)OR^{12}$, —$R^{13}$—$N(R^{12})C(O)R^{12}$, —$R^{13}$—$N(R^{12})S(O)_tR^{12}$ (where t is 1 or 2), —$R^{13}$—$S(O)_tOR^{12}$ (where t is 1 or 2), —$R^{13}$—$S(O)_pR^{12}$ (where p is 0, 1 or 2), and —$R^{13}$—$S(O)_tN(R^{12})_2$ (where t is 1 or 2); and $R^1$, $R^4$, $R^5$, each $R^6$, each $R^7$, each $R^8$, each $R^9$, each $R^{10}$, each $R^{11}$, each $R^{12}$, each $R^{13}$ and each $R^{14}$ are as described above for compounds of formula (Ia).

Another embodiment is the use where, in the compound of formula (Ia) as set forth above:
$R^1$, $R^4$ and $R^5$ are each hydrogen;
each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—CN, —$R^{10}$—$NO_2$, —$R^{10}$—$N(R^8)_2$, —$R^{10}$—$C(O)OR^8$ and —$R^{10}$—C(O)N$(R^8)_2$, or any $R^6$ and $R^7$, together with the common nitrogen to which they are both attached, form an optionally substituted N-heteroaryl or an optionally substituted N-heterocyclyl;
each $R^8$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;
each $R^9$ is independently selected from the group consisting of a direct bond and an optionally substituted straight or branched alkylene chain;
each $R^{10}$ is an optionally substituted straight or branched alkylene chain;
each $R^{11}$ is independently selected from the group consisting of hydrogen, alkyl, cyano, nitro and —$OR^8$;
each $R^{12}$ is independently selected from the group consisting of hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;
each $R^{13}$ is independently selected from the group consisting of a direct bond and an optionally substituted straight or branched alkylene chain; and
each $R^{14}$ is an optionally substituted straight or branched alkylene chain.

Another embodiment is the use where, in the compound of formula (Ia) as set forth above:
$R^1$, $R^4$ and $R^5$ are each hydrogen;
$R^2$ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-pyrido[2',3':6,7]cyclohepta[1,2-c]pyridazin-3-yl, 6,7,8,9-tetrahydro-5H-cyclohepta[4,5]thieno[2,3-d]py- rimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-1-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—OC(O)—$R^8$, —$R^9$—$N(R^6)R^7$, —$R^9$—$C(O)R^8$, —$R^9$—C(O)—$OR^8$, —$R^9$—$C(O)N(R^6)R^7$, —$R^9$—$N(R^6)C(O)OR^{12}$, —$R^9$—$N(R^6)C(O)R^8$, —$R^9$—$N(R^6)S(O)_tR^8$ (where t is 1 or 2), —$R^9$—$S(O)_tOR^8$ (where t is 1 or 2), —$R^9$—$S(O)_pR^8$ (where p is 0, 1 or 2), and —$R^9$—$S(O)_tN(R^6)R^7$ (where t is 1 or 2);
each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—CN, —$R^{10}$—$NO_2$, —$R^{10}$—$N(R^8)_2$, —$R^{10}$—$C(O)OR^8$ and —$R^{10}$—C(O)N$(R^8)_2$, or any $R^6$ and $R^7$, together with the common nitrogen to which they are both attached, form an optionally substituted N-heteroaryl or an optionally substituted N-heterocyclyl;
each $R^8$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroerylalkyl;
each $R^9$ is independently selected from the group consisting of a direct bond and an optionally substituted straight or branched alkylene chain;
each $R^{10}$ is an optionally substituted straight or branched alkylene chain;
each $R^{12}$ is independently selected from the group consisting of hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^2$'s, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is a use where, in the compound of formula (Ia) as set forth above:

$R^2$ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-pyrido[2',3':6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, $-R^9-OR^8$, $-R^9-OC(O)-R^8$, $-R^9-N(R^6)R^7$, $-R^9-C(O)R^8$, $-R^9-C(O)-OR^8$, $-R^9-C(O)N(R^6)R^7$, $-R^9-N(R^6)C(O)OR^{12}$, $-R^9-N(R^6)C(O)R^8$, $-R^9-N(R^6)S(O)_tR^8$ (where t is 1 or 2), $-R^9-S(O)_tOR^8$ (where t is 1 or 2), $-R^9-S(O)_pR^8$ (where p is 0, 1 or 2), and $-R^9-S(O)_tN(R^6)R^7$ (where t is 1 or 2); and $R^3$ is heteroaryl selected from the group consisting of pyridinyl, pyrimidinyl, 4,5-dihydro-1H-benzo[b]azepin-2(3H)-on-8-yl, benzo[d]imidazolyl, 6,7,8,9-tetrahydro-5H-pyrido[3,2-d]azepin-3-yl, 6,7,8,9-tetrahydro-5H-pyrido[3,2-c]azepin-3-yl, 5,6,7,8-tetrahydro-1,6-naphthyridin-3-yl, 5,6,7,8-tetrahydroquinolin-3-yl, 1,2,3,4-tetrahydroisoquinolin-7-yl, 2,3,4,5-tetrahydrobenzo[b]oxepin-7-yl, 3,4-dihydro-2H-benzo[b][1,4]dioxepin-7-yl, benzo[d]oxazol-5-yl, 3,4-dihydro-2H-benzo[b][1,4]oxazin-7-yl, benzo[b]thiophenyl, thieno[3,2-d]pyrimidinyl and 6,7,8,9-tetrahydro-5H-cyclohepta[b]pyridin-3-yl, each optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl, optionally substituted heteroarylalkenyl, $-R^{13}-OR^{12}$, $-R^{13}-OC(O)-R^{12}$, $-R^{13}-O-R^{14}-N(R^{12})_2$, $-R^{13}-N(R^2)_2$, $-R^{13}-C(O)R^{12}$, $-R^{13}-C(O)OR^{12}$, $-R^{13}-C(O)N(R^2)_2$, $-R^{13}-C(O)N(R^2)-R^{14}-N(R^{12})R^{13}$, $-R^{13}-C(O)N(R^{12})-R^{14}-OR^{12}$, $-R^{13}-N(R^{12})C(O)OR^{12}$, $-R^{13}-N(R^{12})C(O)R^{12}$, $-R^{13}-N(R^{12})S(O)_pR^{12}$ (where t is 1 or 2), $-R^{13}-S(O)OR^{12}$ (where t is 1 or 2), $-R^{13}-S(O)_pR^{12}$ (where p is 0, 1 or 2), and $-R^{13}-S(O)_tN(R^{12})_2$ (where t is 1 or 2).

Another embodiment is a use wherein the compound of formula (Ia), as set forth above, is selected from the group consisting of:

1-(6,7-dimethoxy-quinazolin-4-yl)-$N^3$-(5,7,8,9-tetrahydrospiro[cyclohepta[b]pyridine-6,2'-[1,3]dioxolane]-3-yl)-1H-1,2,4-triazole-3,5-diamine;

1-(2-chloro-7-methylthieno[3,2-d]pyrimidin-4-yl)-$N^3$-(5,7,8,9-tetrahydrospiro[cyclohepta[b]pyridine-6,2'-[1,3]dioxolane]-3-yl)-1H-1,2,4-triazole-3,5-diamine;

1-(2-chloro-7-methylthieno[3,2-d]pyrimidin-4-yl)-$N^3$-(5,6,8,9-tetrahydrospiro[cyclohepta[b]pyridine-7,2'-[1,3]dioxolane]-3-yl)-1H-1,2,4-triazole-3,5-diamine; and 1-(2-chloro-7-methylthieno[3,2-d]pyrimidin-4-yl)-$N^3$-(5',5'-dimethyl-6,8,9,10-9tetrahydro-5H-spiro[cycloocta[b]pyridine-7,2'-[1,3]dioxane]-3-yl)-1H-1,2,4-triazole-3,5-diamine.

Another embodiment is the use where, in the compound of formula (Ia) as set forth above, $R^2$ is selected from the group consisting of aryl and heteroaryl, where the aryl and the heteroaryl are each independently optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^{13}-OR^{12}$, $-R^{13}-OC(O)-R^{12}$, $-R^{13}-O-R^{14}-N(R^2)_2$, $-R^{13}-N(R^{12})-R^{14}-N(R^{12})_2$, $-R^{13}-N(R^{12})_2$, $-R^{13}-C(O)R^{12}$, $-R^{13}-C(O)OR^{12}$, $-R^{13}-C(O)N(R^{12})_2$, $-R^{13}-C(O)N(R^{12})-R^{14}-N(R^{12})R^{13}$, $-R^{13}-C(O)N(R^{12})-R^{14}-OR^{12}$, $-R^{13}-N(R^{12})C(O)OR^{12}$, $-R^{13}-N(R^{12})C(O)R^{12}$, $-R^{13}-N(R^{12})S(O)_tR^{12}$ (where t is 1 or 2), $-R^{13}-S(O)_tOR^{12}$ (where t is 1 or 2), $-R^{13}-S(O)_pR^{12}$ (where p is 0, 1 or 2), and $-R^3-S(O)_tN(R^{12})_2$ (where t is 1 or 2); $R^3$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, $-R^9-OR^8$, $-R^9-O-R^{10}-OR^8$, $-R^9-O-R^{10}-O-R^{10}-OR^8$, $-R^9-O-R^{10}-CN$, $-R^9-O-R^{10}-C(O)OR^8$, $-R^9-O-R^{10}-C(O)N(R^6)R^7$, $-R^9-O-R^{10}-S(O)_pR^8$ (where p is 0, 1 or 2), $-R^9-O-R^{10}-N(R^6)R^7$, $-R^9-O-R^{10}-C(NR^{11})N(R^{11})H$, $-R^9-OC(O)-R^8$, $-R^9-N(R^6)R^7$, $-R^9-C(O)R^8$, $-R^9-C(O)OR^8$, $-R^9-C(O)N(R^6)R^7$, $-R^9-N(R^6)C(O)OR^{12}$, $-R^9-N(R^6)C(O)R^8$, $-R^9-N(R^6)S(O)_tR^8$ (where t is 1 or 2), $-R^9-S(O)_tOR^8$ (where t is 1 or 2), $-R^9-S(O)_pR^8$ (where p is 0, 1 or 2), and $-R^9-$ S(O)$_t$N(R$^6$)R$^7$ (where t is 1 or 2); and R$^1$, R$^4$, R$^5$, each R$^6$, each R$^7$, each R$^8$, each R$^9$, each R$^{10}$, each R$^{11}$, each R$^{12}$, each R$^{13}$ and each R$^{14}$ are as described above for compounds of formula (I).

Another embodiment is the use where, in the compound of formula (Ia) as set forth above:

R$^1$, R$^4$ and R$^5$ are each independently hydrogen;

each R$^6$ and R$^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —R$^{10}$—OR$^8$, —R$^{10}$—CN, —R$^{10}$—NO$_2$, —R$^{10}$—N(R$^8$)$_2$, —R$^{10}$—C(O)OR$^8$ and —R$^{10}$—C(O)N(R$^8$)$_2$, or any R$^6$ and R$^7$, together with the common nitrogen to which they are both attached, form an optionally substituted N-heteroaryl or an optionally substituted N-heterocyclyl;

each R$^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each R$^9$ is independently selected from the group consisting of a direct bond and an optionally substituted straight or branched alkylene chain;

each R$^{10}$ is an optionally substituted straight or branched alkylene chain;

each R$^{11}$ is independently selected from the group consisting of hydrogen, alkyl, cyano, nitro and —OR$^8$;

each R$^{12}$ is independently selected from the group consisting of hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl, optionally substituted heteroarylalkyl, —R$^{10}$—OR$^8$, —R$^{10}$—CN, —R$^{10}$—NO$_2$, —R$^{10}$—N(R$^8$)$_2$, —R$^{10}$—C(O)OR$^8$ and —R$^{10}$—C(O)N(R$^8$)$_2$, or two R$^{12}$'s, together with the common nitrogen to which they are both attached, form an optionally substituted N-heterocyclyl or an optionally substituted N-heteroaryl;

each R$^{13}$ is independently selected from the group consisting of a direct bond and an optionally substituted straight or branched alkylene chain; and each R$^{14}$ is an optionally substituted straight or branched alkylene chain.

Another embodiment is the use where, in the compound of formula (Ia) as set forth above:

R$^2$ is aryl optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R$^{13}$—OR$^{12}$, —R$^{13}$—OC(O)—R$^{12}$, —R$^{13}$—O—R$^{14}$—N(R$^{12}$)$_2$, —R$^{13}$—N(R$^{12}$)—R$^{14}$—N(R$^8$)$_2$, —R$^{13}$—N(R$^{12}$)$_2$, —R$^{13}$—C(O)R$^{12}$, —R$^{13}$—C(O)OR$^{12}$, —R$^{13}$—C(O)N(R$^{12}$)$_2$, —R$^{13}$—C(O)N(R$^{12}$)—R$^{13}$—N(R$^2$)R$^{13}$, —R$^{13}$—C(O)N(R$^{12}$)—R$^{14}$—OR$^{12}$, —R$^{13}$—N(R$^{12}$)C(O)OR$^{12}$, —R$^{13}$—N(R$^{12}$)C(O)R$^{12}$, —R$^{13}$—N(R$^{12}$)S(O)$_t$R$^{12}$ (where t is 1 or 2), —R$^{13}$—S(O)$_t$OR$^{12}$ (where t is 1 or 2), —R$^{13}$—S(O)$_p$R$^{12}$ (where p is 0, 1 or 2), and —R$^{13}$—S(O)$_t$N(R$^{12}$)$_2$ (where t is 1 or 2).

Another embodiment is the method where, in the compound of formula (Ia) as set forth above:

R$^2$ is aryl selected from the group consisting of phenyl and 6,7,8,9-tetrahydro-5H-benzo[7]annulene-2-yl, each optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R$^{13}$—OR$^{12}$, —R$^{13}$—OC(O)—R$^{12}$, —R$^{13}$—O—R$^{14}$—N(R$^2$)$_2$, —R$^{13}$—N(R$^{12}$)—R$^{14}$—N(R$^{12}$)$_2$, —R$^{13}$—N(R$^{12}$)$_2$, —R$^{13}$—C(O)R$^{12}$, —R$^{13}$—C(O)OR$^{12}$, —R$^{13}$—C(O)N(R$^{12}$)$_2$, —R$^{13}$—C(O)N(R$^{12}$)—R$^{14}$—N(R$^{12}$)R$^{13}$, —R$^{13}$—C(O)N(R$^{12}$)—R$^{13}$—OR$^{12}$, —R$^{13}$—N(R$^{12}$)C(O)OR$^{12}$, —R$^{13}$—N(R$^{12}$)C(O)R$^{12}$, —R$^{13}$—N(R$^{12}$)S(O)$_t$R$^{12}$ (where t is 1 or 2), —R$^{13}$—S(O)OR$^{12}$ (where t is 1 or 2), —R$^1$—S(O)$_p$R$^{12}$ (where p is 0, 1 or 2), and —R$^{13}$—S(O)$_t$N(R$^{12}$)$_2$ (where t is 1 or 2); and R$^3$ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-pyrido[2',3':6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R$^9$—OR$^8$, —R$^9$—OC(O)—R$^8$, —R$^9$—N(R$^6$)R$^7$, —R$^9$—C(O)R$^8$, —R$^9$—C(O)OR$^8$, —R$^9$—C(O)N(R$^6$)R$^7$, —R$^9$—N(R$^6$)C(O)OR$^{12}$, —R$^9$—N(R$^6$)C(O)R$^8$, —R$^9$—N(R$^6$)S(O)$_t$R$^8$ (where t is 1 or 2), —R⁹—S(O)ₜOR⁸ (where t is 1 or 2), —R⁹—S(O)ₚR⁸ (where p is 0, 1 or 2), and —R⁹—S(O)ₜN(R⁶)R⁷ (where t is 1 or 2).

Another embodiment is the use where, in the compound of formula (Ia) as set forth above:

R² is phenyl optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl, optionally substituted heteroarylalkenyl, —R¹³—OR¹², —R¹³—OC(O)—R¹², —R¹³—O—R¹³—N(R¹²)₂, —R¹³—N(R¹²)—R¹⁴—N(R²)₂, —R¹³—N(R¹²)₂, —R¹³—C(O)R¹², —R¹³—C(O)OR¹², —R¹³—C(O)N(R¹²)₂, —R¹³—C(O)N(R¹²)—R¹⁴—N(R¹²)R¹³, —R¹³—C(O)N(R¹²)—R¹⁴—OR¹², —R¹³—N(R²)C(O)OR¹², —R¹³—N(R¹²)C(O)R¹², —R¹³—N(R¹²)S(O)ₜR¹² (where t is 1 or 2), —R¹³—S(O)ₜOR¹² (where t is 1 or 2), —R¹³—S(O)ₚR¹² (where p is 0, 1 or 2), and —R¹³—S(O)₁N(R¹²)₂ (where t is 1 or 2).

Another embodiment is the use where, in the compound of formula (Ia) as set forth above:

R² is phenyl optionally substituted by one or more substitutents selected from the group consisting of alkyl, halo, haloalkyl, cyano, and optionally substituted heterocyclyl where the optionally substituted heterocyclyl is selected from the group consisting of piperidinyl, piperazinyl, pyrrolidinyl, azepanyl, decahydropyrazino[1,2-a]azepinyl, octahydropyrrolo[3,4-c]pyrrolyl, azabicyclo[3.2.1]octyl, octahydropyrrolo[3,4-b]pyrrolyl, octahydropyrrolo[3,2-c]pyridinyl, 2,7-diazaspiro[4.4]nonanyl and azetidinyl; each independently optionally substituted by one or two substituents selected from the group consisting of —R⁹—OR⁸, —R⁹—N(R⁶)R⁷, —R⁹—C(O)OR⁶, —R⁹—C(O)N(R⁶)R⁷, —R⁹—N(R⁶)C(O)R⁷, —R⁹—N(R⁶)C(O)OR⁸, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

R³ is selected from the group consisting of 6,7-dihydro-5H-benzo[6,7]cyclohepta[1,2-c]pyridazin-3-yl, 6,7-dihydro-5H-pyrido[2',3':6,7]cyclohepta[1,2-c]pyridazin-3-yl, 6,7-dihydro-5H-benzo[6,7]cyclohepta[1,2-b]pyridin-2-yl, 6,7-dihydro-5H-benzo[2,3]thiepino[4,5-c]pyridazin-3-yl, spiro[chromeno[4,3-c]pyridazine-5,1'-cyclopentane]-3-yl and 6,7-dihydro-5H-benzo[6,7]cyclohepta[4,5-c]pyridazin-3-yl, each optionally substituted by one or more substituents selected from the group consisting of alkyl, aryl, halo and —R⁹—OR⁸.

Another embodiment is the use where the compound of formula (Ia), as set forth above, is selected from the group consisting of:

N³-(4-(4-cyclohexanylpiperazin-1-yl)phenyl)-1-(6,7-dihydro-5H-benzo[6,7]cyclohepta[1,2-c]pyridazin-3-yl)-1H-1,2,4-triazole-3,5-diamine;

1-(6,7-dihydro-5H-benzo[6,7]cyclohepta[1,2-c]pyridazin-3-yl)-N³-(3-fluoro-4-(4-(pyrrolidin-1-yl)piperidin-1-yl)-1H-1,2,4-triazole-3,5-diamine;

1-(6,7-dihydro-5H-benzo[6,7]cyclohepta[1,2-c]pyridazin-3-yl)-N³-(3-fluoro-4-(4-methyl-3-phenylpiperazin-1-yl)phenyl)-1H-1,2,4-triazole-3,5-diamine;

1-(6,7-dihydro-5H-benzo[6,7]cyclohepta[1,2-c]pyridazin-3-yl)-N³-(3-fluoro-(4-(4 piperidin-1-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-N³-(3-fluoro-4-(4-(indolin-2-on-1-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-N³-(3-fluoro-4-(4-(morpholin-4-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-N³-(4-(4-cyclopentyl-2-methylpiperazin-1-yl)phenyl)-1H-1,2,4-triazole-3,5-diamine;

1-(6,7-dihydro-5H-benzo[6,7]cyclohepta[1,2-c]pyridazin-3-yl)-N³-(4-(3,5-dimethylpiperazin-1-yl)phenyl)-1H-1,2,4-triazole-3,5-diamine;

1-(6,7-dihydro-5H-benzo[6,7]cyclohepta[1,2-c]pyridazin-3-yl)-N³-(4-(4-(pyrrolidin-1-yl)piperidin-1-yl)-3-cyanophenyl)-1H-1,2,4-triazole-3,5-diamine;

1-(6,7-dihydro-5H-benzo[6,7]cyclohepta[1,2-c]pyridazin-3-yl)-N³-(3-fluoro-4-(3-(diethylamino)pyrrolidin-1-yl)phenyl)-1H-1,2,4-triazole-3,5-diamine;

1-(6,7-dihydro-5H-benzo[6,7]cyclohepta[1,2-c]pyridazin-3-yl)-N³-(4-(4-(bicyclo[2.2.1]heptan-2-yl)piperazin-1-yl)phenyl)-1H-1,2,4-triazole-3,5-diamine;

1-(6,7-dihydro-5H-benzo[6,7]cyclohepta[1,2-c]pyridazin-3-yl)-N³-(4-(4-methylpiperazin-1-yl)phenyl)-1H-1,2,4-triazole-3,5-diamine;

1-(6,7-dihydro-5H-benzo[6,7]cyclohepta[1,2-c]pyridazin-3-yl)-N³-(3-fluoro-4-(4-(diethylamino)piperidin-1-yl)phenyl)-1H-1,2,4-triazole-3,5-diamine;

1-(6,7-dihydro-5H-9-methoxybenzo[6,7]cyclohepta[1,2-c]pyridazin-3-yl)-N³-(3-fluoro-4-(4-(pyrrolidin-1-yl)piperidin-1-yl)phenyl)-1H-1,2,4-triazole-3,5-diamine;

1-(6,7-dihydro-5H-10-fluorobenzo[6,7]cyclohepta[1,2-c]pyridazin-3-yl)-N³-(3-fluoro-4-(4-(pyrrolidin-1-yl)piperidin-1-yl)phenyl)-1H-1,2,4-triazole-3,5-diamine;

1-(6,7-dihydro-5H-10-fluorobenzo[6,7]cyclohepta[1,2c]pyridazin-3-yl)-N³-(3-fluoro-4-(4-(cyclohexyl)piperazin-1-yl)phenyl)-1H-1,2,4-triazole-3,5-diamine;

1-(6,7-dihydro-5H-9-methoxybenzo[6,7]cyclohepta[1,2-c]pyridazin-3-yl)-N³-(3-fluoro-4-(4-(cyclohexyl)piperazin-1-yl)phenyl)-1H-1,2,4-triazole-3,5-diamine;

1-(6,7-dihydro-5H-benzo[6,7]cyclohepta[1,2-c]pyridazin-3-yl)-N³-(3-fluoro-4-(4-(4-methylpiperazin-1-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-N³-(3-fluoro-4-(4-(4-methylpiperidin-1-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-N³-(3-fluoro-4-(4-dimethylaminopiperidin-1-yl)phenyl)-1H-1,2,4-triazole-3,5-diamine;

1-(6,7-dihydro-5H-benzo[6,7]cyclohepta[1,2-c]pyridazin-3-yl)-N³-(3-chloro-4-(4-pyrrolidin-1-yl-piperidin-1-yl)phenyl)-1H-1,2,4-triazole-3,5-diamine;

1-(6,7-dihydro-5H-benzo[6,7]cyclohepta[1,2-c]pyridazin-3-yl)-N³-(3-trifluoromethyl-4-(4-pyrrolidin-1-yl-piperidin-1-yl)phenyl)-1H-1,2,4-triazole-3,5-diamine;

1-(6,7-dihydro-5H-9,10-dimethoxybenzo[6,7]cyclohepta[1,2-c]pyridazin-3-yl)-N³-(3-fluoro-4-(4-pyrrolidin-1-yl-piperidin-1-yl)phenyl)-1H-1,2,4-triazole-3,5-diamine;

1-(6,7-dihydro-5H-9,10,11-trimethoxybenzo[6,7]cyclohepta[1,2-c]pyridazin-3-yl)-N³-(3-fluoro-4-(4-pyrrolidin-1-yl-piperidin-1-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(5-methyloctahydropyrrolo[3,4-c]pyrrolyl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(3-pyrrolidin-1-yl-piperidin-1-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(3-pyrrolidin-1-yl-azepan-1-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(4-N$^3$-methylpiperidin-4-yl-piperidin-1-yl)phenyl)-1H-1,2,4-triazole-3,5-diamine;

1-(6,7-dihydro-5H-benzo[6,7]cyclohepta[4,5-c]pyridazin-2-yl)-N$^3$-(3-fluoro-4-(4-(pyrrolidinyl)piperidinyl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(5-propyloctahydropyrrolo[3,4-c]pyrrolyl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(decahydropyrazino[1,2-a]azepin-2-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(5-cyclopentyloctahydropyrrolo[3,4-c]pyrrolyl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(3-(pyrrolidin-1-yl)-8-azabicyclo[3.2.1]oct-8-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(4-pyrrolidin-1-yl-azepan-1-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(4-(4-methylpiperazin-1-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(4-(4-isopropylpiperazin-1-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(1-methyloctahydropyrrolo[3,4-b]pyrrol-5-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(4-(N-methylcyclopentylamino)piperidinyl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(4-(dipropylamino)piperidin-1-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(1-propyloctahydro-1H-pyrrolo[3,2-c]pyridine-5-yl)phenyl)-1H-1,2,4-triazole-3,5-diamine;

1-(6,7-dihydro-5H-benzo[6,7]cyclohepta[4,5-c]pyridazin-2-yl)-N$^3$-(3-fluoro-4-(4-(N-methylpiperazin-1l-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(4-(tert-butyloxycarbonylamino)piperidin-1-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(4-aminopiperidin-1-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(4-(5-cyclohexyloctahydropyrrolo[3,4-c]pyrrolyl)piperidin-1-yl)phenyl)-1H-1,2,4-triazole-3,5-diamine;

1-(6,7-dihydro-5H-benzo[6,7]cyclohepta[1,2-c]pyridazin-3-yl)-NM-(4-(methylpiperidin-4-yl)phenyl)-1H-1,2,4-triazole-3,5-diamine;

1-(6,7-dihydro-5H-benzo[6,7]cyclohepta[1,2-c]pyridazin-3-yl)-N$^3$-(4-(4-pyrrolidin-1-ylpiperidinyl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(4-pyrrolidin-1-ylpiperidinyl)phenyl)-1H-1,2,4-triazole-3,5-diamine;

1-(6,7-dihydro-5H-benzo[6,7]cyclohepta[1,2-c]pyridazin-3-yl)-N$^3$-(3-methyl-4-(4-pyrrolidin-1-yl piperidinyl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(4-cyclopentylpiperazinyl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(4-N$^3$-methylpiperidin-4-ylpiperazinyl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(7-methyl-2,7-diazaspiro[4.4]nonan-2-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(N-isopropylpiperazin-1-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(3-pyrrolidin-1-ylazetidinyl)phenyl)-1H-1,2,4-triazole-3,5-diamine;

1-(6,7-dihydro-5H-benzo[6,7]cyclohepta[1,2-c]pyridazin-3-yl)-N$^3$-(3-methyl-4-(4-(N-methylpiperazin-4-yl)piperidin-1-yl)phenyl)-1H-1,2,4-triazole-3,5-diamine;

1-(6,7-dihydro-5H-benzo[6,7]cyclohepta[1,2c]pyridazin-3-yl)-N$^3$-(3-fluoro-4-((S)-3-(pyrrolidin-1-ylmethyl)pyrrolidinyl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(4-(pyrrolidinylmethyl)piperidinyl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-((4aR,8aS)-decahydroisoquinolin-2-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(octahydro-1H-pyrido[1,2-a]pyrazin-2-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-(4-(3-pyrrolidin-1-yl)pyrrolidin-1-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(4-(5-methyloctahydropyrrolo[3,4-c]pyrrolyl)piperidin-1-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(octahydropyrrolo[3,4-c]pyrrolyl)phenyl)-1H-1,2,4-triazole-3,5-diamine;

1-(6,7-dihydro-9-chloro-5H-benzo[6,7]cyclohepta[1,2-c]pyridazin-3-yl)-N$^3$-(3-fluoro-4-(4-pyrrolidin-1-ylpiperidin-1-yl)phenyl)-1H-1,2,4-triazole-3,5-diamine;

1-(6,7-dihydro-9-chloro-5H-benzo[6,7]cyclohepta[1,2-c]pyridazin-3-yl)-N$^3$-(3-fluoro-4-(4-(N-methylpiperazin-1-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-N$^3$-(4-iodophenyl)-1-1,2,4-triazole-3,5-diamine;

1-(spiro[chromeno[4,3-c]pyridazine-5,1'-cyclopentane]-3-yl)-N$^3$-(3-fluoro-4-(4-(4-methylpiperazin-1-yl)piperidin-1-yl)phenyl)-1H-1,2,4-triazole-3,5-diamine;

1-(spiro[chromeno[4,3-c]pyridazine-5,1'-cyclopentane]-3-yl)-N$^3$-(3-fluoro-4-(4-(pyrrolidin-1-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-N$^3$-(3-fluoro-4-(4-pyrrolidin-1-ylpiperidin-1-yl)phenyl)-1H-1,2,4-triazole-3,5-diamine;

1-(6,7-dihydro-5H-benzo[6,7]cyclohepta[4,5-c]pyridazin-2-yl)-N$^3$-(3-fluoro-4-(4-pyrrolidin-1-ylpiperidin-1-yl)phenyl)-1H-1,2,4-triazole-3,5-diamine;

1-(6,7-dihydro-5H-benzo[6,7]cyclohepta[1,2c]pyridazin-3-yl)-N³-(3-fluoro-4-(4-methylpiperazin-1-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-N³-(3-fluoro-4-(3-(3R)-dimethylaminopyrrolidin-1-yl)phenyl)-1H-1,2,4-triazole-3,5-diamine;

1-(6,7-dihydro-5H-benzo[6,7]cyclohepta[4,5-c]pyridazin-2-yl)-N³-(3-methyl-4-(4-pyrrolidin-1-ylpiperidin-1-yl)phenyl)-1H-1,2,4-triazole-3,5-diamine;

1-(6,7-dihydro-5H-benzo[6,7]cyclohepta[4,5-c]pyridazin-2-yl)-N³-(3-fluoro-4-(4-pyrrolidin-1-ylpiperidin-1-yl)phenyl)-1H-1,2,4-triazole-3,5-diamine;

1-(4-phenyl-6,7-dihydro-5H-benzo[6,7]cyclohepta[1,2-b]pyridin-2-yl)-N³-(3-fluoro-4-(4-cyclohexylpiperazin-1-yl)phenyl)-1H-1,2,4-triazole-3,5-diamine;

1-(4-phenyl-6,7-dihydro-5H-benzo[6,7]cyclohepta[1,2-b]pyridin-2-yl)-N³-(4-(4-methylpiperazin-1-yl)phenyl)-1H-1,2,4-triazole-3,5-diamine;

1-(6,7-dihydro-5H-benzo[6,7]cyclohepta[1,2-c]pyridazin-3-yl)-N³-(3-fluoro-4-(4-methylpiperazin-1-yl)phenyl)-1H-1,2,4-triazole-3,5-diamine;

1-(6,7-dihydro-5H-benzo[6,7]cyclohepta[1,2-c]pyridazin-3-yl)-N³-(4-(1-bicyclo[2.2.1]heptan-2-yl)-piperidin-4-yl)phenyl)-1H-1,2,4-triazole-3,5-diamine;

1-(6,7-dihydro-5H-benzo[6,7]cyclohepta[1,2-c]pyridazin-3-yl)-N³-(4-(1-cyclopropylmethylpiperidin-4-yl)phenyl)-1H-1,2,4-triazole-3,5-diamine; 1-(6,7-dihydro-5H-benzo[6,7]cyclohepta[1,2-c]pyridazin-3-yl)-N³-(3-fluoro-4-(4-cyclopropylmethylpiperazin-1-yl)phenyl)-1H-1,2,4-triazole-3,5-diamine;

1-(6,7-dihydro-5H-benzo[2,3]thiepino[4,5-c]pyridazin-3-yl)-N³-(4-(1-bicyclo[2.2.1]heptan-2-yl)-piperidin-4-yl)phenyl)-1H-1,2,4-triazole-3,5-diamine;

1-(4-phenyl-6,7-dihydro-5H-benzo[6,7]cyclohepta[1,2-b]pyridin-2-yl)-NM-(3-fluoro-4-(4-pyrrolidin-1-ylpiperidin-1-yl)phenyl)-1H-1,2,4-triazole-3,5-diamine, and 1-(6,7-dihydro-5H-pyrido[2',3':6,7]cyclohepta[1,2-c]pyridazin-3-yl)-N³-(3-fluoro-4-(4-(pyrrolidin-1-yl)piperidin-1-yl)phenyl)-1H-1,2,4-triazole-3,5-diamine.

Another embodiment is the use where, in the compound of formula (Ia) as set forth above:

R² is phenyl optionally substituted by one or more substitutents selected from the group consisting of halo, alkyl, heterocyclylalkenyl, —R¹³—OR¹², —R¹³—O—R¹³—N(R¹²)₂, —R¹³—N(R¹²)—R¹⁴—N(R¹²)₂, —R¹³—N(R¹²)₂, —R¹³—C(O)R¹², —R¹³—C(O)N(R¹²)₂, and —R¹³—N(R¹²)C(O)R²;

R³ is selected from the group consisting of 6,7-dihydro-5H-benzo[6,7]cyclohepta[1,2-c]pyridazin-3-yl and 6,7-dihydro-5H-benzo[6,7]cyclohepta[4,5-c]pyridazin-3-yl, each optionally substituted by one or more substituents selected from the group consisting of alkyl, aryl, halo and —R⁹—OR⁸.

Another embodiment is the use where the compound of formula (Ia), as set forth above, is selected from the group consisting of:

1-(6,7-dihydro-5H-benzo[6,7]cyclohepta[1,2-c]pyridazin-3-yl)-N³-(4-(2-(pyrrolidin-1-yl)ethoxy)phenyl)-1H-1,2,4-triazole-3,5-diamine;

1-(6,7-dihydro-5H-benzo[6,7]cyclohepta[1,2-c]pyridazin-3-yl)-N³-(4-(4-(cyclopentyl)piperazin-1-ylcarbonyl)phenyl)-1H-1,2,4-triazole-3,5-diamine;

1-(6,7-dihydro-5H-benzo[6,7]cyclohepta[1,2-c]pyridazin-3-yl)-N³-(4-((2-pyrrolidin-1-ylethyl)aminocarbonyl)phenyl)-1H-1,2,4-triazole-3,5-diamine;

1-(6,7-dihydro-5H-benzo[6,7]cyclohepta[1,2-c]pyridazin-3-yl)-N³-(4-(2,2,6,6-tetramethylpiperidin-1-yl)ethoxyphenyl)-1H-1,2,4-triazole-3,5-diamine;

1-(6,7-dihydro-5H-benzo[6,7]cyclohepta[1,2-c]pyridazin-3-yl)-N³-(4-((2-(dimethylamino)ethyl)aminocarbonyl)phenyl)-1H-1,2,4-triazole-3,5-diamine;

1-(6,7-dihydro-5H-benzo[6,7]cyclohepta[1,2-c]pyridazin-3-yl)-N³-(4-((2-(methoxy)ethyl)aminocarbonyl)phenyl)-1H-1,2,4-triazole-3,5-diamine;

1-(6,7-dihydro-5H-benzo[6,7]cyclohepta[1,2-c]pyridazin-3-yl)-N³-(4-((2-(pyrrolidin-1-yl)ethyl)aminocarbonyl)phenyl)-1H-1,2,4-triazole-3,5-diamine;

1-(6,7-dihydro-5H-benzo[6,7]cyclohepta[1,2-c]pyridazin-3-yl)-N³-(4-((4-(pyrrolidin-1-yl)piperidin-1-yl)carbonyl)phenyl)-1H-1,2,4-triazole-3,5-diamine;

1-(6,7-dihydro-5H-benzo[6,7]cyclohepta[1,2-c]pyridazin-3-yl)-N³-(3-chloro-4-(2-(pyrrolidin-1-yl)ethoxy)phenyl)-1H-1,2,4-triazole-3,5-diamine;

1-(6,7-dihydro-5H-benzo[6,7]cyclohepta[1,2-c]pyridazin-3-yl)-N³-(3-fluoro-4-(2-(pyrrolidin-1-yl)ethoxy)phenyl)-1H-1,2,4-triazole-3,5-diamine;

1-(6,7-dihydro-5H-10-fluorobenzo[6,7]cyclohepta[1,2-c]pyridazin-3-yl)-N³-(3-fluoro-4-(2-(pyrrolidin-1-yl)ethoxy)phenyl)-1H-1,2,4-triazole-3,5-diamine;

1-(6,7-dihydro-5H-9-methoxybenzo[6,7]cyclohepta[1,2-c]pyridazin-3-yl)-N³-(3-fluoro-4-(2-(pyrrolidin-1-yl)ethoxy)phenyl)-1H-1,2,4-triazole-3,5-diamine;

1-(6,7-dihydro-5H-benzo[6,7]cyclohepta[1,2-c]pyridazin-3-yl)-N³-(4-(2-(N-methylcyclopentylamino)ethoxy)phenyl)-1H-1,2,4-triazole-3,5-diamine;

1-(6,7-dihydro-5H-benzo[6,7]cyclohepta[1,2-c]pyridazin-3-yl)-N³-(3-fluoro-4-(N-methylpiperidin-4-yl-N³-methylamino)phenyl)-1H-1,2,4-triazole-3,5-diamine;

1-(6,7-dihydro-5H-benzo[6,7]cyclohepta[1,2-c]pyridazin-3-yl)-N³-(4-((N-butyl-N³-acetoamino)methyl)phenyl)-1H-1,2,4-triazole-3,5-diamine;

1-(6,7-dihydro-5H-benzo[6,7]cyclohepta[1,2-c]pyridazin-3-yl)-N³-(4-(4-(4-methylpiperazin-1-yl)piperidin-1-yl-prop-1-enyl)phenyl)-1H-1,2,4-triazole-3,5-diamine;

1-(6,7-dihydro-5H-benzo[6,7]cyclohepta[1,2-c]pyridazin-3-yl)-N³-(4-(4-(piperidin-1-yl)piperidin-1-ylprop-1-enyl)phenyl)-1H-1,2,4-triazole-3,5-diamine;

1-(6,7-dihydro-5H-benzo[6,7]cyclohepta[1,2-c]pyridazin-3-yl)-N³-(4-(piperidin-1-ylprop-1-enyl)phenyl)-1H-1,2,4-triazole-3,5-diamine;

1-(6,7-dihydro-5H-benzo[6,7]cyclohepta[1,2-c]pyridazin-3-yl)-N³-(4-(pyrrolidin-1-ylprop-1-enyl)phenyl)-1H-1,2,4-triazole-3,5-diamine;

1-(6,7-dihydro-5H-benzo[6,7]cyclohepta[1,2-c]pyridazin-3-yl)-N³-(4-(3-dimethylaminopyrrolidin-1-ylprop-1-enyl)phenyl)-1H-1,2,4-triazole-3,5-diamine;

1-(6,7-dihydro-5H-benzo[6,7]cyclohepta[1,2-c]pyridazin-3-yl)-N³-(4-(3-diethylaminopyrrolidin-1-ylprop-1-enyl)phenyl)-1H-1,2,4-triazole-3,5-diamine;

1-(6,7-dihydro-5H-benzo[6,7]cyclohepta[1,2-c]pyridazin-3-yl)-N³-(4-(4-pyrrolidin-1-ylpiperidin-1-ylprop-1-enyl)phenyl)-1H-1,2,4-triazole-3,5-diamine;

1-(6,7-dihydro-5H-benzo[6,7]cyclohepta[1,2-c]pyridazin-3-yl)-N³-(4-(4-methylpiperazin-1-ylprop-1-enyl)phenyl)-1H-1,2,4-triazole-3,5-diamine;

1-(6,7-dihydro-5H-benzo[6,7]cyclohepta[1,2-c]pyridazin-3-yl)-N³-(4-(4-isopropylpiperazin-1-ylprop-1-enyl)phenyl)-1H-1,2,4-triazola-3,5-diamine;

1-(6,7-dihydro-5H-benzo[6,7]cyclohepta[1,2-c]pyridazin-3-yl)-N³-(4-(4-cyclopentylpiperazin-1-ylprop-1-enyl)phenyl)-1H-1,2,4-triazole-3,5-diamine;

1-(6,7-dihydro-5H-benzo[6,7]cyclohepta[1,2-c]pyridazin-3-yl)-(4-(morpholin-4-ylprop-1-enyl)phenyl)-1H-1,2,4-triazole-3,5-diamine; and 1-(6,7-dihydro-5H-benzo[6,7]cyclohepta[1,2-c]pyridazin-3-yl)-N³-(4-(1-methylpiperidin-3-yl-oxy)phenyl)-1H-1,2,4-triazole-3,5-diamine.

Another embodiment is the use where, in the compound of formula (Ia) as set forth above:

R² is phenyl optionally substituted by one or more substitutents selected from the group consisting of alkyl, halo, haloalkyl, cyano, and optionally substituted heterocyclyl where the optionally substituted heterocyclyl is selected from the group consisting of piperidinyl, piperazinyl, pyrrolidinyl, azepanyl, decahydropyrazino[1,2-a]azepinyl, octahydropyrrolo[3,4-c]pyrrolyl, azabicyclo[3.2.1]octyl, octahydropyrrolo[3,4-b]pyrrolyl, octahydropyrrolo[3,2-c]pyridinyl, 2,7-diazaspiro[4.4]nonanyl and azetidinyl; each independently optionally substituted by one or two substituents selected from the group consisting of —R⁹—OR⁸, —R⁹—N(R⁶)R⁷, —R⁹—C(O)OR⁶, —R—C(O)N(R⁶)R⁷, —R⁹—N(R')C(O)R⁷, —R⁹—N(R⁶)C(O)OR⁷, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl; and R³ is selected from the group consisting of 6,7-dihydro-5H-benzo[6,7]cyclohepta[1,2-d]pyrimidin-4-yl and 6,7-dihydro-5H-benzo[6,7]cyclohepta[1,2-d]pyrimidin-2-yl, each optionally substituted by one or more substituents selected from the group consisting of alkyl, aryl, halo and —R⁹—OR⁸.

Another embodiment is the use where the compound of formula (Ia), as set forth above, is selected from the group consisting of:

1-(6,7-dihydro-5H-benzo[6,7]cyclohepta[1,2-d]pyrimidin-4-yl)-N³-(4-(4-(bicyclo[2.2.1]heptan-2-yl)piperazin-1-yl)phenyl)-1H-1,2,4-triazole-3,5-diamine;

1-(6,7-dihydro-5H-benzo[6,7]cyclohepta[1,2-d]pyrimidin-4-yl)-N³-(3-fluoro-4-(4-(diethylamino)piperidin-1-yl)phenyl)-1H-1,2,4-triazole-3,5-diamine;

1-(6,7-dihydro-5H-benzo[6,7]cyclohepta[1,2-d]pyrimidin-2-yl)-N³-(4-(N-methylpiperazin-1-yl)phenyl)-1H-1,2,4-triazole-3,5-diamine;

1-(6,7-dihydro-5H-benzo[6,7]cyclohepta[1,2-d]pyrimidin-2-yl)-N³-(3-fluoro-4-(4-cyclohexylpiperazinyl)phenyl)-1H-1,2,4-triazole-3,5-diamine; and 1-(6,7-dihydro-5H-benzo[6,7]cyclohepta[1,2-d]pyrimidin-2-yl)-N³-(4-(4-(2S)-bicyclo[2.2.1]heptan-2-yl)-piperazinylphenyl)-1H-1,2,4-triazole-3,5-diamine.

Another embodiment is the use where, in the compound of formula (Ia) as set forth above:

R² is phenyl optionally substituted by one or more substitutents selected from the group consisting of halo, alkyl, heterocyclylalkenyl, —R¹³—OR¹², —R¹³—O—R¹⁴—N(R¹²)₂, —R¹³—N(R²)—R¹⁴—N(R²)₂, —R¹³—N(R¹²)₂, —R¹³—C(O)R¹², —R¹³—C(O)N(R¹²)₂, and —R¹³—N(R¹²)C(O)R¹²; and R³ is selected from the group consisting of 6,7-dihydro-5H-benzo[6,7]cyclohepta[1,2-d]pyrimidin-4-yl and 6,7-dihydro-5H-benzo[6,7]cyclohepta[1,2-d]pyrimidin-2-yl, each optionally substituted by one or more substituents selected from the group consisting of alkyl, aryl, halo and —R⁹—OR⁸.

Another embodiment is the method where the compound of formula (Ia), as set forth above, is selected from the group consisting of:

1-(6,7-dihydro-5H-benzo[6,7]cyclohepta[1,2-d]pyrimidin-2-yl)-N³-(3-fluoro-4-(2-(pyrrolidin-1-yl)ethoxy)phenyl)-1H-1,2,4-triazole-3,5-diamine; and 1-(6,7-dihydro-5H-benzo[6,7]cyclohepta[1,2-d]pyrimidin-4-yl)-N³-(4-(2-(pyrrolidin-1-yl)ethoxy)phenyl)-1H-1,2,4-triazole-3,5-diamine.

Another embodiment is the use where, in the compound of formula (Ia) as set forth above:

R² is phenyl optionally substituted by one or more substitutents selected from the group consisting of alkyl, halo, haloalkyl, cyano, and optionally substituted heterocyclyl where the optionally substituted heterocyclyl is selected from the group consisting of piperidinyl, piperazinyl, pyrrolidinyl, azepanyl, decahydropyrazino[1,2-a]azepinyl, octahydropyrrolo[3,4-c]pyrrolyl, azabicyclo[3.2.1]octyl, octahydropyrrolo[3,4-b]pyrrolyl, octahydropyrrolo[3,2-c]pyridinyl, 2,7-diazaspiro[4.4]nonanyl and azetidinyl; each independently optionally substituted by one or two substituents selected from the group consisting of —R⁹—OR⁸, —R⁹—N(R⁶)R⁷, —R⁹—C(O)OR⁸, —R⁹—C(O)N(R⁶)R⁷, —R⁹—N(R⁶)C(O)R⁷, —R⁹—N(R⁶)C(O)OR⁷, alkyl, halo, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl; and R³ is selected from the group consisting of 6,7-dihydro-5H-benzo[2,3]azepino[4,5-c]pyridazin-3-yl, (Z)-dibenzo[b,f][1,4]thiazepin-11-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, each optionally substituted by one or more substituents selected from the group consisting of alkyl, aryl, halo and —R⁹—OR⁸.

Another embodiment is the use where the compound of formula (Ia), as set forth above, is selected from the group consisting of:

1-(7-methyl-6,7-dihydro-5H-benzo[2,3]azepino[4,5-c]pyridazin-3-yl)-N³-(4-(N-methylpiperazin-1-yl)phenyl)-1H-1,2,4-triazole-3,5-diamine;

1-(7-methyl-6,7-dihydro-5H-benzo[2,3]azepino[4,5-c]pyridazin-3-yl)-N³-(3-fluoro-4-(4-cyclohexylpiperazinyl)phenyl)-1H-1,2,4-triazole-3,5-diamine;

1-((Z)-dibenzo[b,f][1,4]thiazepin-11-yl)-N³-(4-(4-N³-methylpiperazinyl)phenyl)-1H-1,2,4-triazole-3,5-diamine;

1-((Z)-dibenzo[b,f][,4]thiazepin-11-yl)-N³-(3-fluoro-4-(4-diethylaminopiperidin-1-yl)phenyl)-1H-1,2,4-triazole-3,5-diamine;

1-(6,7-dihydro-1H-benzo[2,3]oxepino[4,5-c]pyridazin-3-yl)-N³-(4-(4-pyrrolidin-1-ylpiperidinyl)phenyl)-1H-1,2,4-triazole-3,5-diamine;

1-(6,7-dihydro-5H-benzo[2,3]oxepino[4,5-c]pyridazin-3-yl)-N³-(3-fluoro-4-(4-pyrrolidin-1-ylpiperidinyl)phenyl)-1H-1,2,4-triazole-3,5-diamine;

1-(6,7-dihydro-5H-benzo[2,3]thiepino[4,5-c]pyridazin-3-yl)-N³-(3-fluoro-4-(4-pyrrolidin-1-ylpiperidinyl)phenyl)-1H-1,2,4-triazole-3,5-diamine;

1-(6,7-dihydro-5H-benzo[2,3]thiepino[4,5-c]pyridazin-3-yl)-NM-(4-(4-pyrrolidin-1-ylpiperidinyl)phenyl)-1H-1,2,4-triazole-3,5-diamine;

1-(6,7-dihydro-5H-benzo[2,3]thiepino[4,5-c]pyridazin-3-yl)-N³-(3-fluoro-4-(4-(pyrrolidinylmethyl)piperidinyl)phenyl)-1H-1,2,4-triazole-3,5-diamine;

1-(6,7-dihydro-5H-benzo[2,3]thiepino[4,5-c]pyridazin-3-yl)-$N^3$-(3-fluoro-4-((4aR,8aS)-decahydroisoquinolin-2-yl)phenyl)-1H-1,2,4-triazole-3,5-diamine; and 1-(6,7-dihydro-5H-benzo[2,3]thiepino[4,5-c]pyridazin-3-yl)-$N^3$-(3-fluoro-4-(octahydro-1H-pyrido[1,2-a]pyrazin-2-yl)phenyl)-1H-1,2,4-triazole-3,5-diamine.

Another embodiment is the use where, in the compound of formula (Ia) as set forth above:

$R^2$ is phenyl optionally substituted by one or more substitutents selected from the group consisting of halo, alkyl, heterocyclylalkenyl, $-R^{13}-OR^{12}$, $-R^{13}-O-R^{13}-N(R^{12})_2$, $-R^{13}-N(R^{12})-R^{14}-N(R^{12})_2$, $-R^{13}-N(R^{12})_2$, $-R^{13}-C(O)R^{12}$, $-R^{13}-C(O)N(R^{12})_2$, and $-R^{13}-N(R^{12})C(O)R^{12}$; and $R^3$ is selected from the group consisting of 6,7-dihydro-5H-benzo[2,3]azepino[4,5-c]pyridazin-3-yl, (Z)-dibenzo[b,f][1,4]thiazepin-11-yl, 6,7-dihydro-5H-benzo[2,3]oxepino[4,5-c]pyridazin-3-yl, and 6,7-dihydro-5H-benzo[2,3]thiepino[4,5-c]pyridazin-3-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, $-R^9-OR^8$, $-R^9-OC(O)-R^8$, $-R^9-N(R^6)R^7$, $-R^9-C(O)R^8$, $-R^9-C(O)OR^8$, $-R^9-C(O)N(R^6)R^7$, $-R^9-N(R^6)C(O)OR^{12}$, $-R^9-N(R^6)C(O)R^8$, $-R^9-N(R^6)S(O)_tR^8$ (where t is 1 or 2), $-R^9-S(O)_tOR^8$ (where t is 1 or 2), $-R^9-S(O)_pR^8$ (where p is 0, 1 or 2), and $-R^9-S(O)_tN(R^6)R^7$ (where t is 1 or 2).

Another embodiment is the use where the compound of formula (Ia), as set forth above, is selected from the group consisting of:

1-(7-methyl-6,7-dihydro-5H-benzo[2,3]azepino[4,5-c]pyridazin-3-yl)-$N^3$-(3-fluoro-4-(2-(pyrrolidin-1-yl)ethoxy)phenyl)-1H-1,2,4-triazole-3,5-diamine; and 1-((Z)-dibenzo[b,f][,4]thiazepin-11-yl)-$N^3$-(4-(2-(pyrrolidin-1-yl)ethoxy)phenyl)-1H-1,2,4-triazole-3,5-diamine.

Another embodiment is the method where, in the compound of formula (Ia) as set forth above:

$R^2$ is phenyl optionally substituted by a substituent selected from the group consisting of optionally substituted heterocyclylalkyl, optionally substituted heteroaryl and optionally substituted heteroarylalkyl;

$R^3$ is selected from the group consisting of 6,7-dihydro-5H-benzo[6,7]cyclohepta[1,2-c]pyridazin-3-yl and 6,7-dihydro-5H-benzo[2,3]thiepino[4,5-c]pyridazin-3-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, $-R^9-OR^8$, $-R^9-OC(O)-R^8$, $-R^9-N(R^6)R^7$, $-R^9-C(O)R^8$, $-R^9-C(O)OR^8$, $-R^9-C(O)N(R^6)R^7$, $-R^9-N(R^6)C(O)OR^{12}$, $-R^9-N(R^6)C(O)R^8$, $-R^9-N(R^6)S(O)_tR^8$ (where t is 1 or 2), $-R^9-S(O)_tOR^8$ (where t is 1 or 2), $-R^9-S(O)_pR^8$ (where p is 0, 1 or 2), and $-R^9-S(O)_tN(R^6)R^7$ (where t is 1 or 2)

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $-R^{10}-OR^8$, $-R^{10}-CN$, $-R^{10}-NO_2$, $-R^{10}-N(R)_2$, $-R^{10}-C(O)OR^8$ and $-R^{10}-C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain; and $R^{12}$ is independently selected from the group consisting of hydrogen, alkyl, haloalkyl, alkenyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl.

Another embodiment is the use where the compound of formula (Ia), as set forth above, is selected from the group consisting of:

1-(6,7-dihydro-5H-benzo[6,7]cyclohepta[1,2-c]pyridazin-3-yl)-$N^3$-(4-((4-methylpiperazin-1-yl)methyl)phenyl)-1H-1,2,4-triazole-3,5-diamine;

1-(6,7-dihydro-5H-benzo[6,7]cyclohepta[1,2-c]pyridazin-3-yl)-$N^3$-(4-((5-fluoroindolin-2-on-3-yl)methyl)phenyl)-1H-1,2,4-triazole-3,5-diamine;

1-(6,7-dihydro-5H-benzo[6,7]cyclohepta[1,2-c]pyridazin-3-yl)-$N^3$-(4-((4-pyrrolidin-1-ylpiperidinyl)methyl)phenyl)-1H-1,2,4-triazole-3,5-diamine;

1-(6,7-dihydro-5H-benzo[6,7]cyclohepta[1,2-c]pyridazin-3-yl)-$N^3$-(4-((4-cyclopentylpiperazinyl)methyl)phenyl)-1H-1,2,4-triazole-3,5-diamine;

1-(6,7-dihydro-5H-benzo[6,7]cyclohepta[1,2-c]pyridazin-3-yl)-$N^3$-(4-((4-isopropylpiperazinyl)methyl)phenyl)-1H-1,2,4-triazole-3,5-diamine; and 1-(6,7-dihydro-5H-benzo[2,3]thiepino[4,5-c]pyridazin-3-yl)-$N^3$-(3-fluoro-4-(isoindolin-2-yl)phenyl)-1H-1,2,4-triazole-3,5-diamine.

Another embodiment is the use where, in the compound of formula (Ia) as set forth above:

$R^1$, $R^4$ and $R^5$ are each independently hydrogen;

$R^2$ is 6,7,8,9-tetrahydro-5H-benzo[7]annulene-2-yl optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl, optionally substituted heteroarylalkenyl, $-R^3-OR^{12}$, $-R^{13}-OC(O)-R^{12}$, $-R^{13}-O-R^{14}-N(R^{12})_2$, $-R^{13}-N(R^{12})-R^{14}-N(R^{12})_2$, $-R^{13}-N(R^{12})_2$, $-R^{13}-C(O)R^{12}$, $-R^{13}-C(O)OR^{12}$, $-R^{13}-C(O)N(R^{12})_2$, $-R^{13}-C(O)N(R^{12})-R^4-N(R^2)R^{13}$, $-R^{13}-C(O)N(R^{12})-R^{14}-OR^{12}$, $-R^{13}-N(R^{12})C(O)OR^{12}$, $-R^{13}-N(R^{12})C(O)R^{12}$, $-R^{13}-N(R^{12})S(O)_tR^{12}$ (where t is 1 or 2), —R³—S(O)ₜOR¹² (where t is 1 or 2), —R¹³—S(O)ₚR² (where p is 0, 1 or 2), and —R¹³—S(O)ₜN(R¹²)₂ (where t is 1 or 2); and R³ is a polycyclic heteroaryl containing more than 14 ring atoms selected from the group consisting of 6,7-dihydro-5H-benzo[6,7]cyclohepta[1,2-c]pyridazin-3-yl, 6,7-dihydro-5H-pyrido[2',3':6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R⁹—OR⁸, —R⁹—OC(O)—R⁸, —R⁹—N(R⁶)R⁷, —R⁹—C(O)R⁸, —R⁹—C(O)OR⁸, —R⁹—C(O)N(R⁶)R⁷, —R⁹—N(R⁶)C(O)OR¹², —R⁹—N(R⁶)C(O)R⁸, —R⁹—N(R⁶)S(O)ₜR⁸ (where t is 1 or 2), —R⁹—S(O)ₜOR⁸ (where t is 1 or 2), —R⁹—S(O)ₚR⁸ (where p is 0, 1 or 2), and —R⁹—S(O)ₜN(R⁶)R⁷ (where t is 1 or 2); and each R⁶, each R⁷, each R⁸, each R⁹, each R¹², each R¹³ and each R¹⁴ are as described above for compounds of formula (Ia).

Another embodiment is the use where the compound of formula (Ia), as set forth above, is selected from the group consisting of:

1-(6,7-dihydro-5H-benzo[6,7]cyclohepta[1,2-c]pyridazin-3-yl)-N³-(7-(pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-((bicyclo[2.2.1]heptan-2-yl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-((bicyclo[2.2.1]heptan-2-yl)(methyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7-piperidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7-azetidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7-(R)-pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-diethylamino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-cyclopentylamino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7-(S)-pyrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7-(2-(S)-methyloxycarbonyl)pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7-(2-(S)-carboxy)pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(8-diethylaminoethyl-9hydroxy-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-(3-(S-fluoropyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-(2-(S)-methylpyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-(3-(R)-hydroxypyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl-N³-(7-(2-(R)-methylpyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-(3-(S)-hydroxypyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-(3-(R)-fluoropyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-oxo-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-cyclohexylamino 6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-cyclopropylamino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-hydroxy-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-(4-methylpiperazin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-tetrahydrofuran-2-ylmethyl)amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-cyclobutylamino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-(cyclopropylmethyl)amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-(2-(diethylamino)ethyl)methylamino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-(4-pyrrolidin-1-ylpiperidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-(4-(piperidin-1-ylmethyl)piperidin-1-yl-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-(2-(dimethylamino)ethyl)amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-(carboxymethyl)amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(t-butoxycarbonylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7(acetamido)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-((2R)-2-(methoxycarbonyl)pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-(4,4-difluoropiperidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-((methoxycarbonylmethyl)(methyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-((2R)-2-(carboxy)pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-(4-(ethoxycarbonyl)piperidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-(4-(carboxy)piperidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-((carboxymethyl)(methyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-(4-(ethoxycabonylmethyl)piperazin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-(4-(carboxymethyl)piperazin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-(7-(pyrrolidin-1-yl)-6,7,8,9-tetrahydro-5H-benzo[7]annulene-1-yl)-1H-1,2,4-triazole-3,5-diamine;

1-(6,7-dihydro-5H-benzo[6,7]cyclohepta[1,2-c]pyridazin-3-yl)-N³-((7S)-7-amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7s)-7-(di(cyclopropylmethyl)amino)-6,7,8,9tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-((2-methylpropyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-((propyl)amino)-6,7,8,9-tetrahydro-5H-benzo[7]annulene-2-yl-1H-1,2,4 triazole-3,5-diamine;

1-(6,7-dihydro-5H-benzo[6,7]cyclohepta[1,2-c]pyridazin-3-yl)-N³-((7S)-7-(dipropylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(diethylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(cyclohexylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(cyclopentylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-((1-cyclopentylethyl)amino)-6,7,8,9tetrahydro-1H-benzo[7]annulene-2-yl-1H-1,2,4-triazole-3,5-diamine;

1-(6,7-dihydro-5H-benzo[6,7]cyclohepta[1,2-c]pyridazin-3-yl)-N³-((7S)-7-(2-propylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-((3,3-dimethylbut-2-yl)amino)-6,7,8,9-tetrahydro-5H-benzo[7]annulene-2-yl)-1H-1,2,4-triazole-3,5-diamine;

1-(6,7-dihydro-1H-benzo[6,7]cyclohepta[1,2-c]pyridazin-3-yl)-N³-((7S)-7-((cyclohexylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(di(cyclohexylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-((5-chlorothien-2-yl)methyl)amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-((2-carboxyphenyl)methyl)amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-((3-bromophenyl)methyl)amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(dimethylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(cyclobutylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(3-pentylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-((2,2-dimethylpropyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(di(cyclopentylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-((cyclopentylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(di(bicyclo[2.2.1]hept-2-en-5-ylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-((bicyclo[2.2.1]hept-2-en-5-ylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(3-methylbutylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(di(3-methylbutyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(2-ethylbutylamino)-6,7,8,9 tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(but-2-enylamino)-6,7,8,9tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N³-((7S)-7-(butyl(but-2-enyl)amino)-6,7,8,9-tetrahydro-5H-benzo[7]annulene-2-yl)-1H-1,2,4-triazole-3,5-diamine;

1-(6,7-dihydro-5H-pyrido[2',3':6,7]cyclohepta[1,2-c]pyridazin-3-yl)-N³-((7S)-7-(t-butoxycarbonylamino)-6,7,8,9-tetrahydro-5H-benzo[7]annulene-2-yl)-1H-1,2,4-triazole-3,5-diamine;

1-(6,7-dihydro-5H-pyrido[2',3':6,7]cyclohepta[1,2-c]pyridazin-3-yl)-N³-((7S)-7-amino-6,7,8,9-tetrahydro-5H-benzo[7]annulene-2-yl)-1H-1,2,4-triazole-3,5-diamine;

1-(6,7-dihydro-5H-pyrido[2',3':6,7]cyclohepta[1,2-c]pyridazin-3-yl)-N³-((7S)-7-(dimethylamino)-6,7,8,9-tetrahydro-5H-benzo[7]annulene-2-yl)-1H-1,2,4-triazole-3,5-diamine;

1-(6,7-dihydro-5H-pyrido[2',3':6,7]cyclohepta[1,2-c]pyridazin-3-yl)-N³-((7S)-7-(diethylamino)-6,7,8,9-tetrahydro-5H-benzo[7]annulene-2-yl)-1H-1,2,4-triazole-3,5-diamine;

1-(6,7-dihydro-5H-pyrido[2',3':6,7]cyclohepta[1,2-c]pyridazin-3-yl)-N³-((7S)-7-(dipropylamino)-6,7,8,9-tetrahydro-5H-benzo[7]annulene-2-yl)-1H-1,2,4-triazole-3,5-diamine;

1-(6,7-dihydro-5H-pyrido[2',3':6,7]cyclohepta[1,2-c]pyridazin-3-yl)-N³-((7S)-7-(di(cyclopropylmethyl)amino)-6,7,8,9-tetrahydro-5H-benzo[7]annulene-2-yl)-1H-1,2,4-triazole-3,5-diamine;

1-(6,7-dihydro-5H-pyrido[2',3':6,7]cyclohepta[1,2c]pyridazin-3-yl)-N³-((7S)-7-(di(3-methylbutyl)amino)-6,7,8,9-tetrahydro-5H-benzo[7]annulene-2-yl)-1H-1,2,4-triazole-3,5-diamine;

1-(6,7-dihydro-5H-pyrido[2',3':6,7]cyclohepta[1,2-c]pyridazin-3-yl)-N³-((7S)-7-(cyclobutylamino)-6,7,8,9-tetrahydro-5H-benzo[7]annulene-2-yl)-1H-1,2,4-triazole-3,5-diamine;

1-(6,7-dihydro-5H-pyrido[2',3':6,7]cyclohepta[1,2-c]pyridazin-3-yl)-N³-((7S)-7-(cyclohexylamino)-6,7,8,9-tetrahydro-5H-benzo[7]annulene-2-yl)-1H-1,2,4-triazole-3,5-diamine;

1-(6,7-dihydro-5H-pyrido[2',3:6,7]cyclohepta[1,2-c]pyridazin-3-yl)-N³-((7S)-7-((methylethyl)amino)-6,7,8,9-tetrahydro-5H-benzo[7]annulene-2-yl)-1H-1,2,4-triazole-3,5-diamine;

1-(6,7-dihydro-5H-pyrido[2',3':6,7]cyclohepta[1,2-c]pyridazin-3-yl)-N³-((7S)-7-(cyclopentylamino)-6,7,8,9-tetrahydro-5H-benzo[7]annulene-2-yl)-1H-1,2,4-triazole-3,5-diamine; and 1-(6,7-dihydro-5H-pyrido[2',3': 6,7]cyclohepta[1,2-c]pyridazin-3-yl)-N³-((7S)-7-(2-butylamino)-6,7,8,9-tetrahydro-5H-benzo[7]annulene-2-yl)-1H-1,2,4-triazole-3,5-diamine.

Another embodiment is the use where, in the compound of formula (Ia) as set forth above:

$R^1$, $R^4$ and $R^5$ are each independently hydrogen;

$R^2$ is heteroaryl optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—$OR^{12}$, —$R^{13}$—OC(O)—$R^{12}$, —$R^{13}$—O—$R^{14}$—N($R^{12}$)$_2$, —$R^{13}$—N($R^{12}$)—$R^{14}$—N($R^{12}$)$_2$, —$R^{13}$—N($R^{12}$)$_2$, —$R^{13}$—C(O)$R^{12}$, —$R^{13}$—C(O)OR$^{12}$, —$R^{13}$—C(O)N($R^{12}$)$_2$, —$R^{13}$—C(O)N($R^{12}$)—$R^{13}$—N($R^{12}$)$R^{13}$, —$R^{13}$—C(O)N($R^{12}$)—$R^{14}$—OR$^{12}$, —$R^{13}$—N($R^{12}$)C(O)OR$^{12}$, —$R^{13}$—N($R^{12}$)C(O)$R^{12}$, —$R^{13}$—N($R^{12}$)S(O)$_t R^{12}$ (where t is 1 or 2), —$R^{13}$—S(O)$_t$OR$^{12}$ (where t is 1 or 2), —$R^{13}$—S(O)$_p R^{12}$ (where p is 0, 1 or 2), and —$R^{13}$—S(O)$_t$N($R^{12}$)$_2$ (where t is 1 or 2), $R^3$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—O—$R^{10}$—$OR^8$, —$R^9$—O—$R^{10}$—O—$R^{10}$—$OR^8$, —$R^9$—O—$R^{10}$—C(O)

OR$^8$, —R$^9$—O—R$^{10}$—C(O)N(R$^6$)R$^7$, —R$^9$—O—R$^{10}$—S(O)$_p$R$^8$ (where p is 0, 1 or 2), —R$^9$—O—R$^{10}$—N(R$^6$)R$^7$, —R$^9$—O—R$^{10}$—C(NR$^{11}$)N(R$^{11}$)H, —R$^9$—OC(O)—R$^8$, —R$^9$—N(R$^6$)R$^7$, —R$^9$—C(O)R$^8$, —R$^9$—C(O)OR$^{12}$, —R$^9$—C(O)N(R$^6$)R$^7$, —R$^9$—N(R$^6$)C(O)OR$^8$, —R$^9$—N(R$^6$)C(O)R$^8$, —R$^9$—N(R$^6$)S(O)$_t$R$^8$ (where t is 1 or 2), —R$^9$—S(O)$_p$OR$^8$ (where p is 1 or 2), —R$^9$—S(O)$_t$R$^8$ (where t is 0, 1 or 2); and each R$^6$, each R$^7$, each R$^8$, each R$^9$, each R$^{12}$, each R$^{13}$ and each R$^{14}$ are as described above for compounds of formula (Ia); and each R$^6$, each R$^7$, each R$^8$, each R$^9$, each R$^{10}$, each R$^{11}$, each R$^{12}$, each R$^{13}$ and each R$^{14}$ are as described above for compounds of formula (Ia).

Another embodiment is the use where, in the compound of formula (Ia) as set forth above:

R$^2$ is heteroaryl selected from the group consisting of pyridinyl, pyrimidinyl, 4,5-dihydro-1H-benzo[b]azepin-2(3H)n-8-yl, benzo[d]imidazolyl, 6,7,8,9-tetrahydro-5H-pyrido[3,2-d]azepin-3-yl, 6,7,8,9-tetrahydro-5H-pyrido[3,2-c]azepin-3-yl, 5,6,7,8-tetrahydro-1,6-naphthyridin-3-yl, 5,6,7,8-tetrahydroquinolin-3-yl, 1,2,3,4-tetrahydroisoquinolin-7-yl, 2,3,4,5-tetrahydrobenzo[b]oxepin-7-yl, 3,4-dihydro-2H-benzo[b][1,4]dioxepin-7-yl, benzo[d]oxazol-5-yl, 3,4-dihydro-2H-benzo[b][1,4]oxazin-7-yl, benzo[b]thiophenyl, and 6,7,8,9-tetrahydro-5H-cyclohepta[b]pyridin-3-yl, each optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl, optionally substituted heteroarylalkenyl, —R$^{13}$—OR$^{12}$, —R$^{13}$—OC(O)—R$^{12}$, —R$^{13}$—O—R$^{14}$—N(R$^{12}$)$_2$, —R$^{13}$—N(R$^{12}$)$_2$, —R$^{13}$—C(O)R$^{12}$, —R$^{13}$—C(O)OR$^{12}$, —R$^{13}$—C(O)N(R$^{12}$)$_2$, —R$^{13}$—C(O)N(R$^{12}$)—R$^{14}$—N(R$^2$)R$^{13}$, —R$^{13}$—C(O)N(R$^{12}$)—R$^{14}$—OR$^{12}$, —R$^{13}$—N(R$^{12}$)C(O)OR$^{12}$, —R$^{13}$—N(R$^{12}$)C(O)R$^2$, —R$^{13}$—N(R$^{12}$)S(O)$_t$R$^{12}$ (where t is 1 or 2), —R$^{13}$—S(O)OR$^{12}$ (where t is 1 or 2), —R$^{13}$—S(O)$_p$R$^{12}$ (where p is 0, 1 or 2), and —R$^{13}$—S(O)$_t$N(R$^{12}$)$_2$ (where t is 1 or 2); and R$^3$ is a polycyclic heteroaryl containing more than 14 ring atoms selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-1-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro(cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro(cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substitutents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R$^9$—OR$^8$, —R$^9$—OC(O)—R$^8$, —R$^9$—N(R$^6$)R$^7$, —R$^9$—C(O)R$^8$, —R$^9$—C(O)OR$^8$, —R$^9$—C(O)N(R$^6$)R$^7$, —R$^9$—N(R$^6$)C(O)OR$^{12}$, —R$^9$—N(R$^6$)C(O)R$^8$, —R$^9$—N(R$^6$)S(O)$_t$R$^8$ (where t is 1 or 2), —R$^9$—S(O)$_t$OR$^8$ (where t is 1 or 2), —R$^9$—S(O)$_p$R$^8$ (where p is 0, 1 or 2), and —R$^9$—S(O)$_t$N(R$^6$)R$^7$ (where t is 1 or 2).

Another embodiment is the use where, in the compound of formula (Ia) as set forth above:

R$^2$ is selected from the group consisting of pyridinyl and pyrimidinyl, each optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl, optionally substituted heteroarylalkenyl, —R$^{13}$—OR$^{12}$, —R$^{13}$—OC(O)—R$^{12}$, —R$^{13}$—O—R$^{14}$—N(R$^{12}$)$_2$, —R$^{13}$—N(R$^{12}$)$_2$, —R$^{13}$—C(O)R$^{12}$, —R$^{13}$—C(O)OR$^{12}$, —R$^{13}$—C(O)N(R$^{12}$)$_2$, —R$^{13}$—C(O)N(R$^{12}$)—R$^{14}$—N(R$^{12}$)R$^{13}$, —R$^{13}$—C(O)N(R$^{12}$)—R$^{14}$—OR$^{12}$, —R$^{13}$—N(R$^{12}$)C(O)OR$^{12}$, —R$^{13}$—N(R$^{12}$)C(O)R$^{12}$, —R$^{13}$—N(R$^{12}$)S(O)$_t$R$^{12}$ (where t is 1 or 2), —R$^{13}$—S(O)OR$^{12}$ (where t is 1 or 2), —R$^{13}$—S(O)$_p$R$^{12}$ (where p is 0, 1 or 2), and —R$^{13}$—S(O)$_t$N(R$^{12}$)$_2$ (where t is 1 or 2).

Another embodiment is the use where the compound of formula (Ia), as set forth above, is selected from the group consisting of:

1-(6,7-dihydro-5H-benzo[6,7]cyclohepta[1,2-c]pyridazin-3-yl)-N$^3$-(6-(4-(bicyclo[2.2.1]heptan-2-yl)piperazin-1-yl)pyridin-3-yl)-1H-1,2,4-triazole-3,5-diamine;

1-(6,7-dihydro-5H-benzo[6,7]cyclohepta[1,2-c]pyridazin-3-yl)-N$^3$-(6-(4-cyclopentyl-1,4-diazepan-1-yl)pyridin-3-yl)-1H-1,2,4-triazole-3,5-diamine;

1-(6,7-dihydro-5H-benzo[6,7]cyclohepta[1,2-c]pyridazin-3-yl)-N$^3$-(6-(4-methylpiperazin-1-yl)pyridin-3-yl)-1H-1,2,4-triazole-3,5-diamine;

1-(6,7-dihydro-5H-benzo[6,7]cyclohepta[1,2-c]pyridazin-3-yl)-N$^J$-(6-(4-(4-methylpiperazin-1-yl)piperidin-1-yl)pyridine-3-yl)-1H-1,2,4-triazole-3,5-diamine;

1-(6,7-dihydro-5H-benzo[6,7]cyclohepta[1,2-c]pyridazin-3-yl)-N$^3$-(pyridin-3-yl)-1H-1,2,4-triazole-3,5-diamine;

1-(6,7-dihydro-5H-benzo[6,7]cyclohepta[1,2-c]pyridazin-3-yl)-N$^3$-(6-(6-aminopyridin-3-yl)pyridine-3-yl)-1H-1,2,4-triazole-3,5-diamine;

1-(6,7-dihydro-5H-benzo[6,7]cyclohepta[1,2-c]pyridazin-3-yl)-N$^3$-(6-(3-aminophenyl)pyridine-3-yl)-1H-1,2,4-triazole-3,5-diamine;

1-(6,7-dihydro-5H-benzo[6,7]cyclohepta[1,2-c]pyridazin-3-yl)-N$^3$-(6-(3-cyanophenyl)pyridine-3-yl)-1H-1,2,4-triazole-3,5-diamine;

1-(6,7-dihydro-5H-benzo[6,7]cyclohepta[1,2-c]pyridazin-3-yl)-N$^3$-(6-(benzo[d][1,3]dioxole-6-yl)pyridine-3-yl)-1H-1,2,4-triazole-3,5-diamine;

1-(6,7-dihydro-5H-benzo[6,7]cyclohepta[1,2-c]pyridazin-3-yl)-N$^3$-(6-(3-methylsulfonamidylphenyl)pyridine-3-yl)-1H-1,2,4-triazole-3,5-diamine;

1-(6,7-dihydro-5H-benzo[6,7]cyclohepta[1,2-c]pyridazin-3-yl)-N$^3$-(6-(2-diethylaminomethyl)pyrrolidin-1-yl)pyridin-3-yl)-N$^3$-1H-1,2,4-triazole-3,5-diamine;
1-(6,7-dihydro-5H-benzo[6,7]cyclohepta[1,2-c]pyridazin-3-yl)-N$^3$-(6-(3-diethylaminopyrrolidin-1-yl)pyridin-3-yl)-1H-1,2,4-triazole-3,5-diamine;
1-(6,7-dihydro-5H-benzo[6,7]cyclohepta[1,2-c]pyridazin-3-yl)-N$^3$-(6-(3-(4-(N-methylpiperazin-4-yl)piperidin-1-yl)-(E)-propenyl)pyridin-3-yl)-1H-1,2,4-triazole-3,5-diamine;
1-(6,7-dihydro-5H-benzo[6,7]cyclohepta[1,2-c]pyridazin-3-yl)-N$^3$-(6-(4-(pyrrolidin-1-yl)piperidin-1-yl)-5-methylpyridin-3-yl)-1H-1,2,4-triazole-3,5-diamine;
1-(6,7-dihydro-5H-benzo[6,7]cyclohepta[1,2-c]pyridazin-3-yl)-N$^3$-(6-(3-piperidin-1-yl-(E)-propenyl)pyridin-3-yl)-1H-1,2,4-triazole-3,5-diamine;
1-(6,7-dihydro-5H-benzo[6,7]cyclohepta[1,2-c]pyridazin-3-yl)-N$^3$-(6-(4-(bicyclo[2.2.1]heptan-2-yl)-1,4-diazepan-1-yl)pyridin-3-yl)-1H-1,2,4-triazole-3,5-diamine;
1-(6,7-dihydro-5H-benzo[6,7]cyclohepta[1,2-c]pyridazin-3-yl)-N$^3$-(6-(3-(4-(pyrrolidin-1-yl)piperidin-1-yl)-(E)-propenyl)pyridin-3-yl)-1H-1,2,4-triazole-3,5-diamine;
1-(6,7-dihydro-5H-benzo[6,7]cyclohepta[1,2-c]pyridazin-3-yl)-N$^3$-(6-(3-piperidin-1-yl)-propanylpyridin-3-yl)-11-1,2,4triazole-3,5-diamine;
1-(6,7-dihydro-5H-benzo[6,7]cyclohepta[1,2-c]pyridazin-3-yl) N$^3$-(6-(3-(4-(piperidin-1-yl)piperidin-1-yl)-(E)-propenyl)pyridin-3-yl)-1H-1,2,4-triazole-3,5-diamine;
1-(6,7-dihydro-5H-benzo[6,7]cyclohepta[1,2-c]pyridazin-3-yl)-N$^3$-(6-(3-(4-dimethylaminopiperidin-1-yl)-(E)-propenyl)pyridin-3-yl)-1H-1,2,4-triazol-3,5-diamine;
1-(6,7-dihydro-5H-benzo[6,7]cyclohepta[1,2-c]pyridazin-3-yl)-N$^3$-(2-(4-pyrolidin-1-yl)piperidin-1-yl)pyrimidin-5-yl)-1H-1,2,4-triazole-3,5-diamine;
1-(6,7-dihydro-5H-benzo[6,7]cyclohepta[1,2-c]pyridazin-3-yl)-N$^3$-(2-(4-(piperidin-1-ylmethyl)piperidin-1-yl)pyrimidin-5-yl)-1H-1,2,4-triazole-3,5-diamine;
1-(6,7-dihydro-5H-benzo[6,7]cyclohepta[1,2-c]pyridazin-3-yl)-N$^3$-(6-((4-piperidin-1-ylpiperidin-1-yl)carbonyl)pyridin-3-yl)-1H-1,2,4-triazole-3,5-diamine;
1-(6,7-dihydro-5H-benzo[6,7]cyclohepta[1,2-c]pyridazin-3-yl)-N$^3$-(2-(4-cyclopropylmethylpiperazin-1-yl)pyridine-5-yl)-1H-1,2,4-triazole-3,5-diamine; and
1-(6,7-dihydro-5H-benzo[6,7]cyclohepta[1,2-c]pyridazin-3-yl)-N$^3$-(2-(3-(S)-methyl-4-cyclopropylmethylpiperazin-1-yl)pyridine-5-yl)-1H-1,2,4-triazole-3,5-diamine.

Another embodiment is the use where, in the compound of formula (Ia) as set forth above:

R$^1$, R$^4$ and R$^5$ are each independently hydrogen;
R$^2$ is selected from the group consisting of 4,5-dihydro-1H-benzo[b]azepin-2(3H)-on-8-yl, benzo[d]imidazolyl, 6,7,8,9-tetrahydro-5H-pyrido[3,2-d]azepin-3-yl, 6,7,8,9-tetrahydro-5H-pyrido[3,2-c]azepin-3-yl, 5,6,7,8-tetrahydro-1,6-naphthyridin-3-yl, 5,6,7,8-tetrahydroquinolin-3-yl, 1,2,3,4-tetrahydroisoquinolin-7-yl, 2,3,4,5-tetrahydrobenzo[b]oxepin-7-yl, 3,4-dihydro-2H-benzo[b][1,4]dioxepin-7-yl, benzo[d]oxazol-5-yl, 3,4-dihydro-2H-benzo[b][1,4]oxazin-7-yl, benzo[b]thiophenyl, and 6,7,8,9-tetrahydro-5H-cyclohepta[b]pyridin-3-yl, each optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl, optionally substituted heteroarylalkenyl, —R$^{13}$—OR$^{12}$, —R$^{13}$—OC(O)—R$^{12}$, —R$^{13}$—O—R$^{14}$—N(R$^{12}$)$_2$, —R$^{13}$—N(R$^2$)$_2$, —R$^{13}$—C(O)R$^{12}$, —R$^{13}$—C(O)OR$^{12}$, —R$^{13}$—C(O)N(R$^{12}$)$_2$, —R$^{13}$—C(O)N(R$^{12}$)—R$^{14}$—N(R$^{12}$)R$^{13}$, —R$^{13}$—C(O)N(R$^{12}$)—R$^{14}$—OR$^{12}$, —R$^{13}$—N(R$^{12}$)C(O)OR$^{12}$, —R$^{13}$—N(R$^{12}$)C(O)R$^{12}$, —R$^{13}$—N(R$^{12}$)S(O)$_t$R$^{12}$ (where t is 1 or 2), —R$^{13}$—S(O)$_t$OR$^{12}$ (where t is 1 or 2), —R$^{13}$—S(O)$_p$R$^{12}$ (where p is 0, 1 or 2), and —R$^3$—S(O)$_t$N(R$^{12}$)$_2$ (where t is 1 or 2); and
R$^3$ is a polycyclic heteroaryl containing more than 14 ring atoms selected from the group consisting of 6,7-dihydro-5H-benzo[6,7]cyclohepta[2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-1-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro(cycloocta[b]pyridine-7,2'-[1,3]dioxolane)-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro(cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R$^9$—OR$^8$, —R$^9$—OC(O)—R$^8$, —R$^9$—N(R$^6$)R$^7$, —R$^9$—C(O)R$^8$, —R$^9$—C(O)OR$^8$, —R$^9$—C(O)N(R$^6$)R$^7$, —R$^9$—N(R$^6$)C(O)OR$^{12}$, —R$^9$—N(R$^6$)C(O)R$^8$, —R$^9$—N(R$^6$)S(O)$_t$R$^8$ (where t is 1 or 2), —R$^9$—S(O)$_t$OR$^8$ (where t is 1 or 2), —R$^9$—S(O)$_p$R$^8$ (where p is 0, 1 or 2), and —R$^9$—S(O)$_t$N(R$^6$)R$^7$ (where t is 1 or 2).

Another embodiment is the use where the compound of formula (Ia), as set forth above, is selected from the group consisting of:

1-(6,7-dihydro-5H-benzo[6,7]cyclohepta[1,2-c]pyridazin-3-yl)-N$^3$-(4,5-dihydro-1H-benzo[b]azepin-2(3H)-on-S-yl)-1H-1,2,4-triazole-3,5-diamine;
1-(6,7-dihydro-5H-benzo[6,7]cyclohepta[1,2-c]pyridazin-3-yl)-N$^3$-(2-(dimethylaminomethyl)-1H-benzo[d]imidazol-5-yl)-1H-1,2,4-triazole-3,5-diamine;
1-(6,7-dihydro-5H-benzo[6,7]cyclohepta[1,2-c]pyridazin-3-yl)-N$^3$-(7-cyclopentyl-6,7,8,9-tetrahydro-5H-pyrido[3,2-d]azepin-3-yl)-1H-1,2,4-triazole-3,5-diamine;
1-(6,7-dihydro-5H-benzo[6,7]cyclohepta[1,2-c]pyridazin-3-yl)-N$^3$-(6-methyl-5,6,7,8-tetrahydro-1,6-naphthyridin-3-yl)-1H-1,2,4-triazole-3,5-diamine;
1-(6,7-dihydro-5H-benzo[6,7]cyclohepta[1,2-c]pyridazin-3-yl)-N$^3$-(6-(4-(4-methylpiperazin-1-yl)piperidin-1-yl)pyridine-3-yl)-1H-1,2,4-triazole-3,5-diamine;
1-(6,7-dihydro-5H-benzo[6,7]cyclohepta[1,2-c]pyridazin-3-yl)-N$^3$-(6-(4-methylpiperazin-1-yl)carbonyl-5,6,7,8-tetrahydroquinolin-3-yl)-1H-1,2,4-triazole-3,5-diamine, compound #31, 1H-1,2,4-triazole-3,5-diamine;

1-(6,7-dihydro-5H-benzo[6,7]cyclohepta[1,2-c]pyridazin-3-yl)-N³-(2,3,4,5-tetrahydrobenzo[b]oxepin-7-yl)-1H-1,2,4-triazole-3,5-diamino;
1-(6,7-dihydro-5H-benzo[6,7]cyclohepta[1,2-c]pyridazin-3-yl)-N³-(3,4-dihydro-2H-benzo[b,f][1,4]dioxepin-7-yl)-1H-1,2,4-triazole-3,5-diamine;
1-(6,7-dihydro-5H-benzo[2,3]oxepino[4,5-c]pyridazin-3-yl)-N³-(2-(pyrrolidin-1-ylmethyl)benzo(d]oxazol-5-yl)-1H-1,2,4-triazole-3,5-diamine;
1-(6,7-dihydro-5H-benzo[6,7]cyclohepta[1,2-c]pyridazin-3-yl)-N³-(4-(2-dimethylaminoethyl)-(3,4-dihydro-2H-benzo[b,f][1,4]oxazin-7-yl)-1H-1,2,4-triazole-3,5-diamine;
1-(6,7-dihydro-5H-benzo[2,3]oxepino[4,5-c]pyridazin-3-yl)-N³-(4-(2-dimethylaminoethyl)-(3,4-dihydro-2H-benzo[b,f][1,4]oxazin-7-yl))-1H-1,2,4-triazole-3,5-diamine;
1-(6,7-dihydro-5H-benzo[2,3]thiepino[4,5-c]pyridazin-3-yl)-N³-(2-(I-(4-(2-(dimethylamino)ethyl)piperazin-1-yl)oxomethyl)benzo[b]thiophen-5-yl)-1H-1,2,4-triazole-3,5-diamine;
1-(6,7-dihydro-5H-benzo[6,7]cyclohepta[1,2-c]pyridazin-3-yl)-N³-(6-cyclopentyl-6,7,8,9-tetrahydro-5H-pyrido[3,2-c]azepin-3-yl)-1H-1,2,4-triazole-3,5-diamine;
1-(6,7-dihydro-5H-benzo[6,7]cyclohepta[1,2-c]pyridazin-3-yl)-N³-((7-pyrrolidin-1-yl)-6,7,8,9-tetrahydro-5H-cyclohepta[b]pyridine-3-yl)-1H-1,2,4-triazole-3,5-diamine;
1-(6,7-dihydro-5H-benzo[6,7]cyclohepta[1,2-c]pyridazin-3-yl)-N³-(2-cyclopentyl-1,2,3,4-tetrahydroisoquinolin-7-yl)-1H-1,2,4-triazole-3,5-diamine;
1-(6,7-dihydro-5H-benzo[6,7]cyclohepta[1,2-c]pyridazin-3-yl)-N³-(6-(pyrrolidin-1-yl)-5,6,7,8-tetrahydroquinolin-3-yl)-1H-1,2,4-triazole-3,5-diamine;
1-(6,7-dihydro-5H-benzo[6,7]cyclohepta[1,2-c]pyridazin-3-yl)-N³-(6-cyclopentyl-5,6,7,8-tetrahydro-1,6-naphthyridine-3-yl)-1H-1,2,4-triazole-3,5-diamine;
1-(6,7-dihydro-5H-benzo[6,7]cyclohepta[1,2-c]pyridazin-3-yl)-N³—((S)-7-(pyrrolidin-1-yl)-6,7,8,9-tetrahydro-5H-cyclohepta[b]pyridine-3-yl)-1H-1,2,4-triazole-3,5-diamine;
1-(6,7-dihydro-5H-benzo[6,7]cyclohepta[1,2-c]pyridazin-3-yl)-N³-(1,2,3,4-tetrahydroisoquinolin-7-yl)-1H-1,2,4-triazole-3,5-diamine;
1-(6,7-dihydro-5H-benzo[6,7]cyclohepta[1,2-c]pyridazin-3-yl)-N³-(2-(1-methylpiperidin-4-yl)-1,2,3,4-tetrahydroisoquinolin-7-yl)-1H-1,2,4-triazole-3,5-diamine; and
1-(6,7-dihydro-5H-benzo[6,7]cyclohepta[1,2-c]pyridazin-3-yl)-N³-(2-(cyclopropylmethyl)-1,2,3,4-tetrahydroisoquinolin-7-yl)-1H-1,2,4-triazole-3,5-diamine.

Another embodiment is the use where the compound of formula (Ia), as set forth above, is a compound of formula (Ia1):

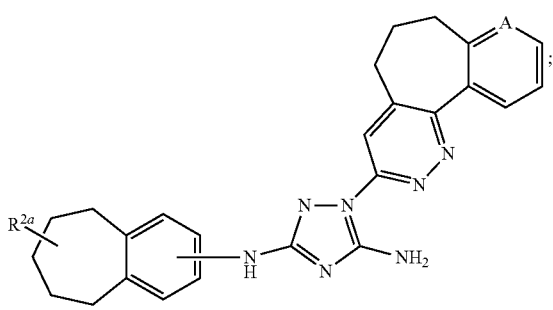

(Ia1)

wherein:
A is =C(H)— or =N—;
each $R^{2a}$ is independently selected from the group consisting of —N(R$^{12a}$)$_2$ and —N(R$^{12a}$)C(O)R$^{12a}$,
or $R^{2a}$ is an N-heterocyclyl optionally substituted by one or more substituents selected from the group consisting of halo and —R$^{21}$—C(O)OR$^{20}$,
each $R^{12a}$ is independently selected from the group consisting of hydrogen, alkyl, alkenyl, optionally substituted aralkyl, optionally substituted cycloalkyl, optionally substituted cycloalkylalkyl, optionally substituted heteroaryl and optionally substituted heteroarylalkyl;
$R^{20}$ is independently selected from the group consisting of hydrogen, alkyl, alkenyl, optionally substituted aralkyl, optionally substituted cycloalkyl, optionally substituted cycloalkylalkyl, optionally substituted heteroaryl and optionally substituted heteroarylalkyl; and
$R^{21}$ is independently selected from the group consisting of a direct bond or an optionally substituted straight or branched alkylene chain;
as an isolated stereoisomer or mixture thereof, or a pharmaceutically acceptable salt thereof.

Another embodiment is wherein the compound of formula (I) is a compound of formula (Ib):

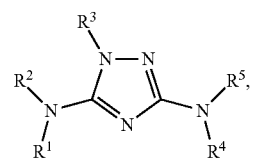

(Ib)

wherein $R^1$, $R^2$, $R^3$, $R^4$ and $R^5$ are as described above for compounds of formula (I), as an isolated stereoisomer or mixture thereof or as a tautomer or mixture thereof, or a pharmaceutically acceptable salt or N-oxide thereof.

Another embodiment is the use where, in the compound of formula (Ib) as set forth above, $R^2$ and $R^3$ are each independently a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R$^9$—OR$^8$, —R$^9$—O—R$^{10}$—OR$^8$, —R$^9$—O—R$^{10}$—O—R$^{10}$—OR$^8$, —R$^9$—O—R$^{10}$—C(O)OR$^8$, —R$^9$—O—R$^{10}$—C(O)N(R$^6$)R$^7$, —R$^9$—O—R$^{10}$—S(O)$_p$R$^8$ (where p is 0, 1 or 2), —R$^9$—O—R$^{10}$—N(R$^6$)R$^7$, —R$^9$—O—R$^{10}$—C(NR$^{11}$)N(R$^{11}$)H, —R$^9$—OC(O)—R$^8$, —R$^9$—N(R$^6$)R$^7$, —R$^9$—C(O)R$^8$, —R$^9$—C(O)OR$^8$, —R$^9$—C(O)N(R$^6$)R$^7$, —R$^9$—N(R$^6$)C(O)OR$^8$, —R$^9$—N(R$^6$)C(O)R$^8$, —R$^9$—N(R$^6$)S(O)$_t$R$^8$ (where t is 1 or 2), —R$^9$—S(O)$_t$OR$^8$ (where t is 1 or 2), —R$^9$—S(O)$_p$R$^8$ (where p is 0, 1 or 2), and —R$^9$—S(O)$_t$N(R$^6$)R$^7$ (where t is 1 or 2); and $R^1$, $R^4$, $R^5$, each $R^6$, each $R^7$, each $R^8$, each $R^9$, each $R^{10}$, each $R^{11}$ and $R^{12}$ are as described above in relation to formula (I).

Another embodiment is the use where, in the compound of formula (Ib) as set forth above:
$R^1$, $R^4$ and $R^5$ are each hydrogen;
each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—CN, —$R^{10}$—$NO_2$, —$R^{10}$—$N(R^8)_2$, —$R^{10}$—C(O)$OR^8$ and —$R^{10}$—C(O)N$(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain; and each $R^{11}$ is independently selected from the group consisting of hydrogen, alkyl, cyano, nitro and —$OR^8$.

Another embodiment is the use where, in the compound of formula (Ib) as set forth above:

$R^2$ and $R^3$ are each independently a polycyclic heteroaryl containing more than 14 ring atoms selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—OC(O)—$R^8$, —$R^9$—$N(R^6)R^7$, —$R^9$—C(O)$R^8$, —$R^9$—C(O)$OR^8$, —$R^9$—C(O)N$(R^6)R^7$, —$R^9$—$N(R^6)$C(O)$OR^{12}$, —$R^9$—$N(R^6)$C(O)$R^8$, —$R^9$—$N(R^6)$S(O)$_tR^8$ (where t is 1 or 2), —$R^9$—S(O)$_tOR^8$ (where t is 1 or 2), —$R^9$—S(O)$_pR^8$ (where p is 0, 1 or 2), and —$R^9$—S(O)$_tN(R^6)R^7$ (where t is 1 or 2)

Another embodiment is the use where the compound of formula (Ib), as set forth above, is 1-(6,7-dihydro-5H-benzo[6,7]cyclohepta[1,2-c]pyridazin-3-yl)-$N^3$-(5,7,8,9-tetrahydrospiro[cyclohepta[b]pyridine-6,2' [1,3]dioxolane-3-yl)-1H-1,2,4-triazole-3,5-diamine.

Another embodiment is the use where, in the compound of formula (Ib) as set forth above:

$R^2$ is selected from the group consisting of aryl and heteroaryl, where the aryl and the heteroaryl are each independently optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—$OR^{12}$, —$R^{13}$—OC(O)—$R^{12}$, —$R^{13}$—O—$R^{14}$—$N(R^2)_2$, —$R^{13}$—$N(R^{12})_2$, —$R^{13}$—C(O)$R^{12}$, —$R^{13}$—C(O)$OR^{12}$, —$R^{13}$—C(O)N$(R^{12})_2$, —$R^{13}$—C(O)N$(R^{12})$—$R^{14}$—$N(R^{12})R^{13}$, —$R^{13}$—C(O)N$(R^{12})$—$R^{14}$—$OR^2$, —$R^{13}$—$N(R^{12})$C(O)$OR^2$, —$R^{13}$—N$(R^{12})$C(O)$R^{12}$, —$R^{13}$—$N(R^{12})$S(O)$_tR^{12}$ (where t is 1 or 2), —$R^{13}$—S(O)$_tOR^{12}$ (where t is 1 or 2), —$R^{13}$—S(O)$_pR^{12}$ (where p is 0, 1 or 2), and —$R^{13}$—S(O)$_tN(R^{12})_2$ (where t is 1 or 2); and $R^3$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—O—$R^{10}$—$OR^8$, —$R^9$—O—$R^{10}$—O—$R^{10}$—$OR^8$, —$R^9$—O—$R^{10}$—C(O)$OR^8$, —$R^9$—O—$R^{10}$—C(O)N$(R^6)R^7$, —$R^9$—O—$R^{10}$—S(O)$_pR^8$ (where p is 0, 1 or 2), —$R^9$—O—$R^{10}$—$N(R^6)R^7$, —$R^9$—O—$R^{10}$—C(N$R^{11}$)N($R^{11}$)H, —$R^9$—OC(O)—$R^8$, —$R^9$—$N(R^6)R^7$, —$R^9$—C(O)$R^8$, —$R^9$—C(O)$OR^8$, —$R^9$—C(O)N$(R^6)R^7$, —$R^9$—$N(R^6)$C(O)$OR^{12}$, —$R^9$—$N(R^6)$C(O)$R^8$, —$R^9$—$N(R^6)$S(O)$_tR^8$ (where t is 1 or 2), —$R^9$—S(O)$_tOR^8$ (where t is 1 or 2), —$R^9$—S(O)$_pR^8$ (where p is 0, 1 or 2), and —$R^9$—S(O)$_tN(R^6)R^7$ (where t is 1 or 2).

Another embodiment is the use where, in the compound of formula (Ib) as set forth above:

$R^1$, $R^4$ and $R^5$ are each independently hydrogen;

each $R^6$ and $R^7$ is independently selected from the group consisting of hydrogen, alkyl, alkenyl, alkynyl, haloalkyl, hydroxyalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^{10}$—$OR^8$, —$R^{10}$—CN, —$R^{10}$—$NO_2$, —$R^{10}$—$N(R^8)_2$, —$R^{10}$—C(O)$OR^8$ and —$R^{10}$—C(O)N$(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, and optionally substituted heteroarylalkyl;

each $R^9$ is independently selected from the group consisting of a direct bond and an optionally substituted straight or branched alkylene chain;

each $R^{10}$ is an optionally substituted straight or branched alkylene chain;

each $R^{11}$ is independently selected from the group consisting of hydrogen, alkyl, cyano, nitro and —$OR^8$;

each $R^{12}$ is independently selected from the group consisting of hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl and optionally substituted heteroarylalkyl, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond and an optionally substituted straight or branched alkylene chain; and each $R^{14}$ is an optionally substituted straight or branched alkylene chain.

Another embodiment is the use where, in the compound of formula (Ib) as set forth above:

$R^2$ is aryl optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—$OR^{12}$, —$R^{13}$—OC(O)—$R^2$, —$R^{13}$—O—$R^{14}$—$N(R^{12})_2$, —$R^{14}$—$N(R^{12})_2$, —$R^3$—C(O)$R^{12}$, —$R^{13}$—C(O)$OR^{12}$, —$R^{13}$—C(O)$N(R^{12})_2$, —$R^{13}$—C(O)$N(R^2)$—$R^{14}$—$N(R^{12})R^{13}$, —$R^{13}$—C(O)$N(R^{12})$—$R^{14}$—$OR^{12}$, —$R^{13}$—$N(R^{12})C(O)OR^{12}$, —$R^{13}$—$N(R^{12})C(O)R^{12}$, —$R^{13}$—$N(R^{12})S(O)_tR^{12}$ (where t is 1 or 2), —$R^{13}$—$S(O)_tOR^{12}$ (where t is 1 or 2), —$R^{13}$—$S(O)_pR^{12}$ (where p is 0, 1 or 2), and —$R^{13}$—$S(O)_tN(R^2)_2$ (where t is 1 or 2); and $R^3$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—O—$R^{10}$—$OR^8$, —$R^9$—O—$R^{10}$—O—$R^{10}$—$OR^8$, —$R^9$—O—$R^{10}$—C(O)$OR^8$, —$R^9$—O—$R^{10}$—C(O)$N(R^6)R^7$, —$R^9$—O—$R^{10}$—$S(O)_pR^8$ (where p is 0, 1 or 2), —$R^9$—O—$R^{10}$—$N(R^6)R^7$, —$R^9$—O—$R^{10}$—$C(NR^{11})N(R^{11})H$, —$R^9$—OC(O)—$R^8$, —$R^9$—$N(R^6)R^7$, —$R^9$—C(O)$R^8$, —$R^9$—C(O)$OR^{12}$, —$R^9$—C(O)$N(R^6)R^7$, —$R^9$—$N(R^6)C(O)OR^8$, —$R^9$—$N(R^6)C(O)R^8$, —$R^9$—$N(R^6)S(O)_tR^8$ (where t is 1 or 2), —$R^9$—$S(O)_pOR^8$ (where p is 1 or 2), —$R^9$—$S(O)_tR^8$ (where t is 0, 1 or 2);

Another embodiment is the use where, in the compound of formula (Ib) as set forth above:

$R^1$, $R^4$ and $R^5$ are each independently hydrogen;

$R^2$ is aryl selected from the group consisting of phenyl and 6,7,8,9-tetrahydro-5H-benzo[7]annulene-2-yl, each optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—$OR^{12}$, —$R^{13}$—OC(O)—$R^{12}$, —$R^{13}$—O—$R^{14}$—$N(R^{12})_2$, —$R^{13}$—$N(R^{12})_2$, —$R^{13}$—C(O)$R^{12}$, —$R^{13}$—C(O)$OR^{12}$, —$R^{13}$—C(O)$N(R^{12})_2$, —$R^{13}$—C(O)$N(R^{12})$—$R^4$—$N(R^{12})R^{13}$, —$R^{13}$—C(O)$N(R^{12})$—$R^{14}$—$OR^{12}$, —$R^{13}$—$N(R^{12})C(O)OR^{12}$, —$R^{13}$—$N(R^{12})C(O)R^{12}$, —$R^{13}$—$N(R^{12})S(O)_tR^{12}$ (where t is 1 or 2), —$R^{13}$—$S(O)OR^{12}$ (where t is 1 or 2), —$R^{13}$—$S(O)_pR^{12}$ (where p is 0, 1 or 2), and —$R^{13}$—$S(O)_tN(R^{12})_2$ (where t is 1 or 2); and $R^3$ is a polycyclic heteroaryl containing more than 14 ring atoms selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-1 l-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—OC(O)—$R^8$, —$R^9$—$N(R^6)R^7$, —$R^9$—C(O)$R^8$, —$R^9$—C(O)$OR^8$, —$R^9$—C(O)$N(R^6)R^7$, —$R^9$—$N(R^6)C(O)OR^{12}$, —$R^9$—$N(R^6)C(O)R^8$, —$R^9$—$N(R^6)S(O)_tR^8$ (where t is 1 or 2), —$R^9$—$S(O)_tOR^8$ (where t is 1 or 2), —$R^9$—$S(O)_pR^8$ (where p is 0, 1 or 2), and —$R^9$—$S(O)_tN(R^6)R^7$ (where t is 1 or 2).

Another embodiment is the use where, in the compound of formula (Ib) as set forth above:

$R^2$ is phenyl optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl, optionally substituted heteroarylalkenyl, —$R^{13}$—$OR^{12}$, —$R^{13}$—OC(O)—$R^{12}$, —$R^{13}$—O—$R^{14}$—$N(R^{12})_2$, —$R^{13}$—$N(R^{12})_2$, —$R^{13}$—$C(O)R^{12}$, —$R^{13}$—$C(O)OR^{12}$, —$R^{13}$—$C(O)N(R^{12})_2$, —$R^{13}$—$C(O)N(R^{12})$—$R^{14}$—$N(R^{12})R^{13}$, —$R^{13}$—$C(O)N(R^{12})$—$R^{14}$—$OR^{12}$, —$R^{13}$—$N(R^{12})C(O)OR^{12}$, —$R^{13}$—$N(R^{12})C(O)R^{12}$, —$R^{13}$—$N(R^{12})S(O)_tR^{12}$ (where t is 1 or 2), —$R^{13}$—$S(O)_tOR^{12}$ (where t is 1 or 2), —$R^{13}$—$S(O)_pR^{12}$ (where p is 0, 1 or 2), and —$R^{13}$—$S(O)_tN(R^{12})_2$ (where t is 1 or 2).

Another embodiment is the use where the compound of formula (Ib), as set forth above, is selected from the group consisting of:

1-(6,7-dihydro-5H-benzo[6,7]cyclohepta[1,2-c]pyridazin-3-yl)-$N^5$-(3-fluoro-4-(4-(indolin-2-on-1-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-$N^5$-(3-fluoro-4-(4-(morpholin-4-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-$N^5$-(4-(3,5-dimethylpiperazin-1-yl)phenyl)-1H-1,2,4-triazole-3,5-diamine;

1-(7-methyl-6,7-dihydro-5H-benzo[2,3]azepino[4,5-c]pyridazin-3-yl)-$N^5$-(4-(N-methylpiperazin-1-yl)phenyl)-1H-1,2,4-triazole-3,5-diamine;

1-(6,7-dihydro-5H-benzo[6,7]cyclohepta[1,2-c]pyridazin-3-yl)-$N^5$-(4-((5-fluoroindolin-2-on-3-yl)methyl)phenyl)-1H-1,2,4-triazole-3,5-diamine;

1-(6,7-dihydro-5H-benzo[6,7]cyclohepta[1,2-c]pyridazin-3-yl)-$N^5$-(4-(4-pyrrolidin-1-ylpiperidinyl)phenyl)-1H-1,2,4-triazole-3,5-diamine;

1-(6,7-dihydro-5H-benzo[6,7]cyclohepta[1,2-c]pyridazin-3-yl)-$N^5$-(4-((4-pyrrolidin-1-ylpiperidinyl)methyl)phenyl)-1H-1,2,4-triazole-3,5-diamine;

1-(6,7-dihydro-5H-benzo[6,7]cyclohepta[1,2-c]pyridazin-3-yl)-$N^5$-(4-((4-cyclopentylpiperazinyl)methyl)phenyl)-1H-1,2,4-triazole-3,5-diamine;

1-(6,7-dihydro-5H-benzo[6,7]cyclohepta[1,2-c]pyridazin-3-yl)-$N^5$-(4-((4-isopropylpiperazinyl)methyl)phenyl)-1H-1,2,4-triazole-3,5-diamine;

1-(6,7-dihydro-5H-benzo[6,7]cyclohepta[,2-c]pyridazin-3-yl)-$N^5$-(3-fluoro-4-(4-N-methylpiperid-4-ylpiperazinyl)phenyl)-1H-1,2,4-triazole-3,5-diamine;

1-(6,7-dihydro-5H-benzo[6,7]cyclohepta[1,2c]pyridazin-3-yl)-$N^5$-(3-fluoro-4-(7-methyl-2,7-diazaspiro[4.4]nonan-2-yl)phenyl)-1H-1,2,4-triazole-3,5-diamine;

1-(6,7-dihydro-5H-benzo[6,7]cyclohepta[1,2-c]pyridazin-3-yl)-$N^5$-(3-fluoro-4-(3-pyrrolidin-1-ylazetidinyl)phenyl)-1H-1,2,4-triazole-3,5-diamine;

1-(6,7-dihydro-5H-benzo[6,7]cyclohepta[1,2-c]pyridazin-3-yl)-$N^5$-(3-methyl-4-(4-(N-methylpiperazin-4-yl)piperidin-1-yl)phenyl)-1H-1,2,4-triazole-3,5-diamine;

1-(6,7-dihydro-5H-benzo[2,3]thiepino[4,5-c]pyridazin-3-yl)-$N^5$-(4-(4-pyrrolidin-1-ylpiperidinyl)phenyl)-1H-1,2,4-triazole-3,5-diamine;

1-(6,7-dihydro-5H-benzo[6,7]cyclohepta[1,2-c]pyridazin-3-yl)-$N^5$-(3-fluoro-(4-(3-pyrrolidin-1-yl)pyrrolidin-1-yl)phenyl)-1H-1,2,4-triazole-3,5-diamine;

1-(6,7-dihydro-5H-benzo[6,7]cyclohepta[1,2-c]pyridazin-3-yl)-$N^5$-(3-fluoro-4-(4-methylpiperazin-1-yl)phenyl)-1H-1,2,4-triazole-3,5-diamine; and 1-(6,7-dihydro-5H-benzo[6,7]cyclohepta[1,2-c]pyridazin-3-yl)-$N^3$-(3-fluoro-4-(4-cyclopropylmethylpiperazin-1-yl)phenyl)-1H-1,2,4-triazole-3,5-diamine.

Another embodiment is the use where, in the compound of formula (Ib) as set forth above:

$R^1$, $R^4$ and R are each independently hydrogen;

$R^2$ is 6,7,8,9-tetrahydro-5H-benzo[7]annulene-2-yl optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl, optionally substituted heteroarylalkenyl, —$R^{13}$—$OR^{12}$, —$R^{13}$—$OC(O)$—$R^{12}$, —$R^{13}$—O—$R^{14}$—$N(R^{12})_2$, —$R^{13}$—$N(R^{12})_2$, —$R^{13}$—$C(O)R^{12}$, —$R^{13}$—$C(O)OR^{12}$, —$R^{13}$—$C(O)N(R^{12})_2$, —$R^{13}$—$C(O)N(R^{12})$—$R^{14}$—$N(R^{12})R^{13}$, —$R^{13}$—$C(O)N(R^{12})$—$R^{14}$—$OR^{12}$, —$R^{13}$—$N(R^{12})C(O)OR^{12}$, —$R^{13}$—$N(R^{12})C(O)R^{12}$, —$R^{13}$—$N(R^{12})S(O)_tR^{12}$ (where t is 1 or 2), —$R^{13}$—$S(O)_tOR^{12}$ (where t is 1 or 2), —$R^{13}$—$S(O)_pR^{12}$ (where p is 0, 1 or 2), and —$R^{13}$—$S(O)_tN(R^{12})_2$ (where t is 1 or 2); and $R^3$ is a polycyclic heteroaryl containing more than 14 ring atoms selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c)pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro(benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—OC(O)—$R^8$, —$R^9$—N($R^6$)$R^7$, —$R^9$—$C(O)R^8$, —$R^9$—$C(O)OR^8$, —$R^9$—$C(O)N(R^6)R^7$, —$R^9$—$N(R^6)C(O)OR^{12}$, —$R^9$—$N(R^6)C(O)R^8$, —$R^9$—$N(R^6)S(O)_tR^8$ (where t is 1 or 2), —$R^9$—$S(O)_tOR^8$ (where t is 1 or 2), —$R^9$—$S(O)_pR^8$ (where p is 0, 1 or 2), and —$R^9$—$S(O)_tN(R^6)R^7$ (where t is 1 or 2).

Another embodiment is the use where the compound of formula (Ib), as set forth above, is selected from the group consisting of:

1-(6,7-dihydro-5H-benzo[6,7]cyclohepta[1,2-c]pyridazin-3-yl)-$N^5$-(7-(pyrrolidin-1-yl)-6,7,8,9-tetrahydro-5H-benzo[7]annulene-1-yl)-1H-1,2,4-triazole-3,5-diamine;

1-(6,7-dihydro-5H-benzo[6,7]cyclohepta[1,2-c]pyridazin-3-yl)-$N^5$-((7S)-7-(t-butoxycarbonylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^5$-(7-((bicyclo[2.2.1]heptan-2-yl)(methyl)amino)-6,7,8,9-tetrahydro-5H-benzo[7]annulene-2-yl)-1H-1,2,4-triazole-3,5-diamine; and 1-(6,7-dihydro-5H-benzo[6,7]cyclohepta[1,2-c]pyridazin-3-yl)-$N^5$-(7-(S)-pyrrolidin-1-yl-6,7,8,9-tetrahydro-5H-benzo[7]annulen-2-yl)-1H-1,2,4-triazole-3,5-diamine.

Another embodiment is the use where, in the compound of formula (Ib) as set forth above:

$R^1$, $R^4$ and $R^5$ are each independently hydrogen;

$R^2$ is heteroaryl optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—$OR^{12}$, —$R^{13}$—OC(O)—$R^{12}$, —$R^{13}$—O—$R^{14}$—N($R^{12}$)$_2$, —$R^{13}$—N($R^{12}$)$_2$, —$R^{13}$—C(O)$R^{12}$, —$R^{13}$—C(O)O$R^{12}$, —$R^{12}$—C(O)N($R^2$)$_2$, —$R^{13}$—C(O)N($R^{12}$)$_2$, —$R^{13}$—C(O)N($R^{12}$)—$R^{14}$—N($R^{12}$)$R^{13}$, —$R^{13}$—C(O)N($R^{12}$)—$R^{14}$—O$R^{12}$, —$R^{13}$—N($R^{12}$)C(O)O$R^{12}$, —$R^{13}$—N($R^{12}$)C(O)$R^{12}$, —$R^{13}$—N($R^{12}$)S(O)$_t$$R^{12}$ (where t is 1 or 2), —$R^{13}$—S(O)$_t$O$R^{12}$ (where t is 1 or 2), —$R^{13}$—S(O)$_p$$R^{12}$ (where p is 0, 1 or 2), and —$R^{13}$—S(O)$_1$N($R^2$)$_2$ (where t is 1 or 2); and $R^3$ is a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—O—$R^{10}$—$OR^8$, —$R^9$—O—$R^{10}$—O—$R^{10}$—$OR^8$, —$R^9$—O—$R^{10}$—C(O)$OR^8$, —$R^9$—O—$R^{10}$—C(O)N($R^6$)$R^7$, —$R^9$—O—$R^{10}$—S(O)$_p$$R^8$ (where p is 0, 1 or 2), —$R^9$—O—$R^{10}$—N($R^6$)$R^7$, —$R^9$—O—$R^{10}$—C(N$R^{11}$)N($R^{11}$)H, —$R^9$—OC(O)—$R^8$, —$R^9$—N($R^6$)$R^7$, —$R^9$—C(O)$R^8$, —$R^9$—C(O)$OR^8$, —$R^9$—C(O)N($R^6$)$R^7$, —$R^9$—N($R^6$)C(O)O$R^{12}$, —$R^9$—N($R^6$)C(O)$R^8$, —$R^9$—N($R^6$)S(O)$_t$$R^8$ (where t is 1 or 2), —$R^9$—S(O)$_t$O$R^8$ (where p is 1 or 2), —$R^9$—S(O)$_t$$R^8$ (where t is 0, 1 or 2);

Another embodiment is the use where, in the compound of formula (Ib) as set forth above:

$R^2$ is heteroaryl selected from the group consisting of pyridinyl, pyrimidinyl, 4,5-dihydro-1H-benzo[b]azepin-2(3H)-on-8-yl, benzo[d]imidazolyl, 6,7,8,9-tetrahydro-5H-pyrido[3,2-d]azepin-3-yl, 6,7,8,9-tetrahydro-5H-pyrido[3,2-c]azepin-3-yl, 5,6,7,8-tetrahydro-1,6-naphthyridin-3-yl, 5,6,7,8-tetrahydroquinolin-3-yl, 1,2,3,4-tetrahydroisoquinolin-7-yl, 2,3,4,5-tetrahydrobenzo[b]oxepin-7-yl, 3,4-dihydro-2H-benzo[b][1,4]dioxepin-7-yl, benzo[d]oxazol-5-yl, 3,4-dihydro-2H-benzo[b][1,4]oxazin-7-yl, benzo[b]thiophenyl, and 6,7,8,9-tetrahydro-5H-cyclohepta[b]pyridin-3-yl, each optionally substituted by one or more substitutents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted cycloalkyl, optionally substituted cycloalkylalkyl, optionally substituted cycloalkylalkenyl, optionally substituted heterocyclyl, optionally substituted heterocyclylalkyl, optionally substituted heterocyclylalkenyl, optionally substituted heteroaryl, optionally substituted heteroarylalkyl, optionally substituted heteroarylalkenyl, —$R^{13}$—$OR^{12}$, —$R^{13}$—OC(O)—$R^{12}$, —$R^{13}$—O—$R^{14}$—N($R^{12}$)$_2$, —$R^{13}$—N($R^{12}$)$_2$, —$R^{13}$—C(O)$R^{12}$, —$R^{13}$—C(O)O$R^{12}$, —$R^{13}$—C(O)N($R^{12}$)$_2$, —$R^{13}$—C(O)N($R^{12}$)—$R^{14}$—N($R^{12}$)$R^{13}$, —$R^{13}$—C(O)N($R^2$)—$R^{14}$—O$R^{12}$, —$R^{13}$—N($R^{12}$)C(O)O$R^{12}$, —$R^{13}$—N($R^{12}$)C(O)$R^{12}$, —$R^{13}$—N($R^{12}$)S(O)$_t$$R^{12}$ (where t is 1 or 2), —$R^{13}$—S(O)$_t$O$R^{12}$ (where t is 1 or 2), —$R^{13}$—S(O)$_p$$R^{12}$ (where p is 0, 1 or 2), and —$R^{13}$—S(O)$_t$N($R^{12}$)$_2$ (where t is 1 or 2), and $R^3$ is a polycyclic heteroaryl containing more than 14 ring atoms selected from the group consisting of 6,7-dihydro-5H-benzo[6,7]cyclohepta[1,2-c]pyridazin-3-yl, 6,7,8,9-tetrahydro-5H-cyclohepta[4,5]thieno[2,3-d]pyrimidin-4-yl, 6,7-dihydro-5H-benzo[6,7]cyclohepta[1,2-d]pyrimidin-4-yl, 6,7-dihydro-5H-benzo[2,3]azepino[4,5-c]pyridazin-3-yl, (Z)-dibenzo[b,f][1,4]thiazepin-11-yl, 6,7-dihydro-5H-benzo[6,7]cyclohepta[4,5-c]pyridazin-2-yl, 6,7-dihydro-5H-benzo[2,3]oxepino[4,5-c]pyridazin-3-yl, spiro[chromeno[4,3-c]pyridazine-5,1'-cyclopentane]-3-yl, 6,8,9,10-tetrahydro-5H-spiro[cycloocta[b]pyridine-7,2'-[1,3]dioxolane]-3-yl, 5,6,8,9-tetrahydrospiro[benzo[7]annulene-7,2'-[1,3]dioxolane]-3-yl, 5,7,8,9-tetrahydrospiro[cyclohepta[b]pyridine-6,2'-[1,3]dioxolane]-3-yl, 6,7-dihydro-5H-benzo[2,3]thiepino[4,5-c]pyridazin-3-yl, 6,7-dihydro-5H-benzo[6,7]cyclohepta[1,2-d]pyrimidin-2-yl, 5,6,8,9-tetrahydrospiro[cyclohepta[b]pyridine-7,2'-[1,3]dioxolane]-3-yl, 6,8,9,10-tetrahydro-5H-spiro[cycloocta[b]pyridine-7,2'-[1,3]dioxane]-3-yl and 6,7-dihydro-5H-benzo[6,7]cyclohepta[1,2-b]pyridin-2-yl, each optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —$R^9$—$OR^8$, —$R^9$—OC(O)—$R^8$, —$R^9$—N($R^6$)$R^7$, —$R^9$—C(O)$R^8$, —$R^9$—C(O)O$R^8$, —$R^9$—C(O)N($R^6$)$R^7$, —$R^9$—N($R^6$)C(O)O$R^{12}$, —$R^9$—N($R^6$)C(O)$R^8$, —$R^9$—N($R^6$)S(O)$_t$$R^8$ (where t is 1 or 2), —$R^9$—S(O)$_t$O$R^8$ (where t is 1 or 2), —$R^9$—S(O)$_p$$R^8$ (where p is 0, 1 or 2), and —$R^9$—S(O)$_t$N($R^6$)$R^7$ (where t is 1 or 2).

Another embodiment is the use where the compound of formula (Ib), as set forth above, is selected from the group consisting of:

1-(6,7-dihydro-5H-benzo[6,7]cyclohepta[1,2-c]pyridazin-3-yl)-$N^5$-(6-(4-(pyrrolidin-1-yl)piperidin-1-yl)-5-methylpyridin-3-yl)-1H-1,2,4-triazole-3,5-diamine;

1-(6,7-dihydro-5H-benzo[6,7]cyclohepta[1,2-c]pyridazin-3-yl)-$N^5$-(4-(3,5-dimethylpiperazin-1-yl)phenyl)-1H-1,2,4-triazole-3,5-diamine;

1-(6,7-dihydro-5H-benzo[6,7]cyclohepta[1,2-c]pyridazin-3-yl)-$N^5$-(1,2,3,4-tetrahydroisoquinolin-7-yl)-1H-1,2,4-triazole-3,5-diamine; and 1-(6,7-dihydro-5H-benzo[6,7]cyclohepta[1,2-c]pyridazin-3-yl)-$N^5$-(2-(1-methylpiperidin-4-yl)-1,2,3,4-tetrahydroisoquinolin-7-yl)-1H-1,2,4-triazole-3,5-diamine.

Another embodiment is the use where the compound of formula (Ib), as set forth above, is a compound of formula (Ib 1):

(Ib1)

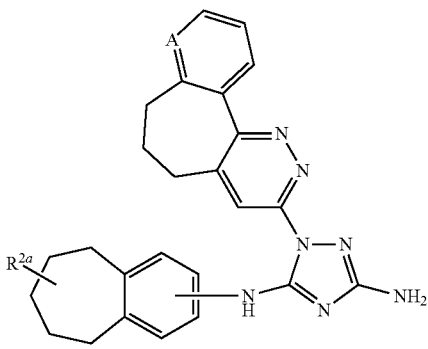

wherein:
A is =C(H)— or =N—;
  each $R^{2a}$ is independently selected from the group consisting of —$N(R^{12a})_2$ and —$N(R^{12a})C(O)R^{12a}$,
or $R^{2a}$ is an N-heterocyclyl optionally substituted by one or more substituents selected from the group consisting of halo and —$R^{21}$—$C(O)OR^{20}$,
each $R^{12a}$ is independently selected from the group consisting of hydrogen, alkyl, alkenyl, optionally substituted aralkyl, optionally substituted cycloalkyl, optionally substituted cycloalkylalkyl, optionally substituted heteroaryl and optionally substituted heteroarylalkyl;
$R^{20}$ is independently selected from the group consisting of hydrogen, alkyl, alkenyl, optionally substituted aralkyl, optionally substituted cycloalkyl, optionally substituted cycloalkylalkyl, optionally substituted heteroaryl and optionally substituted heteroarylalkyl; and
$R^{21}$ is independently selected from the group consisting of a direct bond or an optionally substituted straight or branched alkylene chain;
as an isolated stereoisomer or mixture thereof, or a pharmaceutically acceptable salt thereof.

Preferably, the Axl inhibitor is 1-(6,7-dihydro-5H-benzo[6,7]cyclohepta[1,2-c]pyridazin-3-yl)-$N^3$-((7-(S)-pyrrolidin-1-yl)-6,7,8,9-tetrahydro-5H-benzo[7]annulene-2-yl)-1H-1,2,4-triazole-3,5-diamine.

In one embodiment of the use in preventing, treating or managing cancer in a patient, the one or more immune checkpoint (activity) modulators are selected from the group consisting of anti-CTLA-4 antibodies, anti-PD-1 antibodies, anti-PD-L1 antibodies, anti-4-1BB antibodies, anti-OX-40 antibodies, anti-GITR antibodies, anti-CD27 antibodies, anti-CD28 antibodies, anti-CD40 antibodies, anti-LAG3 antibodies, anti-ICOS antibodies, anti-TWEAKR antibodies, anti-HVEM antibodies, anti-TIM-1 antibodies, anti-TIM-3 antibodies, anti-VISTA antibodies, and anti-TIGIT antibodies.

Preferably, the one or more immune checkpoint (activity) modulators are selected from the group consisting of anti-CTLA-4 antibodies, anti-PD-1 antibodies, anti-PD-L1 antibodies, anti-4-1BB antibodies, anti-OX-40 antibodies, anti-GITR antibodies, anti-CD27 antibodies, anti-CD40 antibodies, and anti-LAG3 antibodies.

For example, specific immune checkpoint (activity) modulators include ipilimumab, tremelimumab, pembrolizumab, nivolumab, and urelumab, and those which can be identified by the drug candidate identifliors AMP-514/MEDIO680 (MedImmune/AstraZeneca), MPDL3280A (Genentech/Roche), MEDI4736 (MedImmune/AstraZeneca), MSB0010718C (EMD Serono), BMS-936559 (Bristol-Myers Squibb), PF-05082566 (Pfizer), MEDI6469 (MedImmune/AstraZeneca), MEDI6383 (rOX40L; MedImmune/AstraZeneca), MOXR0916 (Genentech/Roche), TRX518 (Tolerx), CDX-1127 (Celldex), CP-870,893 (Genentech/Roche), and BMS-986016 (Bristol-Myers Squibb) (preferably ipilimumab, tremelimumab, pembrolizumab, and nivolumab).

In a preferred embodiment, one or more of the immune checkpoint (activity) modulators is an immune checkpoint inhibitor, i.e. an agent which acts at T cell co-inhibitory receptors, such as CTLA-4, PD-1, PD-L1, BTLA, TIM-3, VISTA, LAG-3, and TIGIT.

In an alternative preferred embodiment, one or more of the immune checkpoint (activity) modulators is an agent which acts at T cell co-stimulatory receptors, such as CD28, ICOS, 4-1BB, OX40, GITR, CD27, TWEAKR, HVEM, and TIM-1.

In another alternative preferred embodiment, one or more of the immune checkpoint (activity) modulators is an agent which acts at dendritic cell co-stimulatory receptors, such as CD40 and 4-1BB.

In a particularly preferred embodiment of the invention, two or more immune checkpoint (activity) modulators are employed in conjunction with the Axl inhibitor. Results have shown that an improved synergistic effect can be obtained when at least two different immune checkpoint (activity) modulators are employed, especially when such immune checkpoint (activity) modulators act at different cell receptor sub-types. For example, the combination of at least one immune checkpoint inhibitor and at least one T cell co-stimulatory receptor agonist or dendritic cell co-stimulatory receptor agonist.

Preferably, at least one of the two immune checkpoint (activity) modulators is an anti-CTLA-4 antibody or an anti-PD-1 antibody. In particular, the combination of an anti-CTLA-4 antibody and an anti-PD-1 antibody has proven to be particularly effective.

In terms of administration, the Axl inhibitor may be administered to the patient, preferably a human, in an amount of between about 1 mg/kg and about 100 mg/kg twice a day, preferably between about 5 mg/kg and about 80 mg/kg twice a day, even more preferably between about 5 mg/kg and about 25 mg/kg twice a day, and the chemotherapeutic agent is administered to the mammal in an amount of between about 1.0 mg/kg and about 10.0 mg/kg once a week, preferably between about 1.0 mg/kg and about 5 mg/kg once a week, even more preferably between about 1.0 mg/kg and 2.0 mg/kg once a week.

In the combination therapies of the invention, an Axl inhibitor is used as an active ingredient in combination with one or more immune checkpoint (activity) modulators in the prevention, treatment or management of one or more cancers. The term "combination therapy" includes simultaneous or sequential administration of the Axl inhibitor and the one or more immune checkpoint (activity) modulators, in any order, such as administering the Axl inhibitor at the same time as the administration of the one or more immune checkpoint (activity) modulators, before the administration of the one or more immune checkpoint (activity) modulators or after the administration of the one or more immune checkpoint (activity) modulators (preferably, the Axl inhibitor is administered before the one or more immune checkpoint (activity) modulators). Unless the context makes clear otherwise, "combination therapy" may include the administration of dosage forms of an Axl inhibitor combined with the dosage forms of one or more immune checkpoint (activity) modulators. Unless the context makes clear otherwise, "combination therapy" may include different routes of administration for the Axl inhibitor and for the one or more immune checkpoint (activity) modulators. Dosage forms, routes of administration and pharmaceutical compositions include, but are not limited to, those described herein.

Axl inhibitors (particularly the compounds of formula (I), as defined above) are small molecule inhibitors of Axl catalytic activity, and are therefore useful in treating diseases and conditions which are associated with Axl catalytic activity, which includes cancer and metastatic cancer. In particular, diseases and conditions which are alleviated by the modulation of Axl activity include, but are not limited to, solid cancer tumors, including, but not limited to, breast, renal, endometrial, bladder, ovarian, thyroid, and non-small cell lung carcinoma, melanoma, prostate carcinoma, sarcoma, gastric cancer and uveal melanoma, and liquid tumors, including but not limited to, leukemias (particularly myeloid leukemias) and lymphomas.

In addition to the foregoing, Axl inhibitors are useful in treating diseases and conditions which are affected by the following biological processes: invasion, migration, metastasis, or drug resistance as manifested in cancer, and stem cell biology as manifested in cancer.

Similarly, immune checkpoint (activity) modulators have been implicated for use in the same conditions.

When a cancer spreads (metastasises) from its original site (primary tumor) to another area of the body, it is termed "metastatic cancer". Virtually all cancers have the potential to spread this way.

The treatment of metastatic cancer depends on where the primary tumor is located. When breast cancer spreads to the lungs, for example, it remains a breast cancer and the treatment is determined by the metastatic cancer origin within the breast, not by the fact that it is now in the lung. About 5 percent of the time, metastatic cancer is discovered but the primary tumor cannot be identified. The treatment of these metastatic cancers is dictated by their location rather than their origin. Metastatic cancers are named by the tissue of the original tumor (if known). For example, a breast cancer that has spread to the lung is called metastatic breast cancer to the lung.

Metastases spread in three ways: by local extension from the tumor to the surrounding tissues, through the bloodstream to distant sites or through the lymphatic system to neighboring or distant lymph nodes. Each kind of cancer may have a typical route of spread.

Tissues which are particularly susceptible to metastatic cancer are the brain, liver, bone and lung, although all tissues of the body may be affected. Any cancer may spread to the brain, although the most common to do so are lung and breast cancer. The most common cancer to metastasize to the liver is colon or other gastrointestinal cancer. The most common cancers to spread to the bones are prostate, lung and breast cancer. Metastases to the lung are common for many types of cancer.

The combination therapies of the invention are also useful in treating certain cellular proliferative disorders. Such disorders include, but are not limited to, the following:

a) proliferative disorders of the breast, which include, but are not limited to, invasive ductal carcinoma, invasive lobular carcinoma, ductal carcinoma, lobular carcinoma in situ and metastatic breast cancer;

b) proliferative disorders of the skin, which include, but are not limited to, basal cell carcinoma, squamous cell carcinoma, malignant melanoma and Karposi's sarcoma;

c) proliferative disorders of the respiratory tract, which include, but are not limited to, small cell and non-small cell lung carcinoma, bronchial adema, pleuropulmonary blastoma and malignant mesothelioma;

d) proliferative disorders of the brain, which include, but are not limited to, brain stem and hyptothalamic glioma, cerebellar and cerebral astrocytoma, medullablastoma, ependymal tumors, oligodendroglial, meningiomas and neuroectodermal and pineal tumors;

e) proliferative disorders of the male reproductive organs, which include, but are not limited to, prostate cancer, testicular cancer and penile cancer;

f) proliferative disorders of the female reproductive organs, which include, but are not limited to, uterine cancer (endometrial), cervical, ovarian, vaginal, vulval cancers, uterine sarcoma and ovarian germ cell tumor;

g) proliferative disorders of the digestive tract, which include, but are not limited to, anal, colon, colorectal, esophageal, gallbladder, stomach (gastric), pancreatic cancer, pancreatic cancer-Islet cell, rectal, small-intestine and salivary gland cancers;

h) proliferative disorders of the liver, which include, but are not limited to, hepatocellular carcinoma, cholangiocarcinoma, mixed hepatocellular cholangiocarcinoma, primary liver cancer and metastatic liver cancer;

i) proliferative disorders of the eye, which include, but are not limited to, intraocular melanoma, retinoblastoma, and rhabdomyosarcoma;

j) proliferative disorders of the head and neck, which include, but are not limited to, laryngeal, hypopharyngeal, nasopharyngeal, oropharyngeal cancers, and lip and oral cancer, squamous neck cancer, metastatic paranasal sinus cancer;

k) proliferative disorders of lymphocytic cells, which include, but are not limited to, various T cell and B cell lymphomas, non-Hodgkins lymphoma, cutaneous T cell lymphoma, Hodgkins disease, and lymphoma of the central nervous system;

l) leukemias, which include, but are not limited to, acute myeloid leukemia, acute lymphoblastic leukemia, chronic lymphocytic leukemia, chronic myelogenous leukemia, and hairy cell leukemia, m) proliferative disorders of the thyroid, which include, but are not limited to, thyroid cancer, thymoma, malignant thymoma, medullary thyroid carcinomas, papillary thyroid carcinomas, multiple endocrine neoplasia type 2A (MEN2A), pheochromocytoma, parathyroid adenomas, multiple endocrine neoplasia type 2B (MEN2B), familial medullary thyroid carcinoma (FMTC) and carcinoids;

n) proliferative disorders of the urinary tract, which include, but are not limited to, bladder cancer;

o) sarcomas, which include, but are not limited to, sarcoma of the soft tissue, osteosarcoma, malignant fibrous histiocytoma, lymphosarcoma, and rhabdomyosarcoma;

p) proliferative disorders of the kidneys, which include, but are not limited to, renal cell carcinoma, clear cell carcinoma of the kidney; and renal cell adenocarcinoma;

q) precursor B-lymphoblastic leukemia/lymphoma (precursor B-cell acute lymphoblastic leukemia), B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma and Burkitt's lymphoma/Burkitt cell leukemia (r) precursor T-lymphoblastic lymphoma/leukemia (precursor T-cell acute lymphoblastic leukemia), T-cell prolymphocytic leukemia, T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, mycosis fungoides/Sezary syndrome, anaplastic large-cell lymphoma, T/null cell, primary cutaneous type, peripheral T-cell lymphoma, not otherwise characterized, angioimmunoblastic T-cell lymphoma, anaplastic large-cell lymphoma, T/null cell, and primary systemic type;

(s) nodular lymphocyte-predominant Hodgkin's lymphoma, nodular sclerosis Hodgkin's lymphoma (grades 1 and 2), lymphocyte-rich classical Hodgkin's lymphoma, mixed cellularity Hodgkin's lymphoma, and lymphocyte depletion Hodgkin's lymphoma;

(t) myelogenous leukemia (e.g., Philadelphia chromosome positive (t(9;22)qq34;q11)), multiple myeloma, chronic neutrophilic leukemia, chronic eosinophilic leukemia/hypereosinophilic syndrome, chronic idiopathic myelofibrosis, polycythemia vera, essential thrombocythemia, chronic myelomonocytic leukemia, atypical chronic myelogenous leukemia, juvenile myelomonocytic leukemia, refractory anemia with ringed sideroblasts and without ringed sideroblasts, refractory cytopenia (myelodysplastic syndrome) with multilineage dysplasia, refractory anemia (myelodysplastic syndrome) with excess blasts, Sq-syndrome, and myelodysplastic syndrome with t(9; 12)(q22; p12);

(u) AML with t(8;21)(q22;q22), AMLI(CBF-alpha)/ETO, acute promyelocytic leukemia (AML with t(15;17)(q22;q11-12) and variants, PML/RAR-alpha), AML with abnormal bone marrow eosinophils (inv(16)(p13q22) or t(16;16)(p13; q11), CBFb/MYHI IX), and AML with llq23 (MLL) abnormalities, AML minimally differentiated, AML without maturation, AML with maturation, acute myelomonocytic leukemia, acute monocytic leukemia, acute erythroid leukemia, acute megakaryocytic leukemia, acute basophilic leukemia, and acute panmyelosis with myelofibrosis.

In a preferred embodiment, the Axl inhibitor and the one or more immune checkpoint (activity) modulators are useful in preventing, treating and/or managing breast cancer, renal cancer, lung cancer, bladder cancer, prostate cancer, melanoma and/or lymphomas, and metastatic cancers (preferably breast cancer and metastatic breast cancer to the lung).

The antiproliferative effect of a combination therapy of the invention may be assessed by administering the active ingredients of the combination therapy to a cultured tumor cell line. In the context of an in vitro assay, administration of an active ingredient may be simply achieved by contacting the cells in culture with the active ingredient in amounts effective to inhibit cell proliferation. Alternatively, the antiproliferative effect of a combination therapy of the invention may be assessed by administering the active ingredients of the combination therapy to an animal in an approved in vive model for cell proliferation.

Examples of tumor cell lines derived from human tumors and available for use in the in vivo studies include, but are not limited to, leukemia cell lines (e.g., CCRF-CEM, HL-60 (TB), K-562, MOLT-4, RPM 1-8226, SR, P388 and P388/ADR); non-small cell lung cancer cell lines (e.g., A549/ATCC, EKVX, HOP-62, HOP-92, NCI-H226, NCI-H23, NCI-H322M, NCI-H460, NCI-H522 and LXFL 529); small cell lung cancer cell lines (e.g., DMS 114 and SHP-77); colon cancer cell lines (e.g., COLO 205, HCC-2998, HCT-116, HCT-15, HT29, KMI2, SW-620, DLD-1 and KM20L2); central nervous system (CNS) cancer cell lines (e.g., SF-268, SF-295, SF-539, SNB-19, SNB-75, U251, SNB-78 and XF 498); melanoma cell lines (e.g., LOX I MVI, MALME-3M, M14, SK-MEL-2, SK-MEL-28, SK-MEL-5, UACC-257, UACC-62, RPMI-7951 and M19-MEL); ovarian cancer cell lines (e.g., IGROVI, OVCAR-3, OVCAR-4, OVCAR-5, OVCAR-8 and SK-OV-3); renal cancer cell lines (e.g., 786-0, A498, ACHN, CAKI-1, RXF 393, SNI2C, TK-10, UO-31, RXF-631 and SNI2K1); prostate cancer cell lines (e.g., PC-3 and DU-145); breast cancer cell lines (e.g., MCF7, NCI/ADR-RES, MDA-MB-231/ATCC, HS 578T, MDA-MB-435, BT-549, T-47D and MDA-MB-468); and thyroid cancer cell lines (e.g., SK-N-SH).

The combination therapies of the invention can be tested for the treatment of leukemias and lymphomas by testing the combination therapy in the xenograft in SCID mouse model using human Axl-expressing cancer cell lines including, but not limited to, HeLa, MDA-MB-231, SK-OV-3, OVCAR-8, DU145, H1299, ACHN, A498 and Caki-1. In addition, the combination therapy may be tested for its use in treating leukemias in the xenograft in SCID or nu/nu mouse model using human Axl-expressing AML and CML leukemia cell lines.

The combination therapies of the invention may be tested for efficacy in preventing, treating or managing metastatic cancers in known animal models of metastatic cancer, such as the Mouse 4T1 Breast Tumor Model (see Pulaski, B. A. et al., *Current Protocols in Immunology* (2000), 20.2.1-20.2.16) or variations thereof.

Pharmaceutical compositions of Axl inhibitors and other agents are known or can be prepared according to methods known to one skilled in the art. For example, methods of preparing and formulating pharmaceutical compositions of the Axl inhibitors of formula (I), as defined above, are disclosed in PCT Published Patent Application No. 2008/083367, as well as methods of administration.

In general, the amount of an Axl inhibitor or the amount of one or more immune checkpoint (activity) modulators which will be effective in the treatment, prevention or management of cancer in the combination therapies of the invention can be determined by standard research techniques. For example, the dosage amount of each active ingredient in a combination therapy of the invention which will be effective in the treatment, prevention or management of cancer can be determined by administering the combination therapy to an animal model such as the ones described herein or by one known to one skilled in the art. In addition, in vivo assays may optionally be employed to help identify optimal dosage ranges of each active ingredient in a combination therapy of the invention.

Selection of the preferred prophylactically or therapeutically effective dose of an active ingredient used in the combination therapies of the invention can be determined (e.g., by clinical trials) by a skilled artisan based upon the consideration of several factors, including the activity of the specific compound employed; the metabolic stability and length of action of the compound; the age, body weight, general health, sex, and diet of the patient; the mode and time of administration; the rate of excretion; the drug combination; and the severity of the metastatic cancer.

The precise dose of either the Axl inhibitor or the immune checkpoint (activity) modulators used in the combination therapies of the invention will also depend on the route of administration and the seriousness of the cancer and should be decided according to the judgment of the medical practitioner and each patient's circumstances. Effective doses may be extrapolated from dose-response curves derived from in vitro or animal model test systems.

For example, a therapeutically effective daily dose for an Axl inhibitor, i.e., a compound of formula (I), as defined above, is (for a 70 kg mammal) from about 0.001 mg/kg (i.e., 0.07 mg) to about 100 mg/kg (i.e., 7.0 gm); preferably a therapeutically effective dose is (for a 70 kg mammal) from about 0.01 mg/kg (i.e., 0.7 mg) to about 50 mg/kg (i.e., 3.5 gm); more preferably a therapeutically effective dose is (for a 70 kg mammal) from about 1 mg/kg (i.e., 70 mg) to about 25 mg/kg (i.e., 1.75 gm).

Dosages, routes of administration and recommended usage of the immune checkpoint (activity) modulators used in the combination therapies of the invention are known in the art and often described in such literature as the Physician's Desk Reference (current edition). In addition, typical doses of immune checkpoint (activity) modulators may be the same as the Axl inhibitor as described above.

In the combination therapies of the invention, an Axl inhibitor is administered simultaneously with, prior to, or after administration of one or more immune checkpoint (activity) modulators, as described herein, by the same route of administration or by different routes. Such combination therapy includes administration of a single pharmaceutical dosage formulation which contains an Axl inhibitor and one or more additional immune checkpoint (activity) modulators, as well as administration of the Axl inhibitor and each immune checkpoint inhibitor in its own separate pharmaceutical dosage formulation. For example, the Axl inhibitor and the other one or more immune checkpoint (activity) modulators can be administered to the patient together in a single oral dosage composition such as a tablet or capsule, or each agent can be administered in separate oral dosage formulations. Where separate dosage formulations are used, the Axl inhibitor and the one or more immune checkpoint (activity) modulators can be administered to the patient at essentially the same time, i.e., concurrently, or at separately staggered times, i.e., sequentially. All such combinations of administration are encompassed by the combination therapies of the invention.

In certain embodiments of the combination therapies of the invention, the Axl inhibitor is administered to a patient, preferably a human, concurrently with one or more immune checkpoint (activity) modulators useful for the treatment of cancer. The term "concurrently" is not limited to the administration of the active ingredients (i.e., the Axl inhibitor and the one or more immune checkpoint (activity) modulators) at exactly the same time, but rather it is meant that the Axl inhibitor and the immune checkpoint (activity) modulators are administered to a patient in a sequence and within a time interval such that the Axl inhibitor can act together with the immune checkpoint (activity) modulators to provide an increased benefit than if they were administered otherwise. For example, each active ingredient of the combination therapies of the invention may be administered at the same time or sequentially in any order at different points in time; however, if not administered at the same time, they should be administered sufficiently close in time so as to provide the desired therapeutic or prophylactic effect. Each active ingredient can be administered separately, in any appropriate form and by any suitable route. In various embodiments, the active ingredients are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 1 hours apart, at about 11 hours to about 12 hours apart, no more than 24 hours apart or no more than 48 hours apart. In preferred embodiments, two or more active ingredients are administered within the same patient visit.

In other embodiments, the active ingredients are administered at about 2 to 4 days apart, at about 4 to 6 days apart, at about 1 week part, at about 1 to 2 weeks apart, or more than 2 weeks apart. In preferred embodiments, the active ingredients are administered in a time frame where both active ingredients are still prophylactically and therapeutically active. One skilled in the art would be able to determine such a time frame by determining the half life of the administered active ingredients.

In certain embodiments, the active ingredients of the invention are cyclically administered to a patient. Cycling therapy involves the administration of a first active ingredient, such as the Axl inhibitor, for a period of time, followed by the administration of the second and/or third active ingredient for a period of time and repeating this sequential administration. Cycling therapy can reduce the development of resistance to one or more of the therapies, avoid or reduce the side effects of one of the therapies, and/or improves the efficacy of the treatment.

In certain embodiments, the active ingredients are administered in a cycle of less than about 3 weeks, about once every two weeks, about once every 10 days or about once every week. One cycle can comprise the administration of an active ingredient by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In yet other embodiments, the active ingredients of the combination therapies of the invention are administered in metronomic dosing regimens, either by continuous infasion or frequent administration without extended rest periods. Such metronomic administration can involve dosing at constant intervals without rest periods.

In other embodiments, the active ingredients are administered concurrently to a patient such that doses of the immune checkpoint (activity) modulators are administered separately yet within a time interval such that the Axl inhibitor can work together with the immune checkpoint (actively) modulators. For example, the immune checkpoint (activity) modulator may be administered one time per week and the Axl inhibitor may be administered every day. In other words, the dosing regimens for the active ingredients are carried out concurrently even if the active ingredients are not administered simultaneously or within the same patient visit.

FIGURES

FIG. 1 shows the post-immune response tumour recurrence and metastasis in the mammary adenocarcinoma 4T1-Luc/Balb/C syngeneic mouse model. The top image shows control shRNA and the bottom image shows shAXL. Detected images are shown in the adjacent Table.

FIGS. 2A-B show body weight changes (BWC) in Balb/e mice carrying 4T1 orthotopic tumors treated with vehicle, 50 mg/kg BGD324 Did or 10 mg/kg CTLA-4/PD-1 (each) in combinations or alone as indicated over the course of 46 (a) or (b) 104 days. Means±SEM are plotted, n=4 (vehicle), 5 (BGB324), 9 (CTLA4/PD1+/−BGB324 and CTLA4-BGB324). The sudden drop in BWC in Group D at day 38 is due to euthanisation of mice.

FIGS. 3A-C show transformed survival curves of Balb/e mice carrying 4T orthotopic tumors treated with vehicle, BGB324 or CTLA-4/PD-1 alone or in combinations as indicated for 46 (a) or 104 (b and c) days. Endpoints for survival were set to the day when the tumor reached 500 mm$^3$. Significance by Mantel-Cox; *p<0.05; *p<0.01; *p<0.001; **p<0.0001; ns: not significant.

FIG. 4 shows tumor volumes at day 28 after treatment initiation of all tumors presented in FIGS. 3 (a-c).

FIG. 5 shows the combined transformed survival curves for two separate mouse experiments of Balb/c mice carrying 4T1 orthotopic tumors treated with vehicle, CTLA-4/PD-1 or CTLA-4/PD-1+BGB324. The studies combined in the survival curves are presented in FIG. 2 (Report 153-SR-502P1MS6.2_Ver2) and in Report 102-SR-324; data not presented individually here). Significance by Mantel-Cox.

FIG. 6 shows enhanced tumor infiltration of anti-tumorigenic Cytotoxic T cells (CTLs) in Balb/c mice carrying 4T1 orthotopic tumors treated with CTLA-4/PD-1+BGB324 compared to CTLA-4/PD1-alone. Tumors were analysed at day 11 after treatment initiation as described in legends to FIG. 1.

FIG. 7 shows enhanced presence of anti-tumorigenic Natural Killer cells, macrophages and Neutrophiles in spleens of Balb/c mice carrying 4T1 orthotopic tumors treated with CTLA-4/PD-1-1BGB324 compared to CTLA-4/PD-1 alone. Tumors were analysed at day 11 after treatment initiation as described in legends to FIG. 1. Significance by one-way ANOVA.

Figure 10:
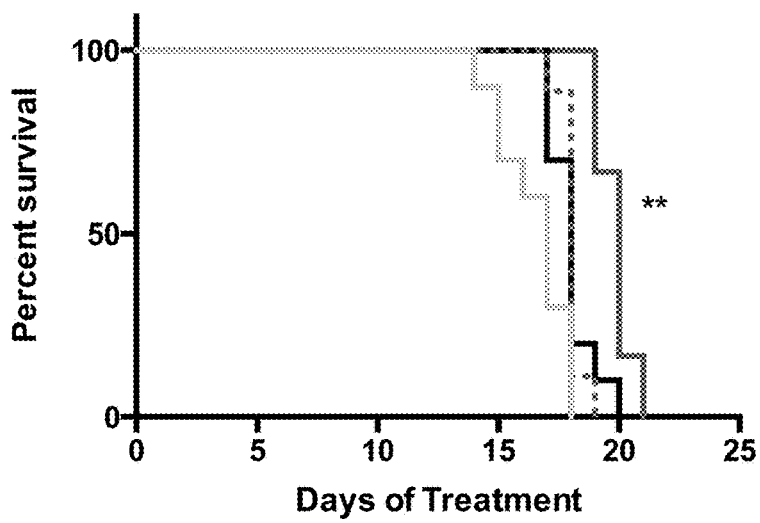

FIG. 10 shows transformed survival curves of C57Bl/6 mice carrying subcutaneous Lewis Lung tumors treated with vehicle, BGB324 Bid or PD-1/PD-L alone or in combinations as indicated. Endpoints for survival were set to the day when the tumor reached 500 mm$^3$. Significance by Mantel-Cox test.

Figure 11:
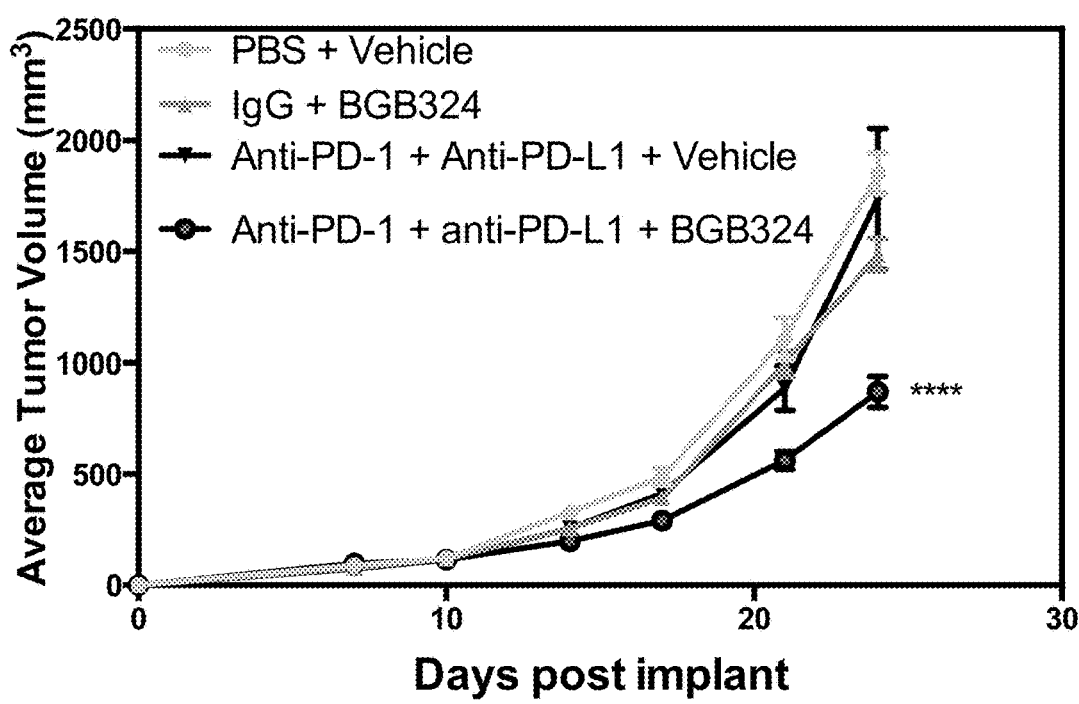

FIG. 11 shows average tumor volumes for C57Bl/6 mice carrying subcutaneous Lewis Lung tumors treated with vehicle, BGB324 or PD-1/PD-L1 alone or in combinations as indicated. Means±SEM are plotted, n=10 for all groups. Significance by Two-way ANOVA; p<0.0001.

Figure 12:
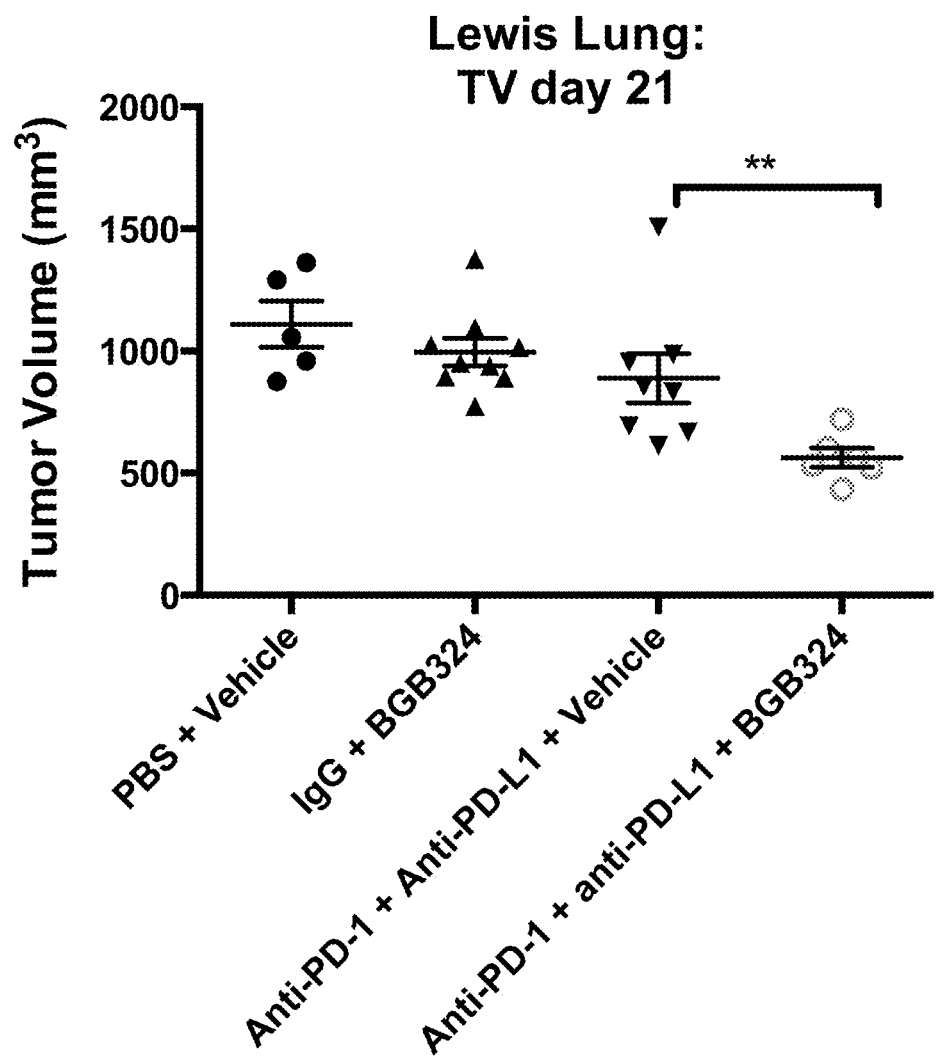

FIG. 12 shows tumor volumes at day 21 after treatment initiation for all mice presented in FIG. 11. Significance by Mann Whitney test; **p<0.01.

Figure 9:
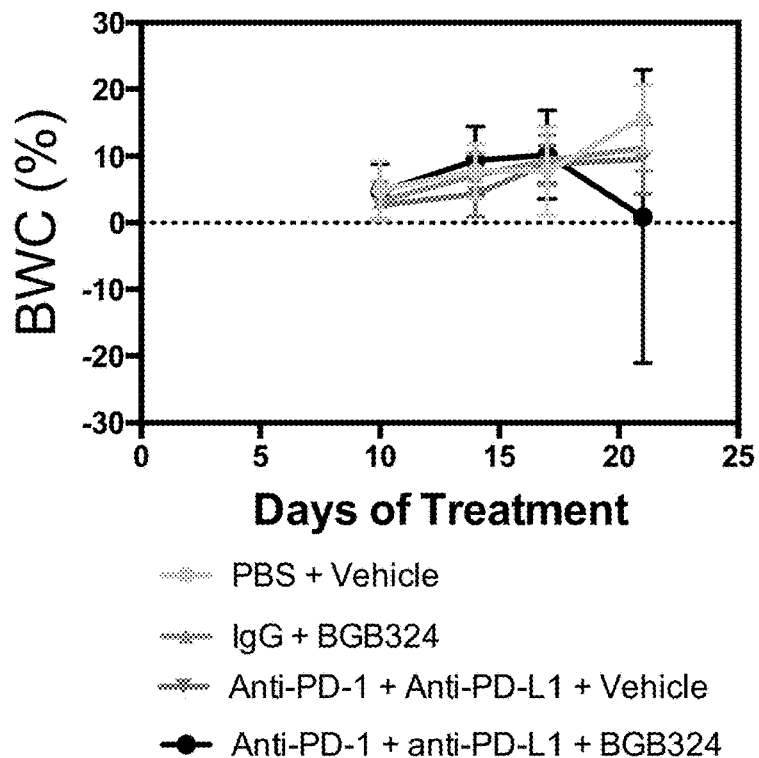
FIG. 9 shows body weight changes (BWC) C57Bl/6 mice carrying subcutaneous Lewis Lung tumors treated with vehicle, 50 mg/kg BGB324 Bid or 10 mg/kg BGB324 or 10 mg/kg PD-1/PD-L1 (each) alone or in combinations as indicated over the course of 21 days. Means±SEM are plotted, n=10 for all groups.
Figure 13:
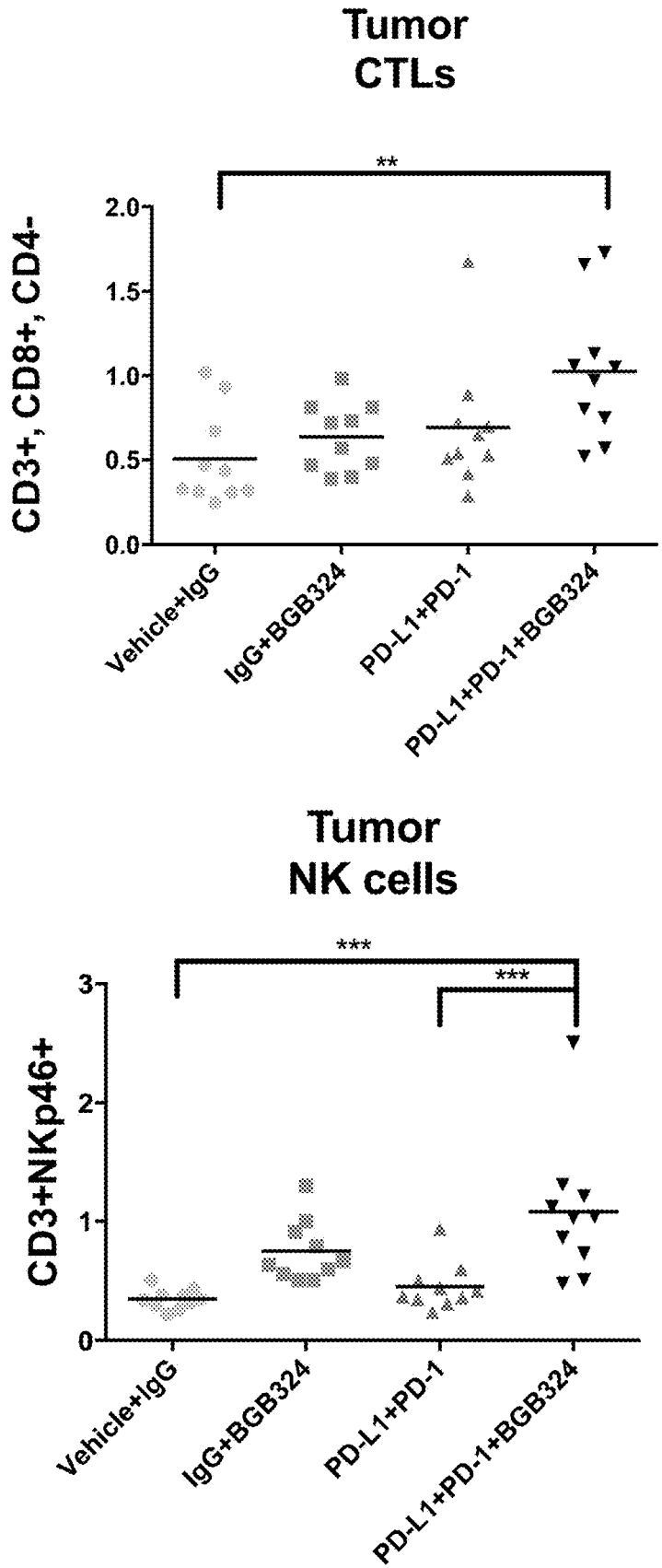

FIG. 13 shows enhanced tumor infiltration of anti-tumorigenic Cytotoxic T cells (CTLs) and Natural Killer cells (NK) in C57Bl/6 mice carrying subcutaneous Lewis Lung tumors treated with PD-1/PD-L1+BGB324 compared to PD-1/PD-L1 alone Tumors were analysed at day 21 after treatment initiation as described in legends to FIG. 9. Significance by one-way ANOVA. p<0.01; *p<0.01

Figure 14:
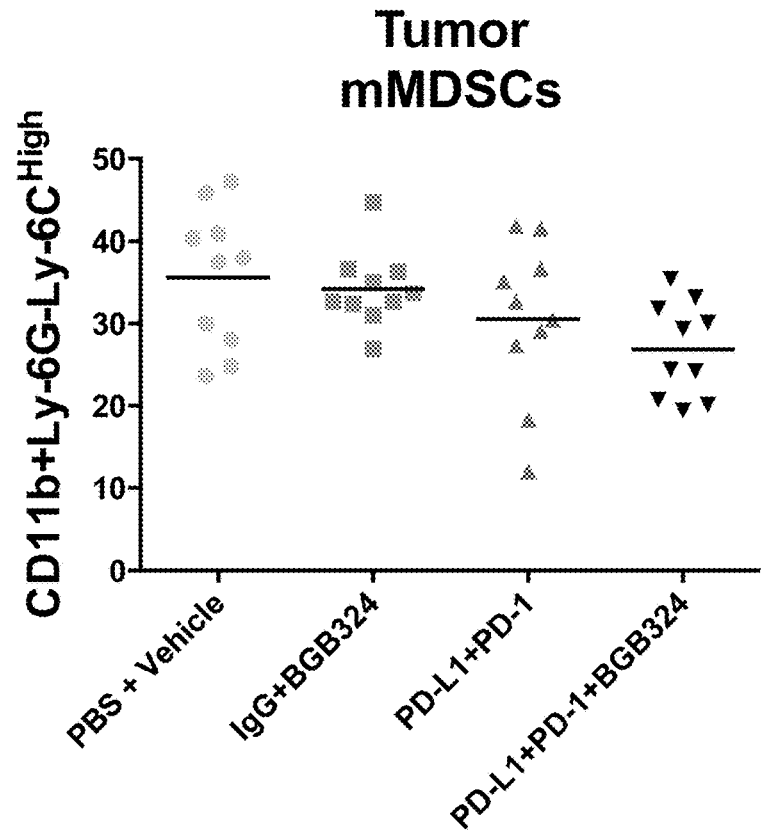

FIG. 14 shows reduced presence of pro-tumorgenic Myelo Derived Suppressor Cells (mMDSCs) in C57Bl/6 mice carrying subcutaneous Lewis Lung tumors treated with PD-1/PD-L1+BGB324 compared to PD-1/PD-L1 alone. Tumors were analysed at day 21 after treatment initiation as described in legends to FIG. 9.

Figure 15:
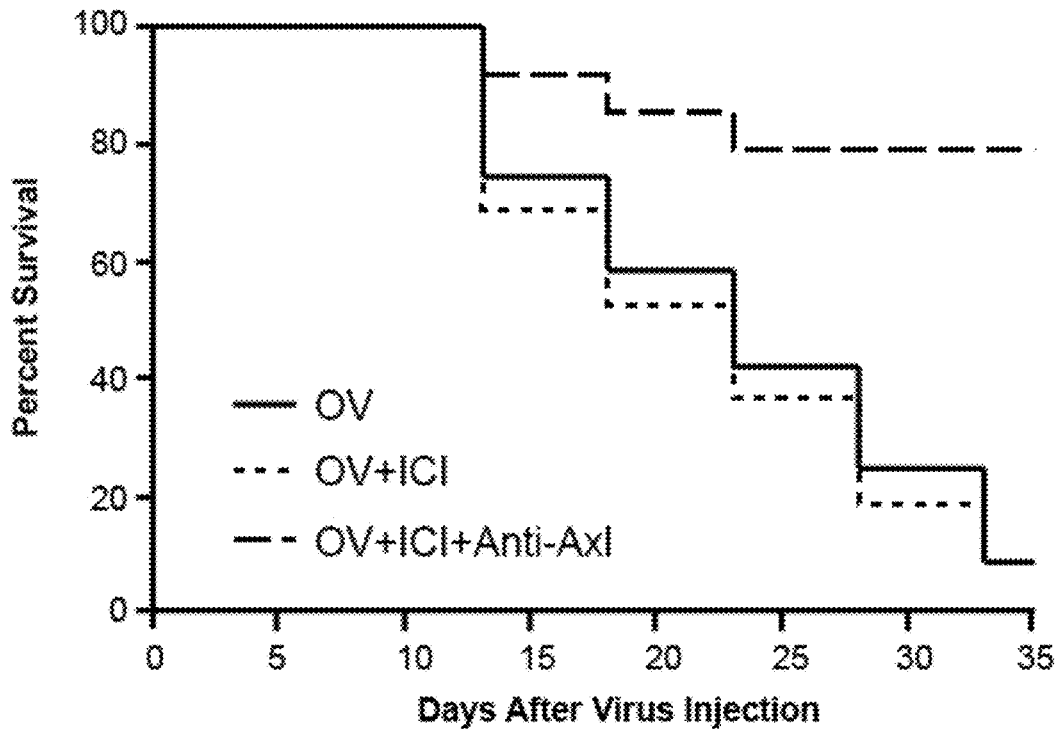

FIG. 15 shows a typical survival curve for mice treated with oncolytic virus, oncolytic virus/immune checkpoint (activity) modulator, and oncolytic virus/immune checkpoint (activity) modulator/anti-Axl.

EXAMPLES

Compounds of formula (I) utilised in the combination therapies of the invention can be made using organic synthesis techniques known to those skilled in the art, as well as by the methods described in PCT Published Patent Application No. WO 2008/083367. Specific examples of the compounds of formula (I) can be found in this publication.

Alternatively, certain compounds of formula (I), as defined above, can be made by the methods disclosed in PCT Published Patent Application No. WO 2010/083465.

Biological Examples

The following biological examples are provided by way of illustration, not limitation. In the following biological examples, 1-(6,7-dihydro-5H-benzo[6,7]cyclohepta[1,2-c]pyridazin-3-yl)-N$^3$-((7-(S)-pyrrolidin-1-yl)-6,7,8,9-tetrahydro-5H-benzo[7]annulene-2-yl)-1H-1,2,4-triazole-3,5-diamine, which is a compound of formula (I), as defined above, and which is designated in the following examples and the Figures as "BGB324", "Compound A" or "Cpd A" or "Cmpd A", was assayed for its ability to prevent, treat or manage cancer in combination with immune checkpoint (activity) modulators.

ABBREVIATIONS

TKI Tyrosine Kinase Inhibitor
CTLA-4 Cytotoxic T-Lymphocyte Antigen 4
PD-1 Programmed Death Receptor-1
Qd Once a day
PO Per Orally
FBS Fetal Bovine Serum
SOP Standard Operating Procedures
SC Subcutaneous Experimental Procedures Materials
Experimental Animals for Syngeneic 4T1 and 4T1-Luc Model:
  Species/Strain: Balb/c ABomTac
  Source: Taconic Farms
  Sex: Female
  Weight: 20-30 grams on the day of implantation
  Age: at least 6 weeks old on the day of randomization
  Animal Identification: Cage number and ear notching
Experimental Animals for Syngeneic Lewis Lung Model:
  Species/Strain: C57BL/6JOlaHsd
  Source: Harlan Laboratories
  Sex: Female
  Weight: 20-30 grams on the day of implantation
  Age: at least 6 weeks old on the day of randomization
  Animal Identification: Cage number and ear notching Cells and Materials:
- RPMI-1640 (Sigma, Cat. # R8758) supplemented with 10% fetal bovine serum (FBS), L-glutamine (4 mM), streptomycin (5 µg/ml) and penicillin (5 U/ml).
- BD Matrigel™ Basement Membrane Matrix Growth Factor Reduced, BD Bioscience, Cat. #354230, Lot #2229975.
- 0.25% Trypsin-EDTA, Sigma, Cat. # SLBD8049.

Drugs
Vehicle: 0.5% HPMC/0.1% Tween 80 vehicle for BGB324. Sterile PBS for immune checkpoint inhibitors.
IgG: InVivoMAb Polyclonal Armenian Hamster IgG, BE0091, BioXCell, Isotype control for IP injections.
BGB324: Manufacturer: Almac Group, N Ireland, batch Q1080. BGB324 powder was stored at room temperature. The BGB324 dosage given was well below the MTD in mice (023-TR-324). The BGB324 dosage administered (50 mg/kg Bid) is expected to result in a plasma concentration in mice (micro molar range) that is comparable to the one achieved in humans after administration of BGB324 (micromolar range). BGB324 was diluted in vehicle to 5 mg/ml dosing solution and administered to the mice immediately. BGB324 solution was freshly prepared every day.
Anti-mCTLA-4 (CD152) monoclonal antibody (CTAA-4): Syrian Hamster IgG, clone 9H10 (BioXCell, Cat. # BE0131).
Anti-mPD-1 monoclonal antibody (PD-1): rat IgG2a, clone RMP1-14 (BioXCell, Cat. # BE0146).
Anti-mPD-L1 monoclonal antibody (PD-L1): rat IgG2b, clone 10F.9G2 (BioXCell, Cat # BE0101).

Methods

Cell Culture

4T1 mammary adenocarcinoma cells and Non Small Cell Lung Cancer (NSCLC) Lewis Lung (LL2) were propagated at sub-confluence and split on a regular basis every $3^{rd}$ day. After trypsinization, the cells were washed once in RPMI/FBS (7 min at 1200 rpm) and re-suspended at $4\times10^6$ cells/ml (4T1 cells) or $2.5\times10^6$ per ml (LL2 cells) in a mixture of serum-free RPMI medium and Matrigel (1:1).

Subcutaneous Tumor Inoculation

Each animal was weighed before cell implantation. Injection of cells was performed after anesthetizing of mice by inhalation of sevoflurane. Anesthesia was induced with 8% sevoflurane and maintained at 4%. During injection, the mouse was placed on a heating pad. For implantation of 4T1 tumors: under a suitable depth of unconsciousness, each mouse was shaved and skin surrounding the region was washed with Chlorhexidine (1 mg/ml) with use of sterile gauze. Cells were injected into the $4^{th}$ mammary gland on the right side with 0.05 ml cell suspension comprising approximately $2\times10^5$ 4T1 cells in serum-free RPMI medium/Matrigel (1:1). The mice were kept under surveillance until regaining of consciousness. For implantation of LL2 tumors: under a suitable depth of unconsciousness, animals were shaved, and skin surrounding the region was washed with Chlorhexidine (1 mg/ml) with use of sterile gauze. Injection was subcutaneous with one tumor per mouse with 0.1 ml of approximately $2.5\times10^5$ LLC cells in serum-free RPMI medium/Matrigel (1:1).

Assignment of Experimental Groups

Before commencement of treatment, the animals were weighted and the tumor volume was measured twice a week. Since the tumor volume can affect the effectiveness of any given treatment, the mice were randomized into the groups using a Latin square method. Randomization was based on the tumor volume to ensure that each animal had the same probability of being assigned to a given treatment to reduce systematic error and that treatment groups were comparable at the baseline. When the average tumor volume reached 50-100 mm$^3$, animals were randomized into treatment groups.

Dosing Procedure

Dosing administration was 10 ml/kg PO (BGB324 and 0.5% HPMC/0.1% Tween 80) and the dosing schedule was twice a day (Bid) on a 5 days on, 2 days off schedule. Dosing administration was 10 ml/kg IP (IgG, anti-mPD-1, anti-mPD-L1 and anti-mCTLA-4) by a 30-gauge needle. For the 4T1 model, dosing schedule was 4 times with CTLA4 and PD1 on days 0, 2, 4 and 6. For the Lewis Lung model, dosing schedule was 4 times with PD1 and PD-L1 on days 4, 8, 14 and 18 on days 0, 2, 4 and 6, respectively.

Clinical Observations

Animals were weighed prior to dosing, together with tumor growth measurements, and prior to euthanasia. At the time of routine monitoring, animals were checked for any effects of tumor growth or treatments on normal behavior, such as mobility, dehydration, body weight gain/loss, eye matting and any other abnormal effect. Death and observed clinical signs were recorded. Non-fasted body weights were recorded every day.

Tumor Measurements and Endpoint

Tumor measurements: Tumor size was measure twice a week in two dimensions using a caliper, and the tumor volume was calculated using the formula: $V=0.5\ a\times b^2$ [mm$^3$], where a and b are the long and short diameter of the tumor, respectively (see Attachment 6 for raw data).

Endpoint: Mice were euthanized with $CO_2$. Tumors and spleens were snap frozen in liquid nitrogen and stored in a −80° C. freezer, and/or fixed in 4% formaldehyde, transferred to 70% ethanol after 24 h and stored at 4° C. and/or subjected to tissue dissociation for analysis of immune cell infiltration. Liver and lungs were fixed in 4% formaldehyde, transferred to 70% ethanol after 24 h and stored at 4° C. for further evaluation.

Statistical Analysis

The tumor volume of 500 mm$^3$ was used as an endpoint for the survival analysis. The Kaplan-Meier survival plots were generated using the software program PRISM (GraphPad) and the survival curves were compared using a log-rank (Mantel-Cox) test. Figures were generated using software PRISM (GraphPad). For individual time points, tumor volume values of different treatment groups were compared with other groups and significance was determined by one-way ANOVA or two-tailed unpaired t-test using software PRISM (GraphPad). Differences between the groups were considered significant when $P<0.05$. Figures were generated using software PRISM (GraphPad).

Results

AXL is Necessary for Evation of Anti-Tumorgenic Immune Response

Figure 1:
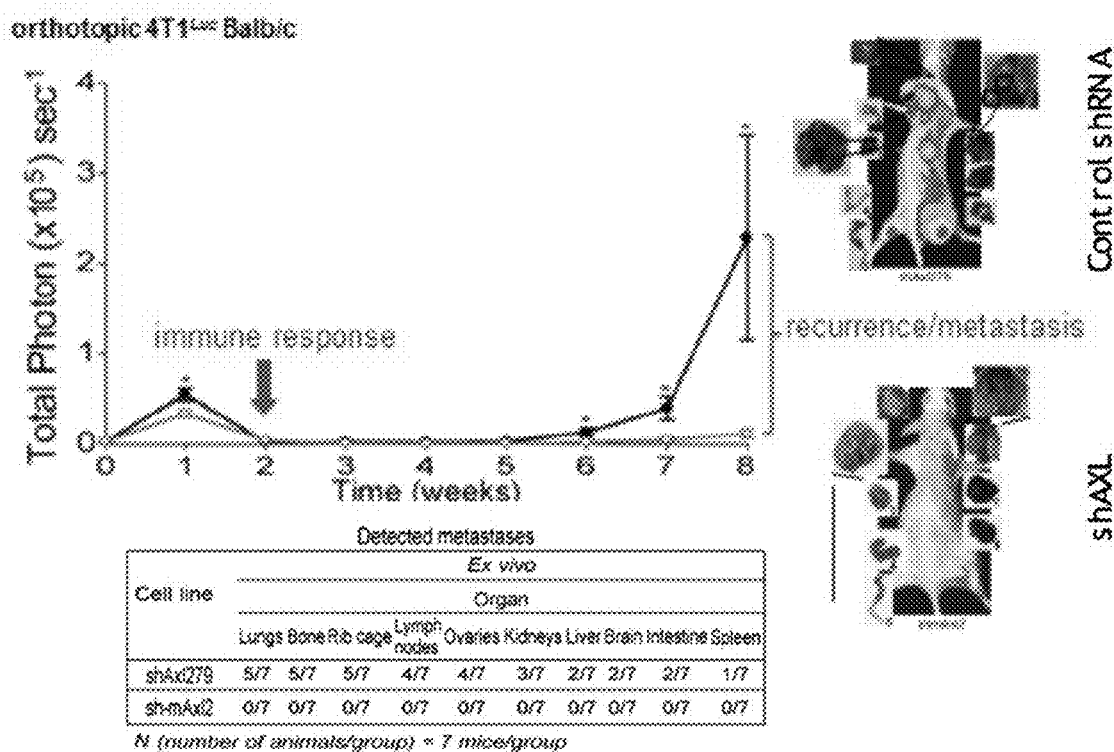

An initial robust anti-tumor immune response to the $4T1^{Luc}$ cell luciferase/GFP neo-antigens resulted in complete tumor regression (FIG. 1). After 4 weeks, tumor immune escape with robust regrowth of the primary tumor and multiorgan metastasis was detectable in all control animals. In contrast, AXL knockdown completely blocked post-immune response tumor regrowth and metastasis. This indicates that AXL is required for tumor immune escape in this model.

BGB324 Potentiates the Effect of Immune Checkpoint Inhibiting Therapy and Enhances the Presence of Pro-Tumorgenic CTLs and NK Cells in Syngeneic Mouse Models of Breast and Lung Cancer.

Body Weight Changes

Figure 2A:
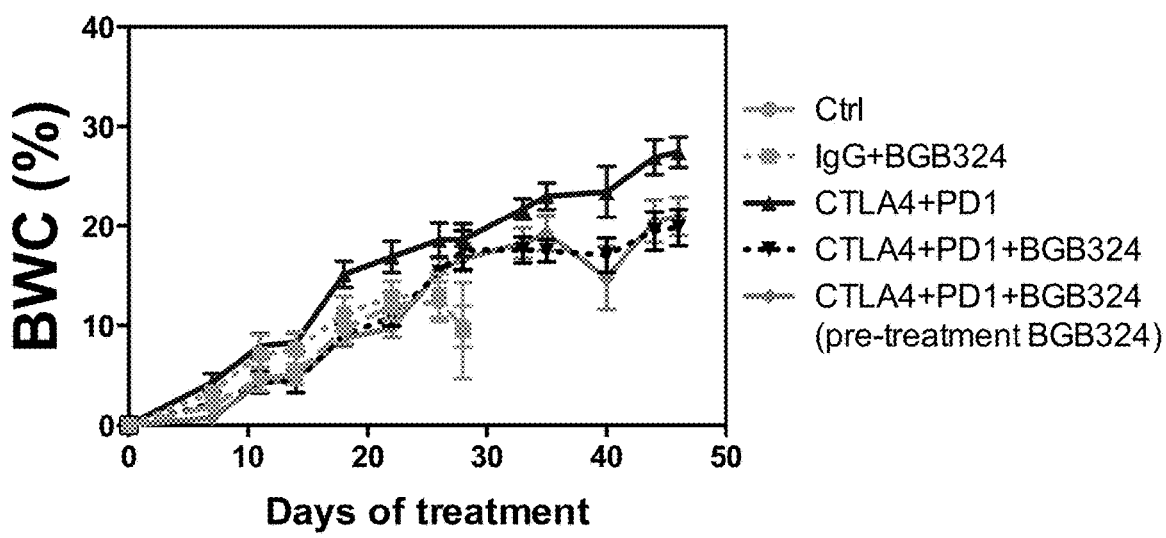
Figure 2B:
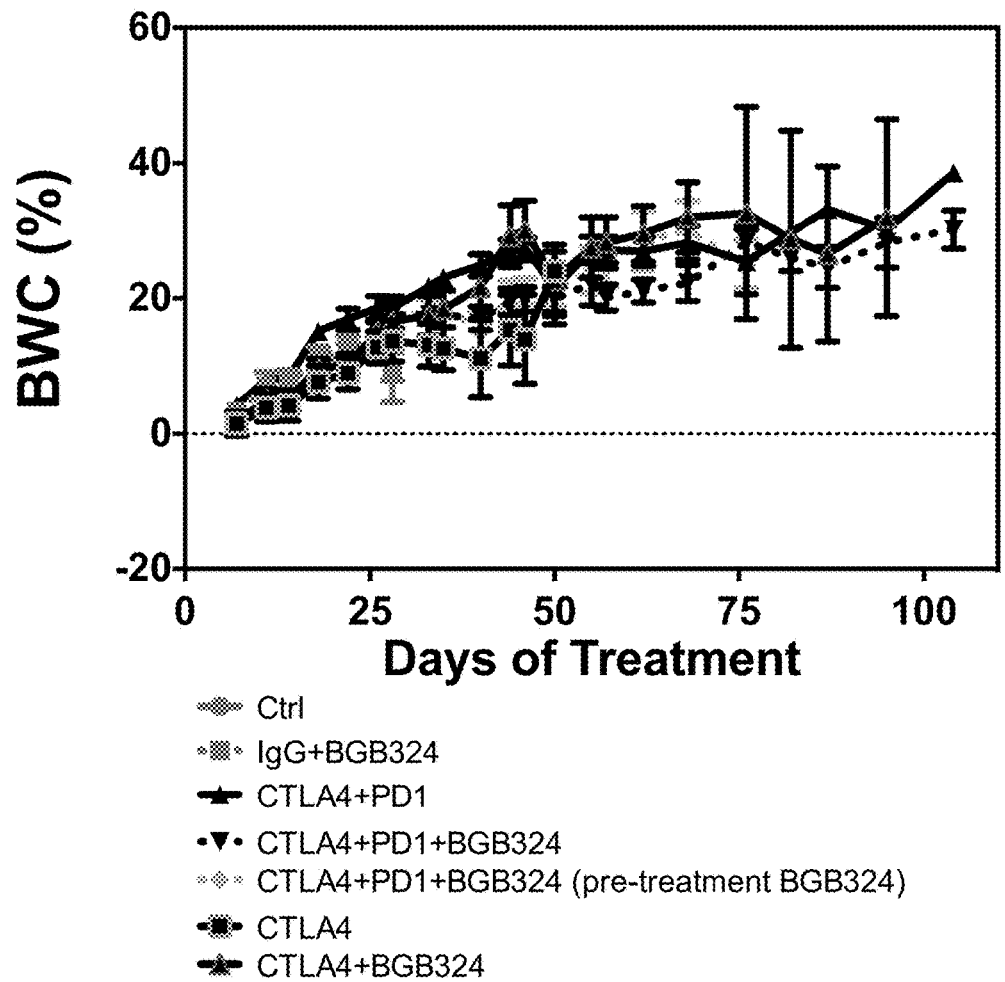

Body weight changes in 4T1 implanted Balb/c mice as a result of treatment with vehicle, BGB324 or CTLA-4/PD-1 alone or in combination over the course of 104 days were recorded; the results are shown in FIG. 2. In general, a drop in body weight >20% would indicate treatment toxicity and should lead to termination of the treatment and culling of the mouse. None of the treatment groups showed a reduction in body weight that could indicate treatment toxicity.

Body weight changes in Lewis Lung implanted C57Bl/6 mice as a result of treatment with vehicle, BGB324 or PD-1/PD-L1 alone or in combinations over the course of 21 days were recorded; the results are shown in FIG. 9. In the triple combination group treated with PD-1/PD-L1+ BGB324 a drop in body weight was observed at day 21. For 2 mice this was so severe that the study was terminated and tissue collected for analysis.

Effects of BGB324 on Survival and Tumor Volume Changes

Figure 3A:
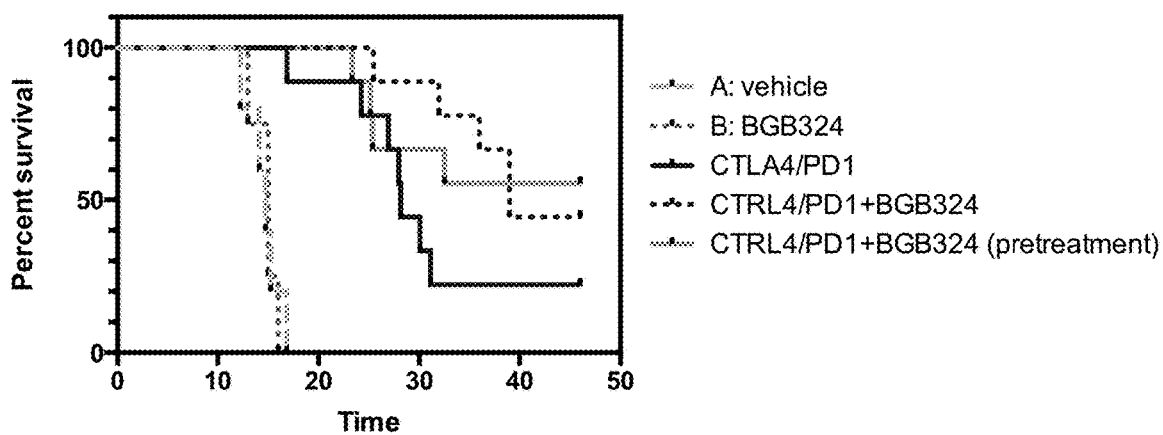
Figure 3B:
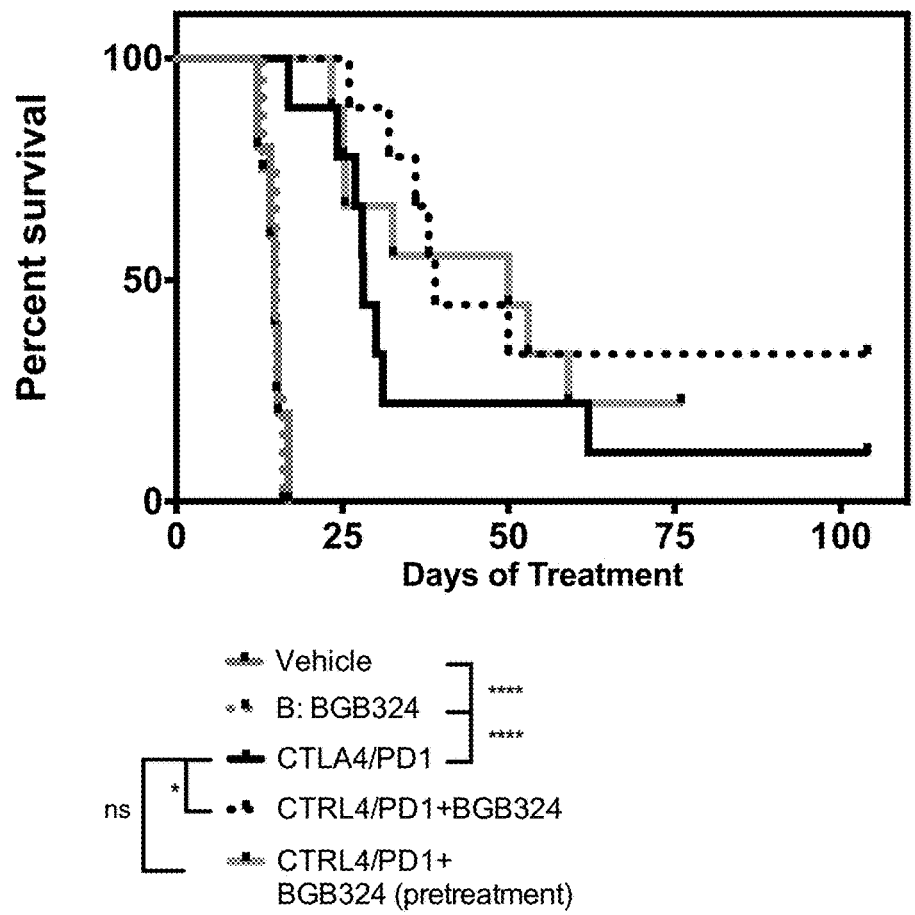
Figure 4:
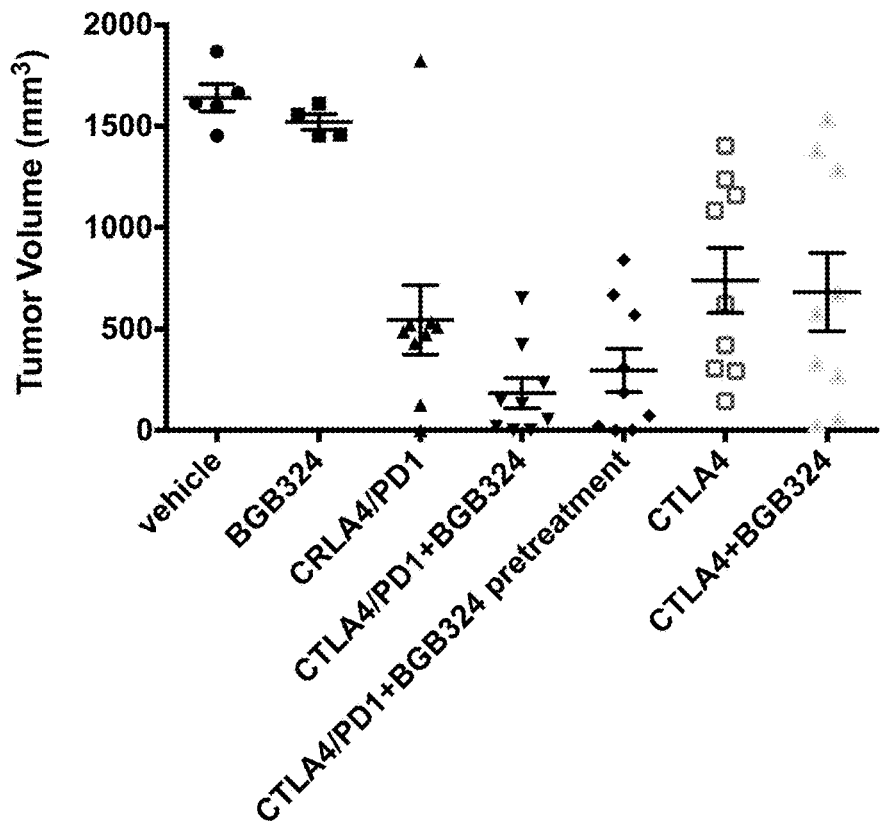
Figure 5:
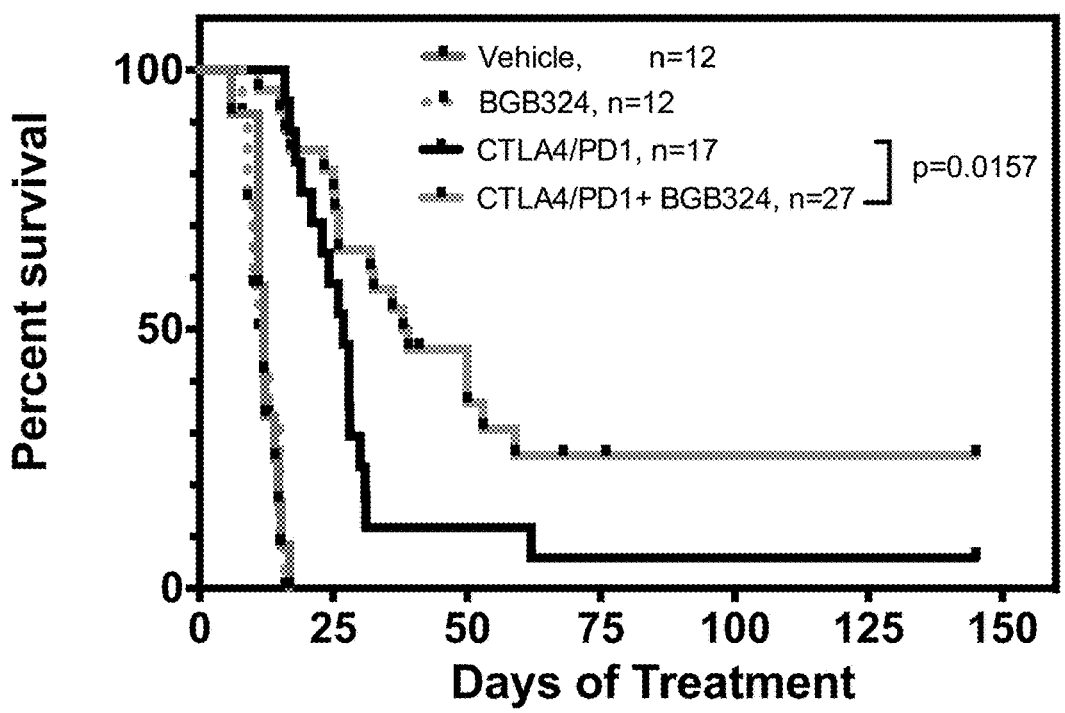

For 4T1 tumor bearing Balb/C mice, durable tumor clearance was observed in 23% of BGB324+CTLA-4/PD-L1 versus 5.6% CTLA4/PD1. Complete tumor clearance was observed in 22% of BGB324+CTLA4 treated mice versus zero for CTLA4 (FIGS. 3-5). Following treatment with BGB324+CTLA4/PD1 or BGB324+CTLA4, metastases were abrogated in responders (Tables 1 and 2).

TABLE 1

Number of metastasis detected in lung, liver and spleen in mice treated with CTLA-4 or CTLA-4 + BGB324.

| | CTLA-4 | | | CTLA-4 + BGB324 | | |
|---|---|---|---|---|---|---|
| | Lung | Liver | Spleen | Lung | Liver | Spleen |
| Non-responders | 6/8 | 5/8 | 5/8 | 6/7 P = 0.02 | 5/7 P = 0.09 | 4/7 P = 0.19 |
| Responders | na | na | na | 0/2 | 0/2 | 0/2 |

TABLE 2

Number of metastasis detected in lung, liver and spleen in mice treated with CTL-A4/PD-1 or CTLA-4/PD-1 + BGB324

| | CTLA-4/PD-1 | | | CTLA-4/PD-1 + BGB324 | | |
|---|---|---|---|---|---|---|
| | Lung | Liver | Spleen | Lung | Liver | Spleen |
| Non-responders | 11/15 | 10/15 | 12/15 | 14/16 P = 0.0009 | 9/16 P = 0.006 | 10/16 P = 0.102 |
| Responders | 0/1 | 0/1 | 0/1 | 3/8 | 0/8 | 1/8 |

Figure 3C:
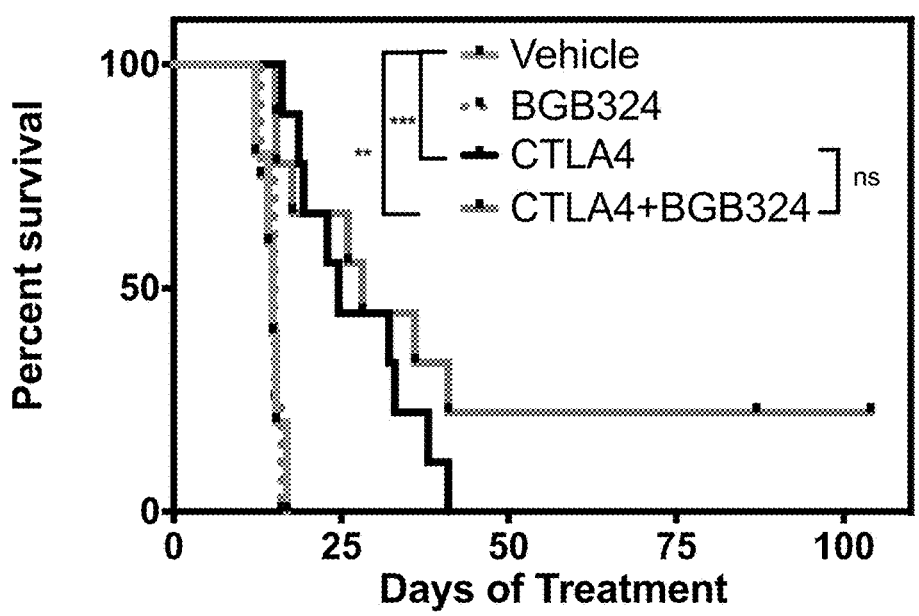

Tables 1 and 2 show metastasis detected in Balb/c mice carrying 4T1 orthotopic tumors treated with vehicle, BGB324 or CTLA-4/PD-1 alone or in combinations as indicated for the transformed survival study presented in FIG. 3c (Table 1) and FIG. 5 (Table 2). Significance by unpaired two-tailed Student t-test.

For Lewis Lung tumor bearing C57Bl/6 mice, BGB324 significantly prolonged survival and reduced tumor burden when combined with PD-1/PD-L1 compared to PD-1/PD-L1 alone (FIGS. 10-12). Metastasis was not observed for any treatment groups in this model (data not shown).

Effect of BGB324 on Immune Cell Sub-Populations

Figure 6:
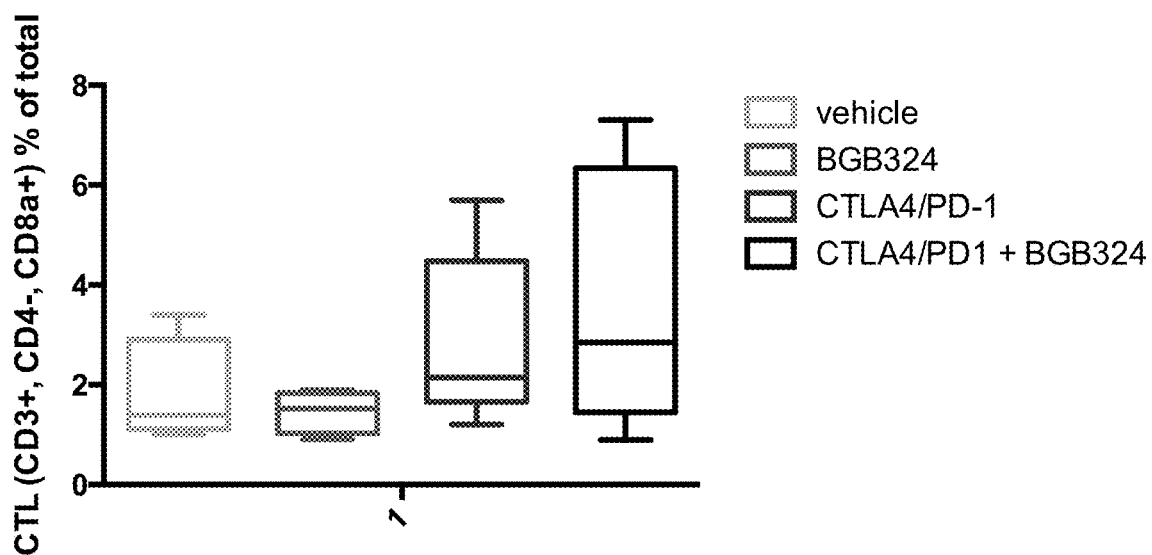
Figure 7:
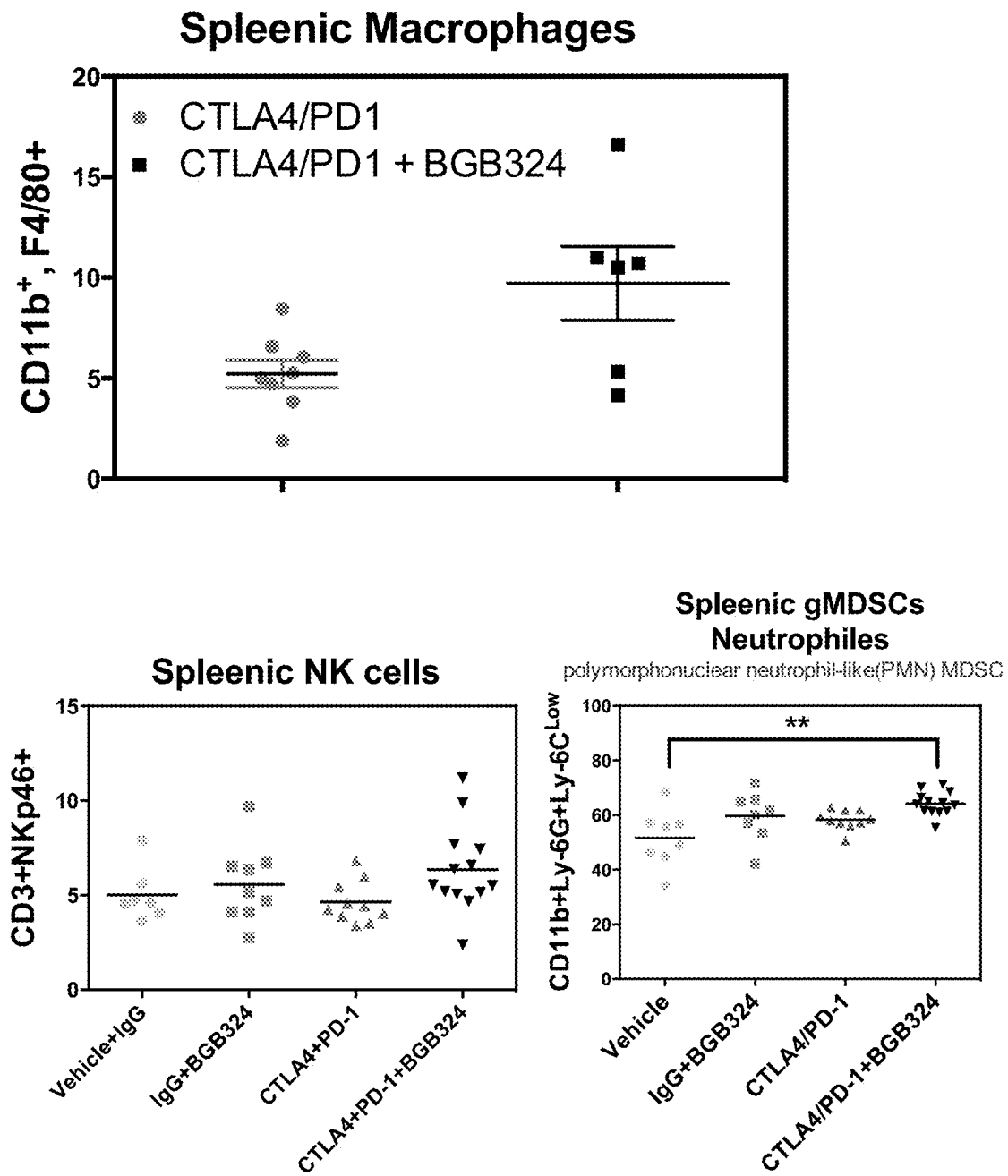
Figure 8:
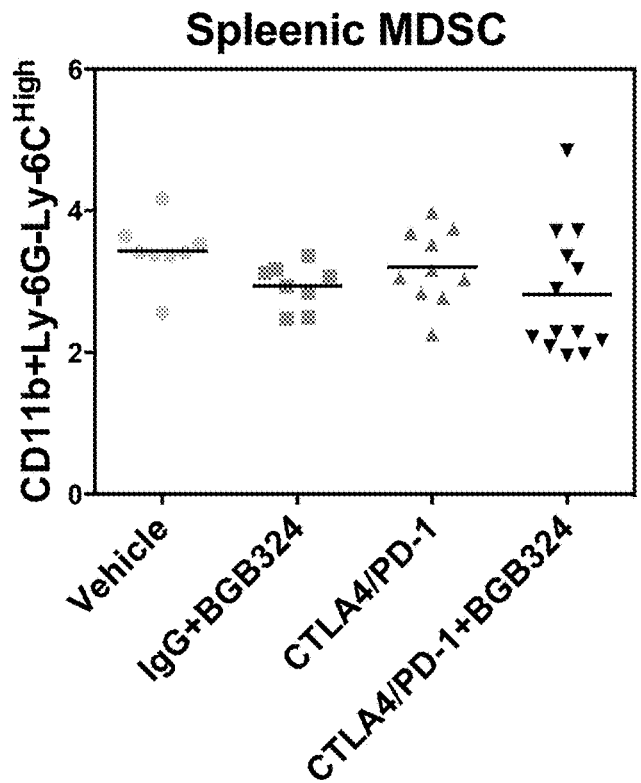
FIG. 8 shows reduced presence of pro-tumorgenic Myelo Derived Suppressor Cells (mMDSCs) in spleens of Balb/c mice carrying 4T1 orthotopic tumors treated with CTLA-4/PD-1+BGB324 compared to CTLA-4/PD-1 alone. Tumors were analysed at day 11 after treatment initiation as described in legends to FIG. 1.

BGB324 in combination with immune checkpoint inhibitors enhanced CTL tumor infiltration in both the 4T1 and Lewis Lung model (FIGS. 6 and 13 respectively). In the Lewis lung model, also enhanced presence of NK cells (FIG. 13) was observed. For the 4T1 model, enhanced presence of NK cells, macrophages and PMN neuotrophiles were found in the spleen (FIG. 7). In addition, a reduction in the presence of pro-tumorigenic mMDSC were observed in both models (FIGS. 8 and 14). These findings support that BGB324 can mediate its anti-tumorgenic effect (FIGS. 3, 4, 5 and Tables 1 and 2; FIGS. 10-12) by enhancing the presence of tumor killing immune cells such as CTLs and NK cells and by reducing the presence of pro-tumorigenic neutrophils such as mMDSC.

CONCLUSION

Targeting AXL signaling represents a unique opportunity to address multiple tumor immune suppression mechanisms. Our results in breast and lung cancer mouse models support combining the clinical-stage AXL inhibitor, BGB324, with cancer immune checkpoint inhibitors to improve treatment of human cancers.

REFERENCES

Chen L, 2014. Rejection of metastatic 4T1 breast cancer by attenuation of Treg cells in combination with immune stimulation. Mol Ther. 2007 December; 15(12):2194-202. Epub 2007 Oct. 30. PubMed PMID: 17968355.

Chen L, et al. 2014. Metastasis is regulated via microRNA-200/ZEB1 axis control of tumour cell PD-L1 expression and intratumoral immunosuppression. Nat Commun. 2014 Oct. 28; 5:5241. doi: 10.1038/ncomms6241.

Gjerdrum C, et al. 2010. Axl is an essential epithelial-to-mesenchymal transition-induced regulator of breast cancer metastasis and patient survival. Proc Natl Acad Sci USA. 2010 Jan. 19;107(3):1124-9. doi: 10.1073/pnas.0909333107. Epub 2009 Dec. 28.

Grosso J F, et al. 2013. CTLA-4 blockade in tumor models: an overview of preclinical and translational research. Cancer Immun. 2013; 13:5. Epub 2013 Jan. 22. Review. PubMed PMID: 23390376.

Kyi C, et al. 2014. Checkpoint blocking antibodies in cancer immunotherapy. FEBS Lett. 2014 Jan. 21; 588(2):368-76. doi: 10.1016/j.febslet.2013.10.015. Epub 2013 Oct. 23. Review.

Lou Y, et al 2014. Association of epithelial-mesenchymal transition status with PD1/PDL1 expression and a distinct immunophenotype in non-small cell lung cancer: Implications for immunotherapy biomarkers. J Clin Oncol 32:5s, 2014 (suppl; abstr 3018).

Lu J, et al. 2014. Clinical evaluation of compounds targeting PD-1/PD-L1 pathway for cancer immunotherapy. J Oncol Pharm Pract. Epub ahead of print] PubMed PMID: 24917416.

Paolino M, et al. 2014. The E3 ligase Cbl-b and TAM receptors regulate cancer metastasis via natural killer cells. Nature. 2014 Mar. 27; 507(7493):508-12. doi: 10.1038/nature12998.

Rothlin C V, et al. 2007. TAM receptors are pleiotropic inhibitors of the innate immune response. Cell. 2007 Dec. 14; 131(6):1124-36.

Effect of Axl Inhibitor on Immune Checkpoint Inhibitor Efficacy

Background

Signaling via the Axl receptor tyrosine kinase is a key suppressor of anti-tumour innate immune response. Axl is expressed on several cells associated with the suppressive tumpour immune microenvironment including natural killer cells, dendritic cells and tumour-associated macrophages.

Axl is also an important regulator of tumour plasticity related to epithelial-to-mesenchymal transition (EMT) that contributes to anti-tumour evasion. Hence Axl signaling contributes uniquely to tumour intrinsic and microenvironmental immune suppression in tumours. It was therefore evaluated whether blocking Axl signaling with BGB324, a selective clinical-stage small molecule checkpoint blockade in sygeneic cancer mouse models that display limited immunogenicity.

Axl, EMT and Immune Suppression

Axl is a down-regulator of the innate immune response upon activation of the adaptive immune system. Axl mediates M1 to Mr polarisation (Chiu, K. C., et al. (2015). Oral Oncol). High Axl expression on tumour associated macrophages in human primary breast cancer (Ye, X., et al. (2010). Oncogene). TAM inhibition in NK cells reduces metastasis from melanoma and mammary carcinoma (Paolino, M., et al. (2014). Nature). The Axl ligand Gas6 is upregulated by tumour infiltrating macrophages and contributes to tumour growth and metastasis (Loges, S., et al. (2010). Blood). High EMT score correlates with immunosuppressive phenotype (Lou, Y., et al. (2014). J Clin Oncol suppl; abstr 3018). PD-L1 expression correlates with mesenchymal phenptype (Chen, L., et al. (2014). Nat Commun). The EMT transcription factor Snail induces immunosuppression leading to increased metastasis and confers resistance yo cytotoxic T cell attack (Kudo-Saito, C., et al. (2009). Cancer Cell). EMT increases autophagy flux, and autophagy inhibition sensitises EMTed cells to cytotoxic T cell lysis (Akalay, I., et al. (2013) Cancer Res).

Axl Inhibition in Post-Immune Response Tumour Recurrence and Metastasis in the Mammary Adenocarcinoma 4T1/Balb/C Syngeneic Mouse Model BalbC mice were orthotopically implanted with 1×106 4T1-GFPLuc cells infected with the mouse Axl-targeting shRNA (4T1-GFPLuc-shmAxl2; shAXL) or negative control human-specific shRNA (4T1-GFP-Luc-shAxl279; control shRNA) cells. Tumour growth and metastasis spread was monitored every week by bioluminescent imaging. After 9 weeks, organs were excised and imaged ex vivo for occurrence of metastasis. The results are shown in FIG. 1. An initial robust immune response induced tumours regression followed by tumour immune evasion with regrowth of the primary tumour and widespread metastasis in mice implanted with 4T1-GFP-Luc control shRNA cells. Axl knock down suppressed regrowth at the primary site and abolished metastasis (Gjerdrum, C., et al. (2010). Proc Natl Acad Sci USA). This indicates that Axl contributes to immune evasion.

Axl Inhibition Potentiates the Effect of Immune Checkpoint Inhibitors in the Mammary Adenocarcinoma 4T1/Balb/C Syngeneic Mouse Model BalbC mice were orthotopically implanted with 4×105 4T1 cells. Treatment was initiated when average tumour volume reached 100 mm$^3$. Animals were treated with anti-CTLA4 and anti-PD1 as indicated at 10 mg/kg of each (4 doses every 2nd day, IP). BGB324 was administered at 50 mg/kg twice a day (oral gavage). Vehicle groups were injected with control IgG. Transformed survival curves are shown. The day each individual tumour reached 500 mm$^3$ was used as an endpoint. Complete tumour clearance was observed in 23% of the anti-CTLA4/anti-PD1+BGB324 treated mice versus 5.6% for the anti-CTLA4/anti-PD1 treated mice. Complete tumour clearance was observed in 22% of the anti-CTLA4+BGB324 treated mice versus zero for the anti-CTLA4 treated mice. BalbC mice that displayed complete clearance of the tumour were re-injected orthotopically with 4T1 cells at day 105 after the first cell injection. Subsequent tumour growth was not observed in any of these mice (from anti-CTLA4/PD-1 group, n=1; from anti-CTLA4/PD-1+BGB324, n=4) indicating that these mice were immune towards subsequent 4T1 cell exposure. The results are shown in FIG. 5.

Axl Inhibition Treatment Enhances the Number of CTLs in Tumours and Spleens

For CTL (cytotoxic T-lymphocyte) analysis in tumors: BalbC mice were orthotopically implanted with 4×105 4T1 cells. Treatment (anti-CTLA4+anti-PD1 at 10 mg/kg of each, 3 doses every 2nd day, IP; BGB324 at 50 mg/kg twice a day, oral gavage; Vehicle control IgG at 20 mg/kg, 3 doses every 2nd day, IP) was initiated when average tumour volume reached 500 mm$^3$. Tumours were harvested 5 days after treatment initiation (n=5 for all groups), dissociated using MACS Tumor Dissociation Kit, stained for markers of CTLs and analysed on a BD Fortessa Cell Analyser. Anti-CTLA4/PD1 treatment enhanced infiltration of CTLs in 4T1 tumors when compared to Vehicle or BGB324 treated mice. Treatment with BGB324 further enhanced tumour infiltration of CTLs. The results are shown in FIG. 6.

For CTL analysis in spleen: BalbC mice were orthotopically implanted with 4×105 4T1 cells. Treatment (anti-CTLA4+anti-PD at 10 mg/kg of each, 4 doses every 2nd day, IP; BGB324 as above) was initiated when average tumor volume reached 100 mm$^3$. Mice were culled 43 days after treatment initiation. Spleens were dissociated using MACS Tumor Dissociation Kit and stained for markers of CTLs. Responders (top two points in CTLA4; top two points in CTLA4/PD1; top three points in CTLA4/PD1/BGB324) in all groups had a higher number of CTLs in the spleen compared to nonresponders (remaining points). BGB324 further enhanced the number of CTLs compared to treatment with immune check point inhibitors alone.

Tumours Escaping Checkpoint Blockade Show an Increased Mesenchymal Phenotype

BalbC were orthotopically implanted with 4×105 4T1 cells, and treatment was initiated when average tumour volume reached 100 mm$^3$. Animals were treated with anti-CTLA4+anti-PD1 as indicated at 10 mg/kg of each (4 doses every 2nd day, IP). BGB324 was administered at 50 mg/kg twice a day (oral gavage). Control groups were injected with control IgG. Tumours were harvested from non-responders (i.e. tumours that had escaped treatment inhibition and reached 1500 mm$^3$) and responders (i.e. tumours that responded to treatment and remained below 500 mm$^3$ until termination of experiment) and processed by IHC for evaluation of known EMT markers.

Tumours treated with checkpoint inhibitors alone or in combination with BGB324 that did not respond to the treatment, displayed stronger staining for Axl and Vimentin compared tumours from the control groups (vehicle, BGB324 alone). However, in a responding tumour treated with BGB324+anti-CTLA4/anti-PD-1 weaker Axl- and Vimentin staining were observed.

This suggests that EMT is involved in the immune evasion of tumors escaping checkpoint inhibition, and that targeting Axl may inhibit EMT mediated immune evasion.

CONCLUSION

This data therefore shows that Axl inhibition (particularly by BGB324) represents an unique opportunity to target anti-tumour immune suppressive mechanisms and supports clinical translation of Axl inhibition in combination with cancer immunotherapy in human cancers.

Effect of Anti-Axl, Oncolytic Virus and Immune Checkpoint Inhibitor Combination Therapy on Metastasis Tumours are implanted into female Balb/c mice and mice are injected when tumours reach ~50-100 mm³. Tumour volume is monitored by caliper measurement and defined by V(mm³)=π/6×W2×L, where W and L are the width and the length of the tumour, respectively. Mice are injected with 2×10⁸ plaque forming units (pfu) of Oncolytic Virus (OV) through the tail vein starting at day 0. For the anti-Immune Checkpoint Inhibitor (ICI) group, 100 µg of anti-ICI antibody is injected intraperitoneally (IP) at day 4 after virus injection, with treatments consisting of 3 doses each 3 days apart. For the combination group, anti-Axl is administered along with the OV at day 0, then 100 µg of anti-ICI antibody is administered at day 4. Anti-Axl treatment is either monoclonal anti-Axl antibody or a small molecule Axl inhibitor. The anti-Axl antibody is administered IP at doses of 30 mg/kg body weight, twice weekly. The small molecule inhibitor is administered at 50 mg/kg in 0.5% (w/w) HPMC/0.1% (w/w) Tween 80 twice daily by oral gavage. For the Kaplan-Meier survival curve, end point is established at a tumour volume ≥750 mm³. A typical result is shown in FIG. 15.

The invention claimed is:

1. A method of controlling cancer in a patient comprising administering to the patient in need thereof a therapeutically effective amount of an Axl inhibitor in concurrent, separate or sequential combination with a therapeutically effective amount of at least two immune checkpoint inhibitors wherein the Axl inhibitor is a compound of formula (I):

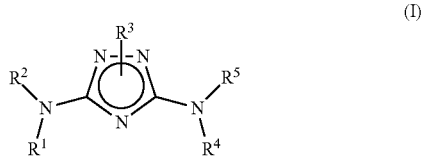

wherein:

$R^1$, $R^4$ and $R^5$ are each independently selected from the group consisting of hydrogen, alkyl, alkenyl, aryl, aralkyl, —C(O)R⁸, —C(O)N(R⁶)R⁷, and —C(=NR⁶)N(R⁶)R⁷;

$R^2$ and $R^3$ are each independently a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R⁹—OR⁸, —R⁹—O—R¹⁰—OR⁸, —R⁹—O—R¹⁰—O—R¹⁰—OR⁸, —R⁹—O—R¹⁰—CN, —R⁹—O—R¹⁰—C(O)OR⁸, —R⁹—O—R¹⁰—C(O)N(R⁶)R⁷, —R⁹—O—R¹⁰—S(O)ₚR⁸ (where p is 0, 1 or 2), —R⁹—O—R¹⁰—N(R⁶)R⁷, —R⁹—O—R¹⁰—C(NR¹¹)N(R¹¹)H, —R⁹—OC(O)—R⁸, —R⁹—N(R⁶)R⁷, —R⁹—C(O)R⁸, —R⁹—C(O)OR⁸, —R⁹—C(O)N(R⁶)R⁷, —R⁹—N(R⁶)C(O)OR⁸, —R⁹—N(R⁶)C(O)R⁸, —R⁹—N(R⁶) S(O)ₜR⁸ (where t is 1 or 2), —R⁹—S(O)ₜOR⁸ (where t is 1 or 2), —R⁹—S(O)ₚR⁸ (where p is 0, 1 or 2), and —R⁹—S(O)ₜN(R⁶)R⁷ (where t is 1 or 2);

or $R^2$ is a polycyclic heteroaryl containing more than 14 ring atoms as described above and $R^3$ is selected from the group consisting of aryl and heteroaryl, where the aryl and the heteroaryl are each independently optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R¹³—OR¹², —R¹³—OC(O)—R¹², —R¹³—O—R¹⁴—N(R¹²)₂, —R¹³—N(R¹²)—R¹⁴—N(R¹²)₂, —R¹³—N(R¹²)—R¹⁴—N(R¹²)₂, —R¹³—N(R¹²)₂, —R¹³—C(O)OR¹², —R¹³—C(O)N(R¹²)₂, —R¹³—C(O)N(R¹²)—R¹⁴—N(R¹²)R¹³, —R¹³—C(O)N(R¹²)—R¹⁴—OR¹², —R¹³—N(R¹²)C(O)OR¹², —R¹³—N(R¹²)C(O)R¹², —R¹³—N(R¹²)S(O)ₜR¹² (where t is 1 or 2), —R¹³—S(O)ₜOR¹² (where t is 1 or 2), —R¹³—S(O)ₚR¹² (where p is 0, 1 or 2), and —R¹³—S(O)ₜN(R¹²)₂ (where t is 1 or 2);

or $R^3$ is a polycyclic heteroaryl containing more than 14 ring atoms as described above, and $R^2$ is selected from the group consisting of aryl and heteroaryl, where the aryl and the heteroaryl are each independently optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R¹³—OR¹², —R¹³—OC(O)—R¹², —R¹³—O—R¹⁴—N(R¹²)₂, —R¹³—N(R¹²)—R¹⁴—N(R¹²)₂, —R¹³—N(R¹²)—R¹⁴—N(R¹²)₂, —R¹³—N(R¹²)₂, —R¹³—C(O)OR¹², —R¹³—C(O)N(R¹²)₂, —R¹³—C(O)N(R¹²)—R¹⁴—N(R¹²)R¹³, —R¹³—C(O)N(R¹²)—R¹⁴—OR¹², —R¹³—N(R¹²)C(O)OR¹², —R¹³—N(R¹²)C(O)R¹², —R¹³—N(R¹²)S(O)ₜR¹² (where t is 1 or 2), —R¹³—S(O)ₜOR¹² (where t is 1 or 2), —R¹³—S(O)ₚR¹² (where p is 0, 1 or 2), and —R¹³—S(O)ₜN(R¹²)₂ (where t is 1 or 2);

each $R^6$ and $R^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, $-R^{10}-OR^8$, $-R^{10}-CN$, $-R^{10}-NO_2$, $-R^{10}-N(R^8)_2$, $-R^{10}-C(O)OR^8$ and $-R^{10}-C(O)N(R^8)_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

each $R^9$ is independently selected from the group consisting of a direct bond, an optionally substituted straight or branched alkylene chain, an optionally substituted straight or branched alkenylene chain and an optionally substituted straight or branched alkynylene chain;

each $R^{10}$ is independently selected from the group consisting of an optionally substituted straight or branched alkylene chain, an optionally substituted straight or branched alkenylene chain and an optionally substituted straight or branched alkynylene chain;

each $R^{11}$ is independently selected from the group consisting of hydrogen, alkyl, cyano, nitro and $-OR^8$;

each $R^{12}$ is independently selected from the group consisting of hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl, optionally substituted heteroarylalkyl, $-R^{10}-OR^8$, $-R^{10}-CN$, $-R^{10}-NO_2$, $-R^{10}-N(R^8)_2$, $-R^{10}-C(O)OR^8$ and $-R^{10}-C(O)N(R^8)_2$, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond, an optionally substituted straight or branched alkylene chain and an optionally substituted straight or branched alkenylene chain; and each $R^{14}$ is independently selected from the group consisting of an optionally substituted straight or branched alkylene chain and an optionally substituted straight or branched alkenylene chain;

as an isolated stereoisomer or mixture thereof or as a tautomer or mixture thereof, or a pharmaceutically acceptable salt or N-oxide thereof, and wherein one of the at least two immune checkpoint inhibitors is an anti-CTLA-4 antibody or an anti-PD-1 antibody; and wherein the cancer is an Axl-expressing cancer.

2. The method according to claim 1, wherein the compound of formula (I) is selected from the group consisting of:

1-(6,7-dihydro-5H-benzo[6,7]cyclohepta[1,2-c]pyridazin-3-yl)-$N^3$-(7-(pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-((7-(S)-pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-((7-(R)-pyrrolidin-1-yl)-6,7,8,9-tetrahydro-5H-benzo[7]annulene-2-yl)-1H-1,2,4-triazole-3,5-diamine;

1-(6,7-dihydro-5H-pyrido[2',3':6,7]cyclohepta[1,2-c]pyridazin-3-yl)-$N^3$-(3-fluoro-4-(4-(pyrrolidin-1-yl)piperidin-1-yl)phenyl)-1H-1,2,4-triazole-3,5-diamine;

1-(6,7-dihydro-5H-benzo[6,7]cyclohepta[1,2-c]pyridazin-3-yl)-$N^5$-(7-(pyrrolidin-1-yl)-6,7,8,9-tetrahydro-5H-benzo[7]annulene-1-yl)-1H-1,2,4-triazole-3,5-diamine;

1-(6,7-dihydro-5H-benzo[6,7]cyclohepta[1,2-c]pyridazin-3-yl)-$N^5$-(7-(S)-pyrrolidin-1-yl-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-((7S)-7-(t-butoxycarbonylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-(acetamido)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-((2R)-2-(methoxycarbonyl)pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-(4,4-difluoropiperidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-((methoxycarbonylmethyl)(methyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-((2R)-2-(carboxy)pyrrolidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-(4-(ethoxycarbonyl)piperidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-(4-(carboxy)piperidin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-((carboxymethyl)(methyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-(4-(ethoxycarbonylmethyl)piperazin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-(4-(carboxymethyl)piperazin-1-yl)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-$N^3$-(7-(pyrrolidin-1-yl)-6,7,8,9-tetrahydro-5H-benzo[7]annulene-1-yl)-1H-1,2,4-triazole-3,5-diamine;

1-(6,7-dihydro-5H-benzo[6,7]cyclohepta[1,2-c]pyridazin-3-yl)-N$^3$-((7S)-7-amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7s)-7-(di(cyclopropylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-((2-methylpropyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-((propyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(dipropylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(diethylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(cyclohexylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(cyclopentylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(1-cyclopentylethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(2-propylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(3,3-dimethylbut-2-yl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-((cyclohexylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(di(cyclohexylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(5-chlorothien-2-yl)methyl)amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(2-carboxyphenyl)methyl)amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(3-bromophenyl)methyl)amino-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(dimethylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(cyclobutylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(3-pentylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(2,2-dimethylpropyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(di(cyclopentylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-((cyclopentylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(di(bicyclo[2.2.1]hept-2-en-5-ylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-((bicyclo[2.2.1]hept-2-en-5-ylmethyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(3-methylbutylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(di(3-methylbutyl)amino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(2-ethylbutylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(but-2-enylamino)-6,7,8,9-tetrahydro-5H-benzo[7]annulene-2-yl)-1H-1,2,4-triazole-3,5-diamine;

1-(6,7-dihydro-5H-benzo[6,7]cyclohepta[1,2-c]pyridazin-3-yl)-N$^3$-((7S)-7-(butyl(but-2-enyl)amino)-6,7,8,9-tetrahydro-5H-benzo[7]annulene-2-yl)-1H-1,2,4-triazole-3,5-diamine;

1-(6,7-dihydro-5H-pyrido[2',3':6,7]cyclohepta[1,2-c]pyridazin-3-yl)-N$^5$-((7S)-7-(t-butoxycarbonylamino)-6,7,8,9-tetrahydro-5H-benzo[7]annulene-2-yl)-1H-1,2,4-triazole-3,5-diamine;

1-(6,7-dihydro-5H-pyrido[2',3':6,7]cyclohepta[1,2-c]pyridazin-3-yl)-N$^3$-((7S)-7-amino-6,7,8,9-tetrahydro-5H-benzo[7]annulene-2-yl)-1H-1,2,4-triazole-3,5-diamine;

1-(6,7-dihydro-5H-pyrido[2',3':6,7]cyclohepta[1,2-c]pyridazin-3-yl)-N$^3$-((7 S)-7-(dimethylamino)-6,7,8,9-tetrahydro-5H-benzo[7]annulene-2-yl)-1H-1,2,4-triazole-3,5-diamine;

1-(6,7-dihydro-5H-pyrido[2',3':6,7]cyclohepta[1,2-c]
pyridazin-3-yl)-N³-((7S)-7-(diethylamino)-6,7,8,9-tet-
rahydro-5H-benzo[7]annulen-2-yl)-1H-1,2,4-triazole-
3,5-diamine;
1-(6,7-dihydro-5H-pyrido[2',3':6,7]cyclohepta[1,2-c]
pyridazin-3-yl)-N³-((7S)-7-(dipropylamino)-6,7,8,9-
tetrahydro-5H-benzo[7]annulen-2-yl)-1H-1,2,4-triaz-
ole-3,5-diamine;
1-(6,7-dihydro-5H-pyrido[2',3':6,7]cyclohepta[1,2-c]
pyridazin-3-yl)-N³-((7S)-7-(di(cyclopropylmethyl)
amino)-6,7,8,9-tetrahydro-5H-benzo[7]annulen-2-
yl)-1H-1,2,4-triazole-3,5-diamine;
1-(6,7-dihydro-5H-pyrido[2',3':6,7]cyclohepta[1,2-c]
pyridazin-3-yl)-N³-((7S)-7-(di(3-methylbutyl)amino)-
6,7,8,9-tetrahydro-5H-benzo[7]annulen-2-yl)-1H-1,2,
4-triazole-3,5-diamine;
1-(6,7-dihydro-5H-pyrido[2',3':6,7]cyclohepta[1,2-c]
pyridazin-3-yl)-N³-((7S)-7-(cyclobutylamino)-6,7,8,9-
tetrahydro-5H-benzo[7]annulen-2-yl)-1H-1,2,4-triaz-
ole-3,5-diamine;
1-(6,7-dihydro-5H-pyrido[2',3':6,7]cyclohepta[1,2-c]
pyridazin-3-yl)-N³-((7S)-7-(cyclohexylamino)-6,7,8,
9-tetrahydro-5H-benzo[7]annulen-2-yl)-1H-1,2,4-tri-
azole-3,5-diamine;
1-(6,7-dihydro-5H-pyrido[2',3':6,7]cyclohepta[1,2-c]
pyridazin-3-yl)-N³-((7S)-7-((methylethyl)amino)-6,7,
8,9-tetrahydro-5H-benzo[7]annulen-2-yl)-1H-1,2,4-
triazole-3,5-diamine;
1-(6,7-dihydro-5H-pyrido[2',3':6,7]cyclohepta[1,2-c]
pyridazin-3-yl)-N³-((7S)-7-(cyclopentylamino)-6,7,8,
9-tetrahydro-5H-benzo[7]annulen-2-yl)-1H-1,2,4-tri-
azole-3,5-diamine; and
1-(6,7-dihydro-5H-pyrido[2',3':6,7]cyclohepta[1,2-c]
pyridazin-3-yl)-N³-((7S)-7-(2-butylamino)-6,7,8,9-tet-
rahydro-5H-benzo[7]annulen-2-yl)-1H-1,2,4-triazole-
3,5-diamine,
or pharmaceutically acceptable salts thereof.

3. The method according to claim 1, wherein the Axl inhibitor is 1-(6,7-dihydro-5H-benzo[6,7]cyclohepta[1,2-c]pyridazin-3-yl)-N³-((7-(S)-pyrrolidin-1-yl)-6,7,8,9-tetrahydro-5H-benzo[7]annulen-2-yl)-1H-1,2,4-triazole-3,5-diamine, or a pharmaceutically acceptable salt thereof.

4. The method according to claim 1, wherein the at least two immune checkpoint inhibitors are selected from the group consisting of anti-CTLA-4 antibodies, anti-PD-1 antibodies, anti-PD-L1 antibodies, anti-4-1BB antibodies, anti-OX-40 antibodies, anti-GITR antibodies, anti-CD27 antibodies, anti-CD40 antibodies, and anti-LAG3 antibodies.

5. The method according to claim 4, wherein the at least two immune checkpoint inhibitors are selected from the group consisting of anti-CTLA-4 antibodies and anti-PD-1 antibodies.

6. The method according to claim 5, wherein the at least two immune checkpoint inhibitors are selected from the group consisting of ipilimumab, tremelimumab, pembrolizumab, and nivolumab.

7. The method according to claim 1, wherein the at least two immune checkpoint inhibitors comprise an anti-CTLA-4 antibody and an anti-PD-1 antibody.

8. The method according to claim 1, wherein the Axl inhibitor and the at least two immune checkpoint inhibitors are administered concurrently.

9. The method according to claim 1, wherein the Axl inhibitor and the at least two immune checkpoint inhibitors are administered separately and/or sequentially.

10. The method according to claim 1, wherein the cancer is breast cancer.

11. A method of controlling cancer in a patient to whom an immune checkpoint inhibitor has been or will be administered, the method comprising administering to a patient in need thereof a therapeutically effective amount of an Axl inhibitor;
wherein the Axl inhibitor is a compound of formula (I):

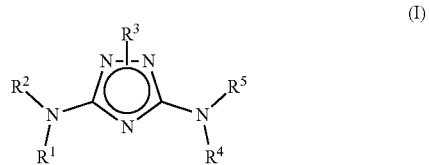

wherein:
$R^1$, $R^4$ and $R^5$ are each independently selected from the group consisting of hydrogen, alkyl, alkenyl, aryl, aralkyl, —C(O)R$^8$, —C(O)N(R$^6$)R$^7$, and —C(=NR$^6$)N(R$^6$)R$^7$;
$R^2$ and $R^3$ are each independently a polycyclic heteroaryl containing more than 14 ring atoms optionally substituted by one or more substituents selected from the group consisting of oxo, thioxo, cyano, nitro, halo, haloalkyl, alkyl, optionally substituted cycloalkyl, optionally substituted cycloalkylalkyl, optionally substituted aryl, optionally substituted aralkyl, optionally substituted heteroaryl, optionally substituted heterocyclyl, —R$^9$—OR$^8$, —R$^9$—O—R$^{10}$—OR$^8$, —R$^9$—O—R$^{10}$—O—R$^{10}$—OR$^8$, —R$^9$—O—R$^{10}$—CN, —R$^9$—O—R$^{10}$—C(O)OR$^8$, —R$^9$—O—R$^{10}$—C(O)N(R$^6$)R$^7$, —R$^9$—O—R$^{10}$—S(O)$_p$R$^8$ (where p is 0, 1 or 2), —R$^9$—O—R$^{10}$—N(R$^6$)R$^7$, —R$^9$—O—R$^{10}$—C(NR$^{11}$)N(R$^{11}$)H, —R$^9$—OC(O)—R$^8$, —R$^9$—N(R$^6$)R$^7$, —R$^9$—C(O)R$^8$, —R$^9$—C(O)OR$^8$, —R$^9$—C(O)N(R$^6$)R$^7$, —R$^9$—N(R$^6$)C(O)OR$^8$, —R$^9$—N(R$^6$)C(O)R$^8$, —R$^9$—N(R$^6$)S(O)$_t$R$^8$ (where t is 1 or 2), —R$^9$—S(O)$_t$OR$^8$ (where t is 1 or 2), —R$^9$—S(O)$_p$R$^8$ (where p is 0, 1 or 2), and —R$^9$—S(O)$_t$N(R$^6$)R$^7$ (where t is 1 or 2);
or R$^2$ is a polycyclic heteroaryl containing more than 14 ring atoms as described above and R$^3$ is selected from the group consisting of aryl and heteroaryl, where the aryl and the heteroaryl are each independently optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —R$^{13}$—OR$^{12}$, —R$^{13}$—OC(O)—R$^{12}$, —R$^{13}$—O—R$^{14}$—N(R$^{12}$)$_2$, —R$^{13}$—N(R$^{12}$)—R$^{14}$—N(R$^{12}$)$_2$, —R$^{13}$—N(R$^{12}$)—R$^{14}$—N(R$^{12}$)$_2$, —R$^{13}$—N(R$^{12}$)$_2$, —R$^{13}$—C(O)R$^{12}$, —R$^{13}$—C(O)OR$^{12}$, —R$^{13}$—C(O)N(R$^{12}$)$_2$, —R$^{13}$—C(O)N(R$^{12}$)—R$^{14}$—N(R$^{12}$)R$^{13}$, —R$^{13}$—C(O)N(R$^{12}$)—R$^{14}$—OR$^{12}$, —R$^{13}$—N(R$^{12}$)C(O)OR$^{12}$, —R$^{13}$—N(R$^{12}$)C(O)R$^{12}$, —R$^{13}$—N(R$^{12}$)S(O)$_t$R$^{12}$ (where t is 1 or 2), —$R^{13}$—S(O)$_t$O$R^{12}$ (where t is 1 or 2), —$R^{13}$—S(O)$_p$$R^{12}$ (where p is 0, 1 or 2), and —$R^{13}$—S(O)$_t$N($R^{12}$)$_2$ (where t is 1 or 2);

or $R^3$ is a polycyclic heteroaryl containing more than 14 ring atoms as described above, and $R^2$ is selected from the group consisting of aryl and heteroaryl, where the aryl and the heteroaryl are each independently optionally substituted by one or more substituents selected from the group consisting of alkyl, alkenyl, alkynyl, halo, haloalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{13}$—O$R^{12}$, —$R^{13}$—OC(O)—$R^{12}$, —$R^{13}$—O—$R^{14}$—N($R^{12}$)$_2$, —$R^{13}$—N($R^{12}$)—$R^{14}$—N($R^{12}$)$_2$, —$R^{13}$—N($R^{12}$)—$R^{14}$—N($R^{12}$)$_2$, —$R^{13}$—N($R^{12}$)$_2$, —$R^{13}$—C(O)O$R^{12}$, —$R^{13}$—C(O)N($R^{12}$)$_2$, —$R^{13}$—C(O)N($R^{12}$)—$R^{14}$—N($R^{12}$)$R^{13}$, —$R^{13}$—C(O)N($R^{12}$)—$R^{14}$—O$R^{12}$, —$R^{13}$—N($R^{12}$)C(O)O$R^{12}$, —$R^{13}$—N($R^{12}$)C(O)$R^{12}$, —$R^{13}$—N($R^{12}$)S(O)$_t$$R^{12}$ (where t is 1 or 2), —$R^{13}$—S(O)$_t$O$R^{12}$ (where t is 1 or 2), —$R^{13}$—S(O)$_p$$R^{12}$ (where p is 0, 1 or 2), and —$R^{13}$—S(O)$_t$N($R^{12}$)$_2$ (where t is 1 or 2);

each $R^6$ and $R^7$ is independently selected from the group consisting of hydrogen, alkyl, alkenyl, alkynyl, haloalkyl, haloalkenyl, haloalkynyl, hydroxyalkyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, optionally substituted heteroarylalkynyl, —$R^{10}$—O$R^8$, —$R^{10}$—CN, —$R^{10}$—NO$_2$, —$R^{10}$—N($R^8$)$_2$, —$R^{10}$—C(O)O$R^8$ and —$R^{10}$—C(O)N($R^8$)$_2$, or any $R^6$ and $R^7$, together with the common nitrogen to which they are both attached, form an optionally substituted N-heteroaryl or an optionally substituted N-heterocyclyl;

each $R^8$ is independently selected from the group consisting of hydrogen, alkyl, alkenyl, alkynyl, haloalkyl, haloalkenyl, haloalkynyl, optionally substituted aryl, optionally substituted aralkyl, optionally substituted aralkenyl, optionally substituted aralkynyl, optionally substituted cycloalkyl, optionally substituted cycloalkylalkyl, optionally substituted cycloalkylalkenyl, optionally substituted cycloalkylalkynyl, optionally substituted heterocyclyl, optionally substituted heterocyclylalkyl, optionally substituted heterocyclylalkenyl, optionally substituted heterocyclylalkynyl, optionally substituted heteroaryl, optionally substituted heteroarylalkyl, optionally substituted heteroarylalkenyl, and optionally substituted heteroarylalkynyl;

each $R^9$ is independently selected from the group consisting of a direct bond, an optionally substituted straight or branched alkylene chain, an optionally substituted straight or branched alkenylene chain and an optionally substituted straight or branched alkynylene chain;

each $R^{10}$ is independently selected from the group consisting of an optionally substituted straight or branched alkylene chain, an optionally substituted straight or branched alkenylene chain and an optionally substituted straight or branched alkynylene chain;

each $R^{11}$ is independently selected from the group consisting of hydrogen, alkyl, cyano, nitro and —O$R^8$;

each $R^{12}$ is independently selected from the group consisting of hydrogen, alkyl, alkenyl, haloalkyl, optionally substituted cycloalkyl, optionally substituted cycloalkylalkyl, optionally substituted aryl, optionally substituted aralkyl, optionally substituted heterocyclyl, optionally substituted heterocyclylalkyl, optionally substituted heteroaryl, optionally substituted heteroarylalkyl, —$R^{10}$—O$R^8$, —$R^{10}$—CN, —$R^{10}$—NO$_2$, —$R^{10}$—N($R^8$)$_2$, —$R^{10}$—C(O)O$R^8$ and —$R^{10}$—C(O)N($R^8$)$_2$, or two $R^{12}$'s, together with the common nitrogen to which they are both attached, form an optionally substituted N-heterocyclyl or an optionally substituted N-heteroaryl;

each $R^{13}$ is independently selected from the group consisting of a direct bond, an optionally substituted straight or branched alkylene chain and an optionally substituted straight or branched alkenylene chain; and each $R^{14}$ is independently selected from the group consisting of an optionally substituted straight or branched alkylene chain and an optionally substituted straight or branched alkenylene chain;

as an isolated stereoisomer or mixture thereof or as a tautomer or mixture thereof, or a pharmaceutically acceptable salt or N-oxide thereof, wherein the immune checkpoint inhibitor is an anti-CTLA-4 antibody or an anti-PD-1 antibody; and wherein cancer is an Axl-expressing cancer.

12. The method according to claim 1, further comprising administering to the patient in need thereof a therapeutically effective amount of one or more oncolytic viruses in concurrent, separate or sequential combination.

13. The method according to claim 12, wherein the one or more oncolytic viruses are selected from reovirus, Newcastle disease virus, adenovirus, herpes virus, polio virus, mumps virus, measles virus, influenza virus, vaccinia virus, rhabdovirus, vesicular stomatitis virus, and derivatives and variants thereof.

14. The method according to claim 11, wherein an oncolytic virus has also been or will also be administered.

15. The method of claim 1, wherein said controlling is delaying spread of cancer.

16. The method of claim 1, wherein said controlling is minimizing spread of cancer.

17. The method of claim 11, wherein said controlling is delaying spread of cancer.

18. The method of claim 11, wherein said controlling is minimizing spread of cancer.

* * * * *

UNITED STATES PATENT AND TRADEMARK OFFICE
CERTIFICATE OF CORRECTION

Page 1 of 2

PATENT NO. : 11,534,440 B2
APPLICATION NO. : 16/738103
DATED : December 27, 2022
INVENTOR(S) : James Bradley Lorens and Gro Gausdal It is certified that error appears in the above-identified patent and that said Letters Patent is hereby corrected as shown below:

In the Specification

Column 3, Lines 50-59: Change "  " to 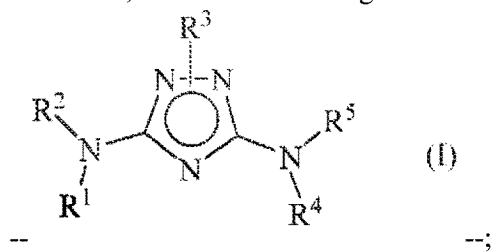 --;

Column 25, Lines 57-65: Change " " to --;

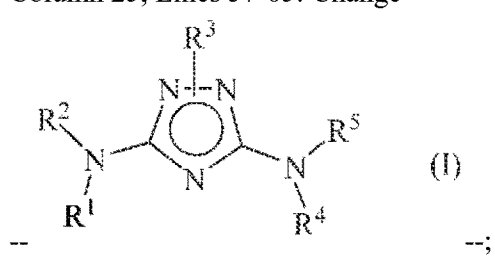

Signed and Sealed this
Eleventh Day of April, 2023

Katherine Kelly Vidal
*Director of the United States Patent and Trademark Office*

CERTIFICATE OF CORRECTION (continued)

In the Claims

Claim 1, Column 81, Lines 32-40: Change " 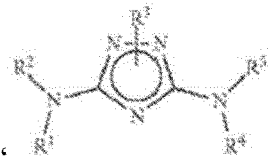 " to -- 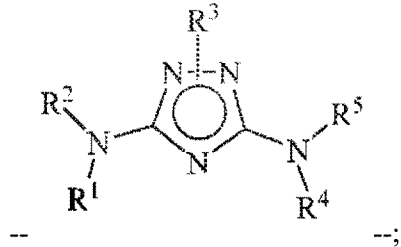 --;

Claim 1, Column 82, Line 19: Change "–$R^{13}$–C(O)O$R^{12}$," to -- –$R^{13}$–C(O)$R^{12}$, –$R^{13}$–C(O)O$R^{12}$, --;

Claim 1, Column 82, Line 47: Change "–$R^{13}$–C(O)O$R^{12}$," to -- –$R^{13}$–C(O)$R^{12}$, –$R^{13}$–C(O)O$R^{12}$, --; and Claim 11, Column 89, Line 25: Change "–$R^{13}$–C(O)O$R^{12}$," to -- –$R^{13}$–C(O)$R^{12}$, –$R^{13}$–C(O)O$R^{12}$, --.